(12) United States Patent
Kim et al.

(10) Patent No.: US 12,216,129 B2
(45) Date of Patent: Feb. 4, 2025

(54) HUMAN ANTIBODY HAVING HIGH AFFINITY TO HUMAN IL-4 RECEPTOR ALPHA

(71) Applicant: AJOU UNIVERSITY INDUSTRY-ACADEMIC COOPERATION FOUNDATION, Suwon-si (KR)

(72) Inventors: Yong Sung Kim, Suwon-si (KR); Hae-Sim Park, Seoul (KR); Jung Eun Kim, Seoul (KR); Keunok Jung, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 877 days.

(21) Appl. No.: 17/292,050

(22) PCT Filed: Nov. 7, 2019

(86) PCT No.: PCT/KR2019/015083
§ 371 (c)(1),
(2) Date: May 7, 2021

(87) PCT Pub. No.: WO2020/096381
PCT Pub. Date: May 14, 2020

(65) Prior Publication Data
US 2021/0403580 A1  Dec. 30, 2021

(30) Foreign Application Priority Data
Nov. 9, 2018 (KR) .......................... 10-2018-0137199

(51) Int. Cl.
| A61K 47/68 | (2017.01) |
| A61P 29/00 | (2006.01) |
| C07K 16/28 | (2006.01) |
| G01N 33/68 | (2006.01) |

(52) U.S. Cl.
CPC ..... *G01N 33/6869* (2013.01); *A61K 47/6845* (2017.08); *A61P 29/00* (2018.01); *C07K 16/2866* (2013.01); *G01N 33/6893* (2013.01); *G01N 2333/7155* (2013.01); *G01N 2800/24* (2013.01)

(58) Field of Classification Search
CPC ............ C07K 16/2866; A61K 47/6803; A61K 47/6845
See application file for complete search history.

(56) References Cited

U.S. PATENT DOCUMENTS

| 7,605,237 B2 | 10/2009 | Stevens et al. |
| 2009/0074793 A1 | 3/2009 | Martin et al. |
| 2012/0097565 A1 | 4/2012 | Dix et al. |
| 2013/0243776 A1 | 9/2013 | Rao et al. |
| 2023/0203172 A1 | 6/2023 | Zhang et al. |

FOREIGN PATENT DOCUMENTS

| CA | 2 937 387 A1 | 7/2015 |
| CN | 108373505 A | 8/2018 |
| CN | 108409860 A | 8/2018 |
| CN | 110105451 A | 8/2019 |
| CN | 111690066 A | 9/2020 |
| EP | 1 692 184 B1 | 3/2012 |
| KR | 10-1474227 B1 | 12/2014 |
| KR | 10-2016-0014626 A | 2/2016 |
| KR | 10-2016-0056950 A | 5/2016 |
| KR | 10-1620539 B1 | 5/2016 |
| KR | 10-2017-0044739 A | 4/2017 |
| WO | 2008/054606 A2 | 5/2008 |
| WO | 2014/205365 A1 | 12/2014 |
| WO | 2019/148405 A1 | 8/2019 |

OTHER PUBLICATIONS

Baek et al., "Construction of a Large Synthetic Human Fab Antibody Library on Yeast Cell Surface by Optimized Yeast Mating", J. Microbiol. Biotechnol., vol. 24, No. 3, 2014, pp. 408-420.
Fujimoto et al., "Whole-genome mutational landscape of liver cancers displaying biliary phenotype reveals hepatitis impact and molecular diversity", Nature Communications, vol. 6, No. 6120, Jan. 30, 2015, pp. 1-8.
Ritchie et al., "Implications of receptor-mediated endocytosis and intracellular trafficking dynamics in the development of antibody drug conjugates", Landes Bioscience, vol. 5, No. 1, 2013, pp. 13-21 (10 pages).
Vaisman-Mentesh et al., "Molecular Landscape of Anti-Drug Antibodies Reveals the Mechanism of the Immune Response Following Treatment With TNFα Antagonists", Frontiers in Immunology, vol. 10, Article 2921, Dec. 18, 2019, pp. 1-19.
Laporte et al., "Molecular and structural basis of cytokine receptor pleiotropy in the Interleukin-4/13 system", Cell, vol. 132, No. 2, 2008, pp. 259-272.
Korean Intellectual Property Office, Office Action for application 10-2019-0141549 dated Feb. 3, 2021.
International Searching Authority, Written opinion for PCT/KR2019/015083 dated Feb. 20, 2020.

(Continued)

*Primary Examiner* — Elly-Gerald Stoica
(74) *Attorney, Agent, or Firm* — Sughrue Mion, PLLC

(57) ABSTRACT

An antibody or antigen-binding fragment thereof, which binds with a high pM-level affinity to a human IL-4 receptor alpha chain that is a human IL-4 receptor, is provided. The antibody or antigen-binding fragment has a different epitope and a different antigen dissociation rate than existing antibodies. A nucleic acid encoding the antibody or antigen-binding fragment thereof, a vector including the nucleic acid, a cell transformed with the vector, a method for producing the antibody or antigen-binding fragment thereof, a conjugate comprising the antibody or antigen-binding fragment thereof, a composition for preventing or treating inflammatory diseases, and a composition for diagnosing inflammatory diseases are disclosed.

8 Claims, 23 Drawing Sheets
Specification includes a Sequence Listing.

(56) References Cited

OTHER PUBLICATIONS

International Searching Authority, International search report for PCT/KR2019/015083 dated Feb. 20, 2020.
Office Action issued May 28, 2024 in Chinese Application No. 201980080760.9.

[Fig. 1A]
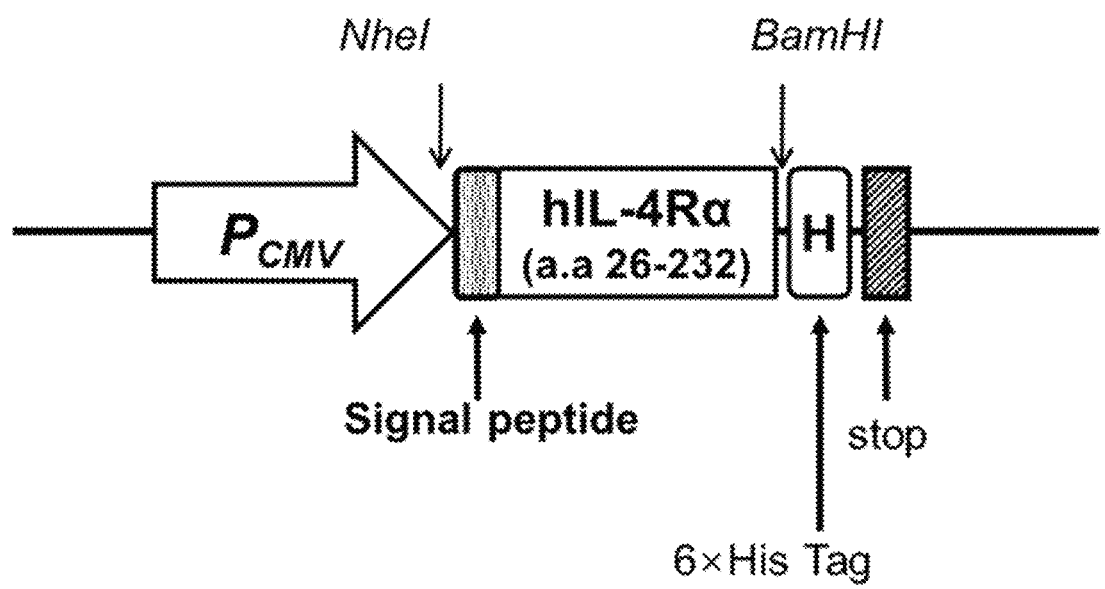

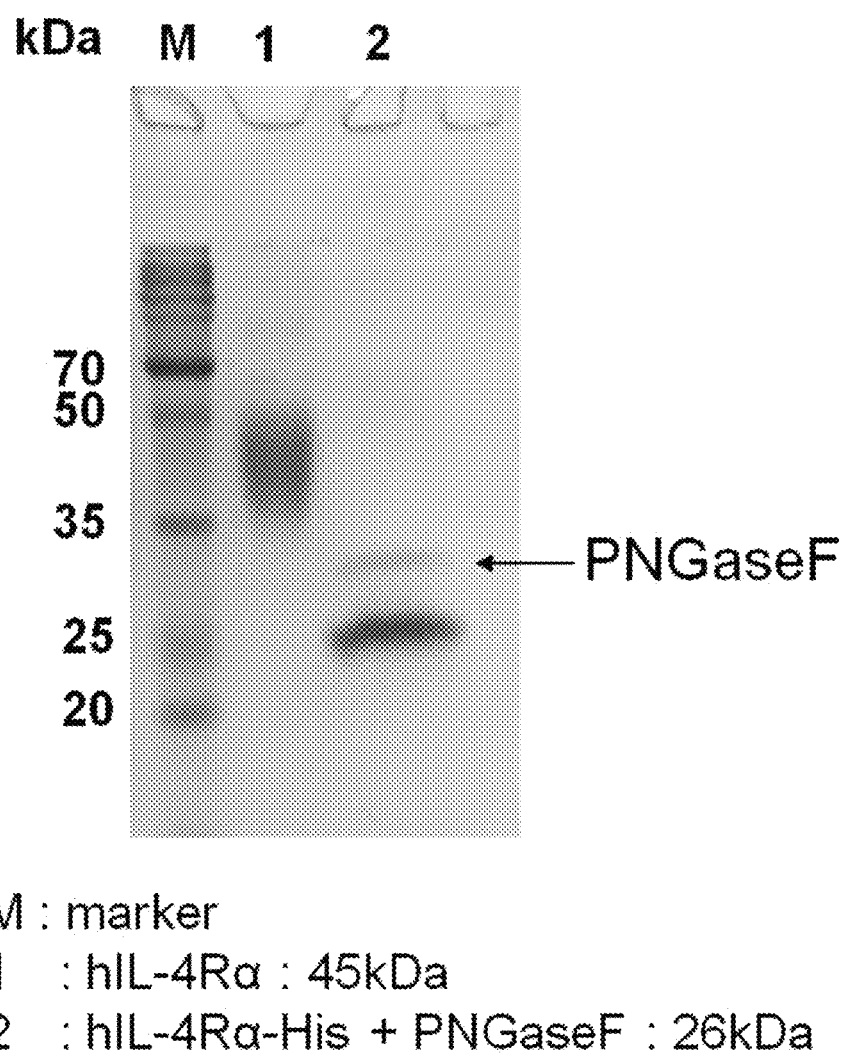
[Fig. 1B]
M : marker
1 : hIL-4Rα : 45kDa
2 : hIL-4Rα-His + PNGaseF : 26kDa

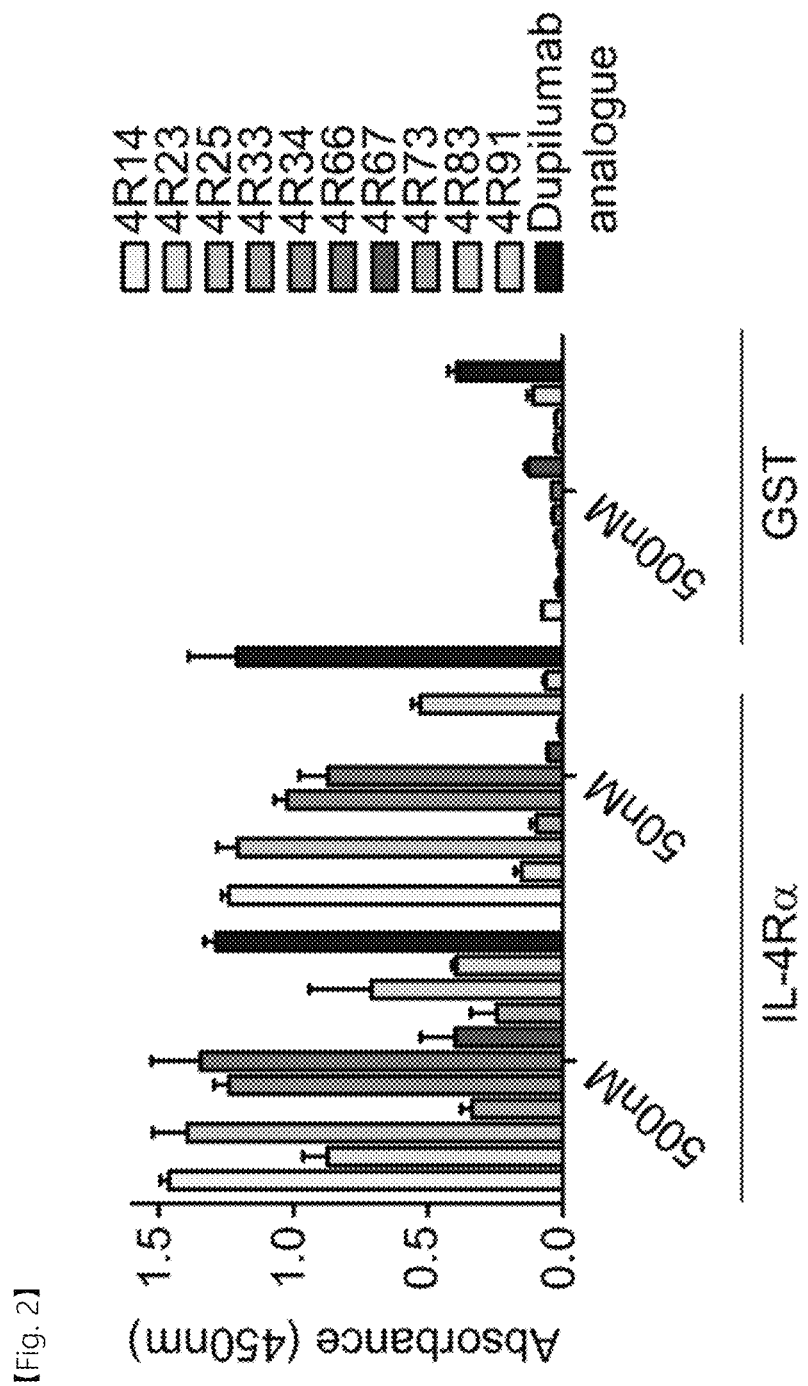
[Fig. 2]

[Fig. 3A]
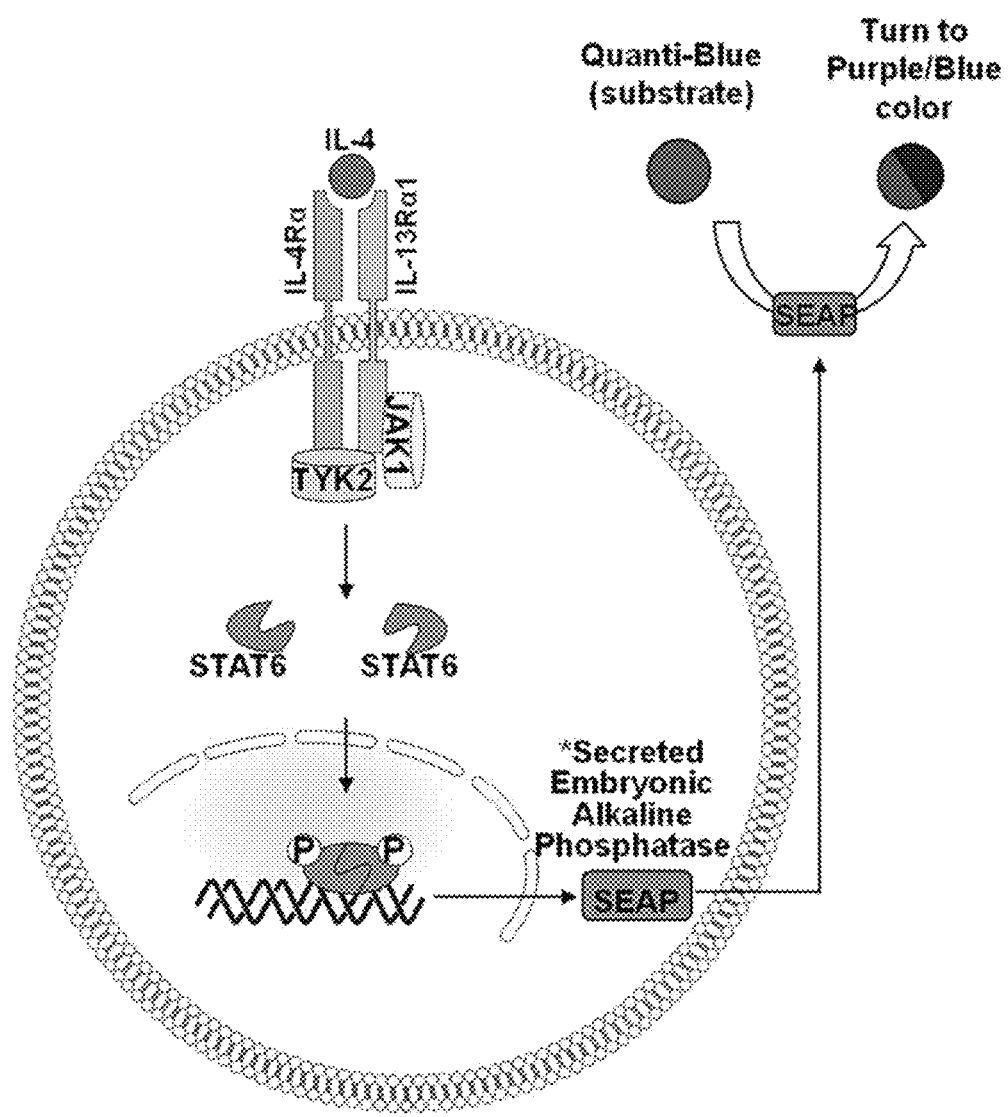

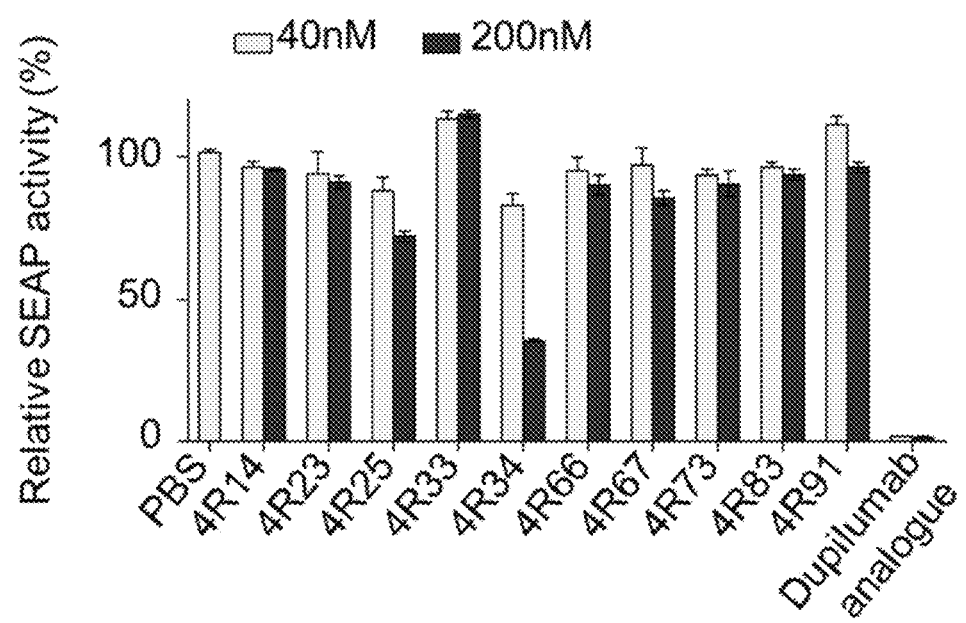

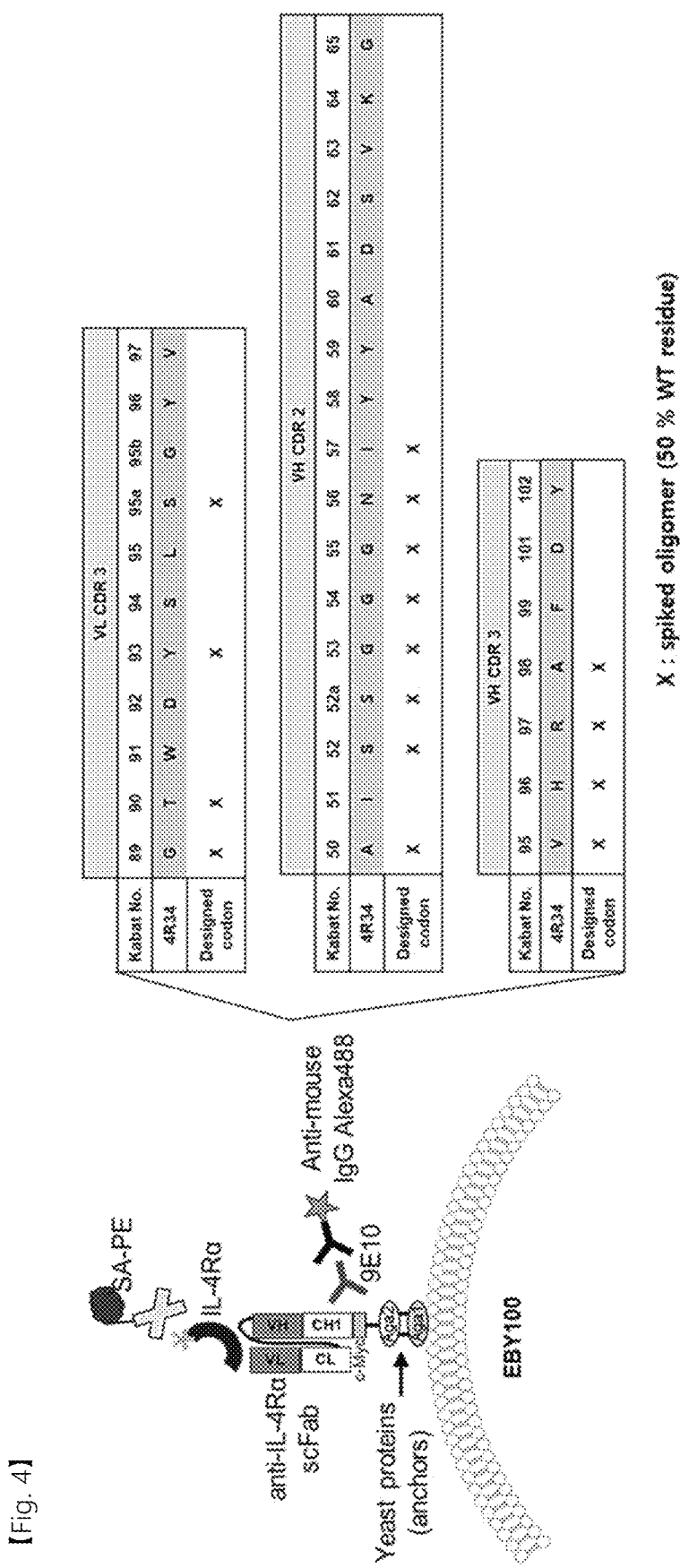
[Fig. 4]

[Fig. 5]
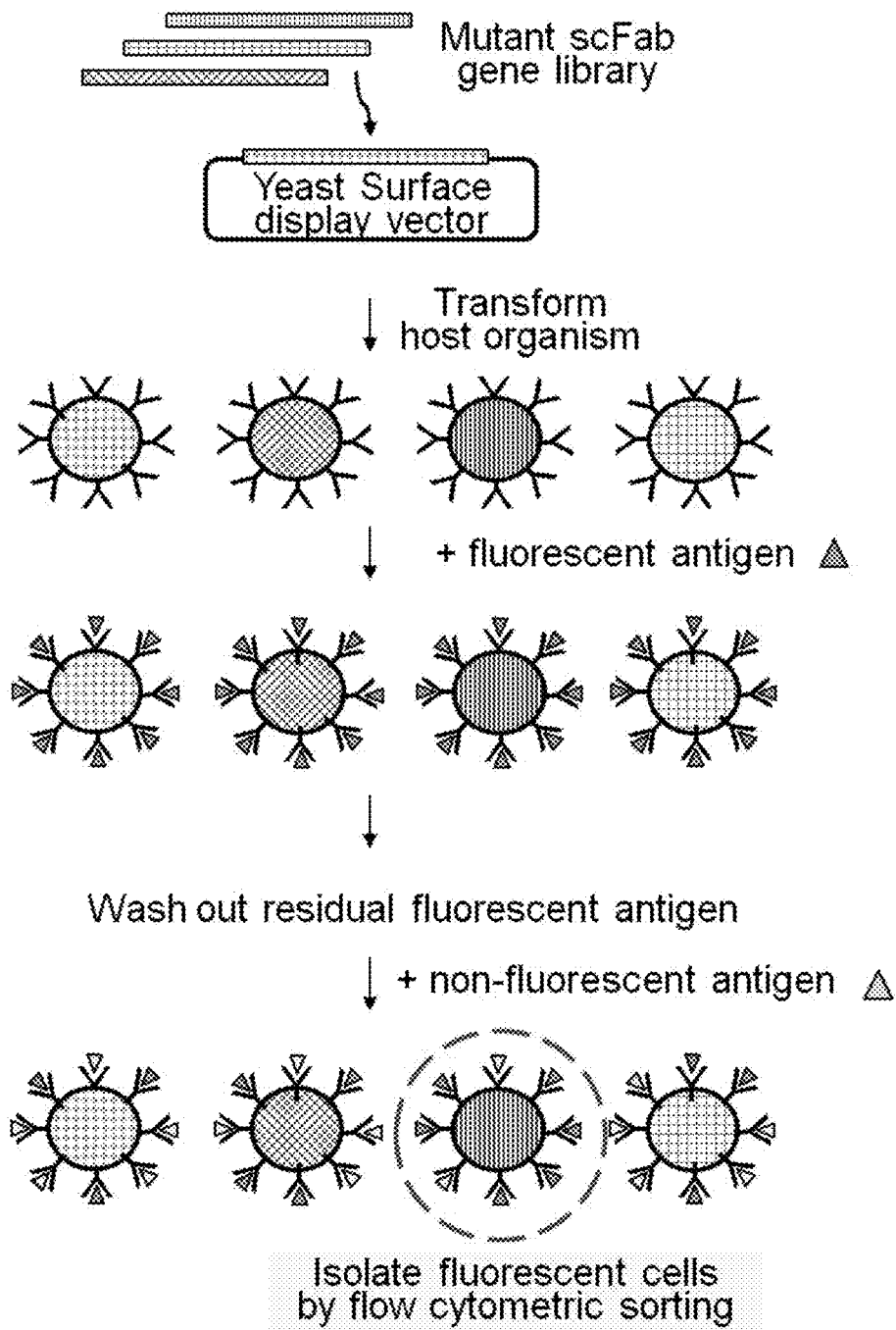

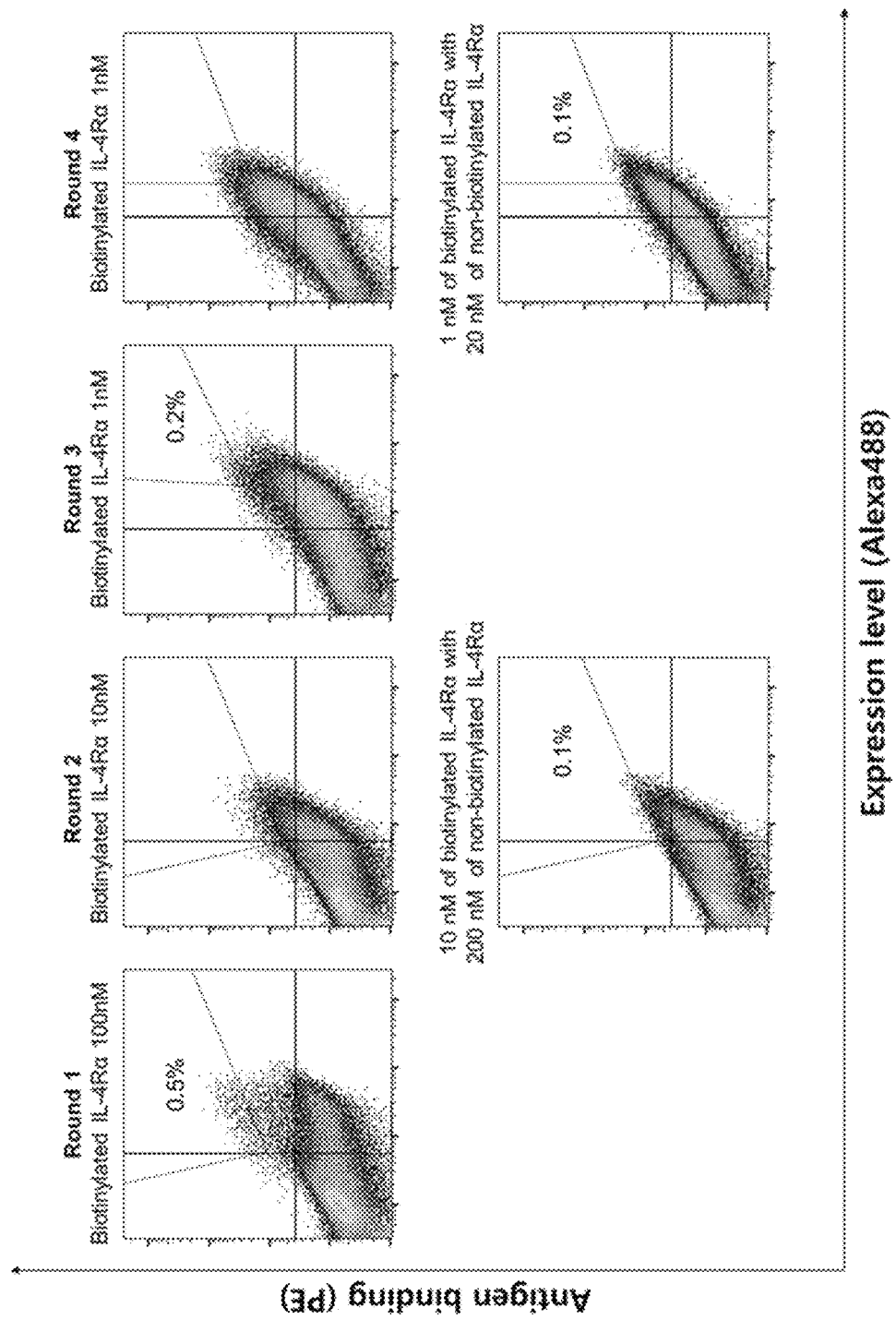

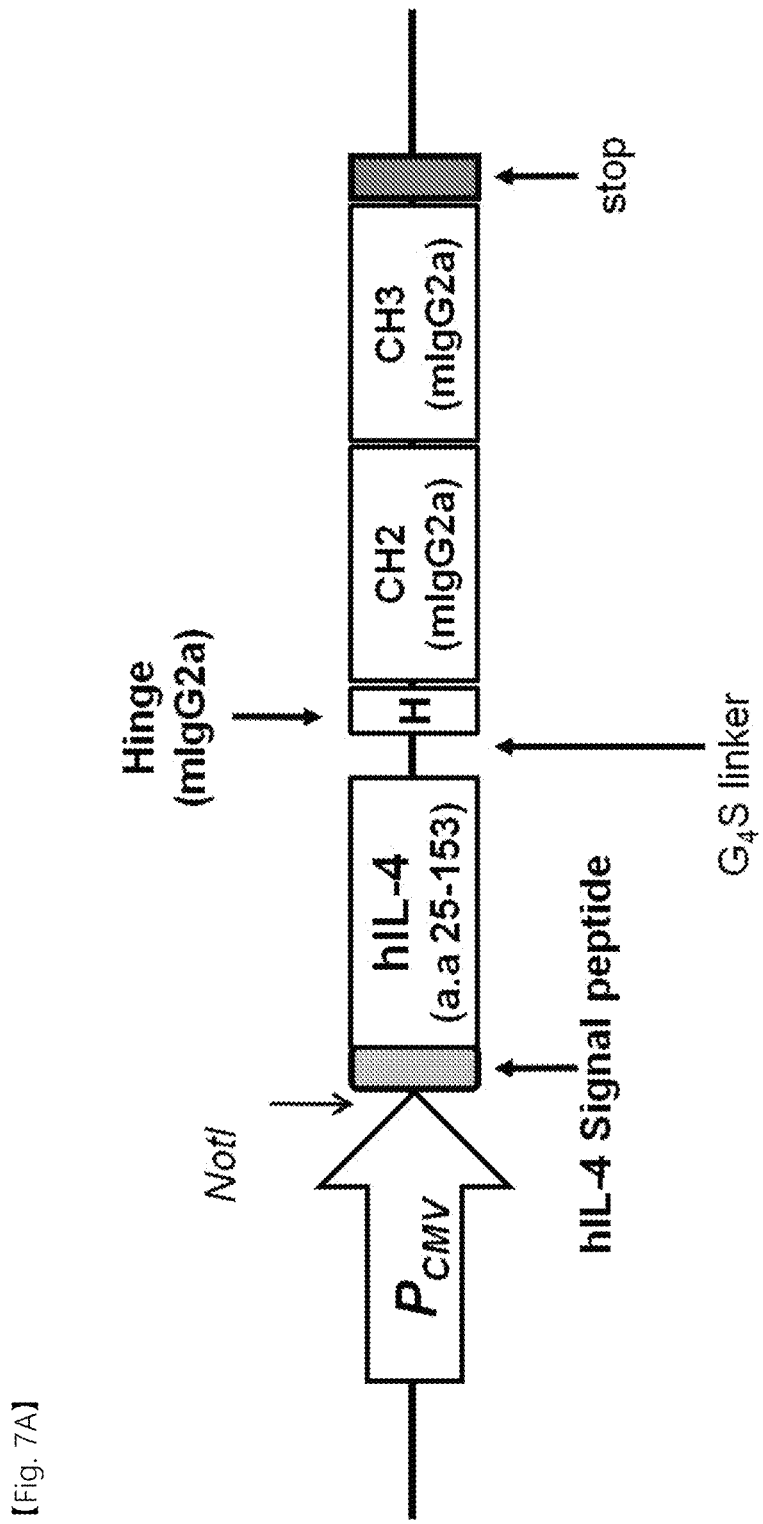
[Fig. 7A]

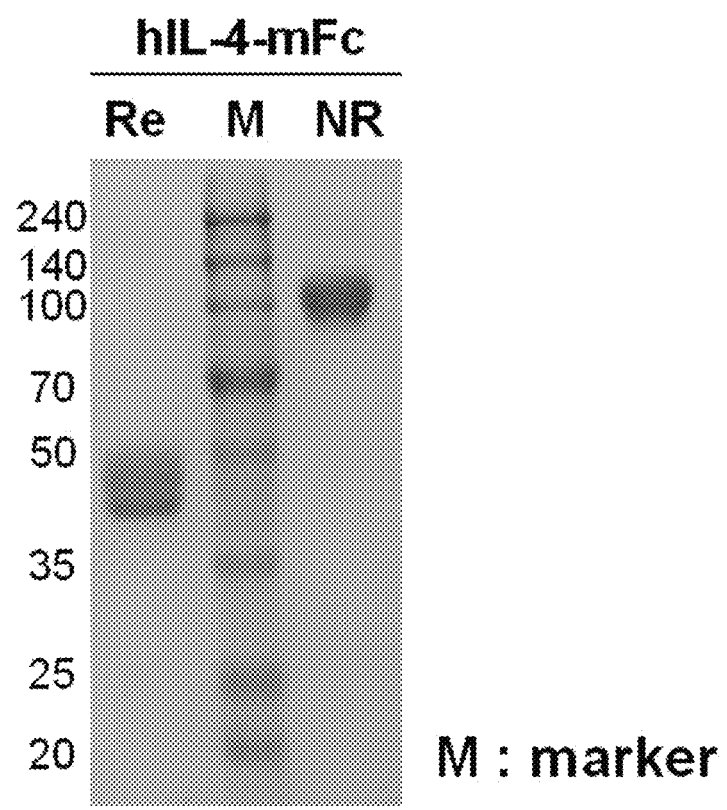
[Fig. 7B]

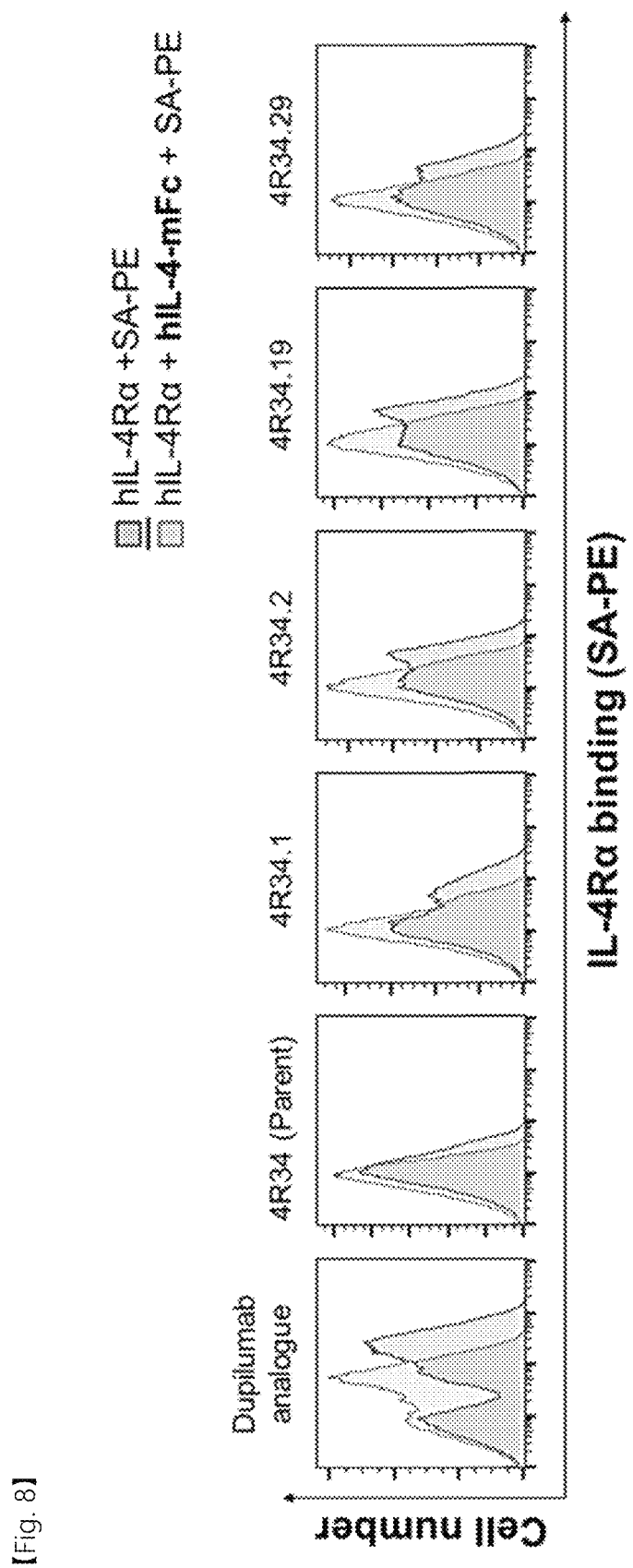
[Fig. 8]

[Fig. 9]
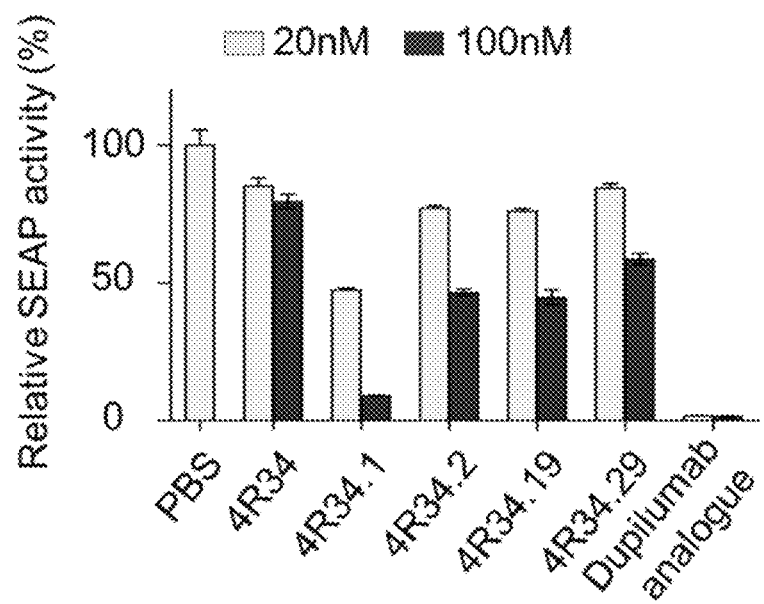

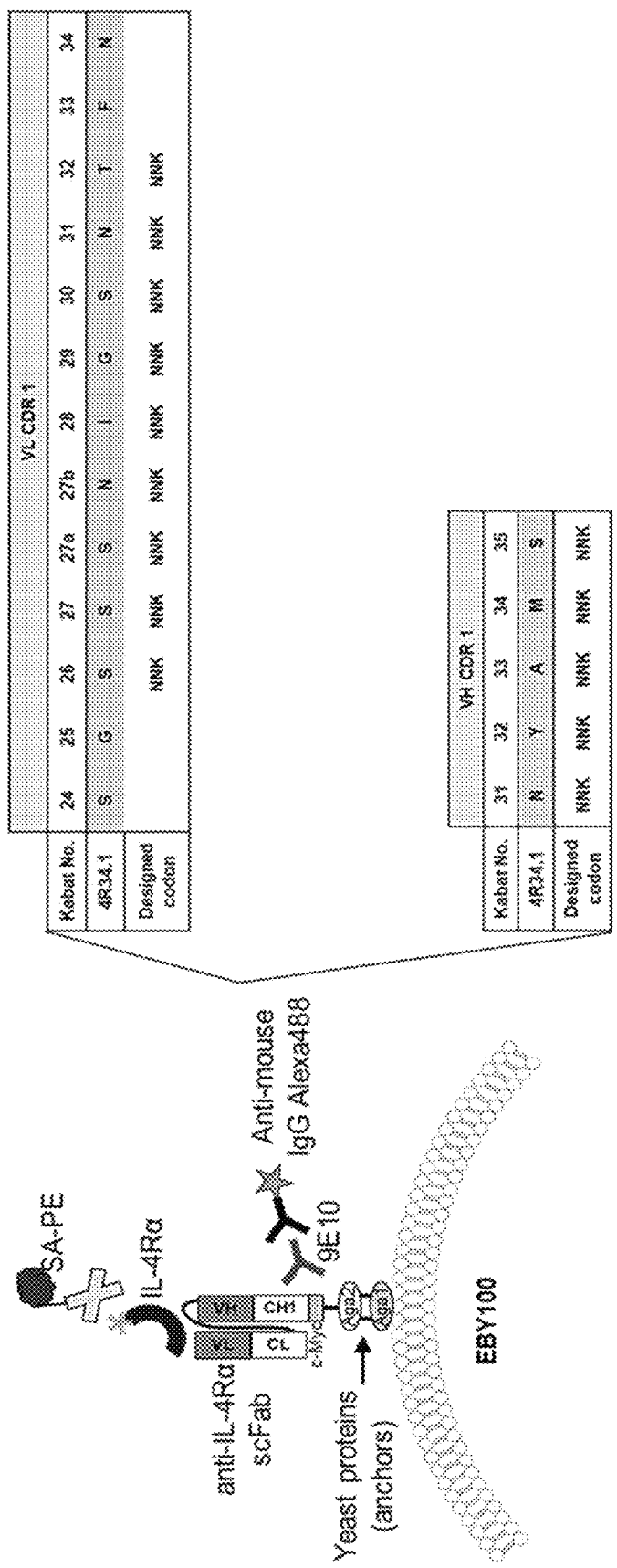
[Fig. 10]

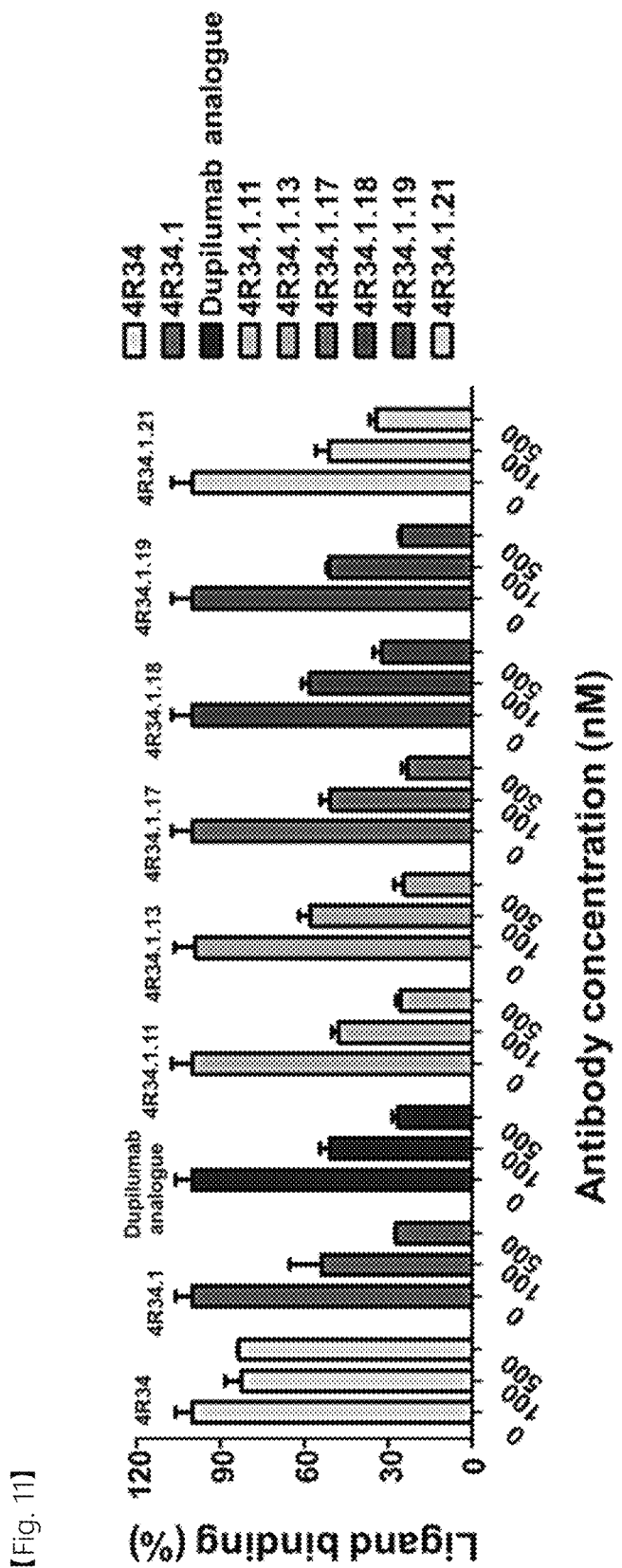
[Fig. 11]

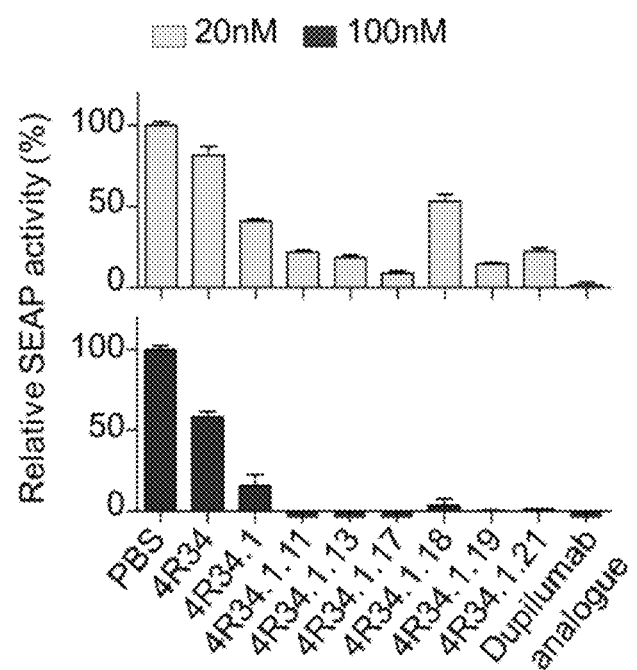
[Fig. 12]

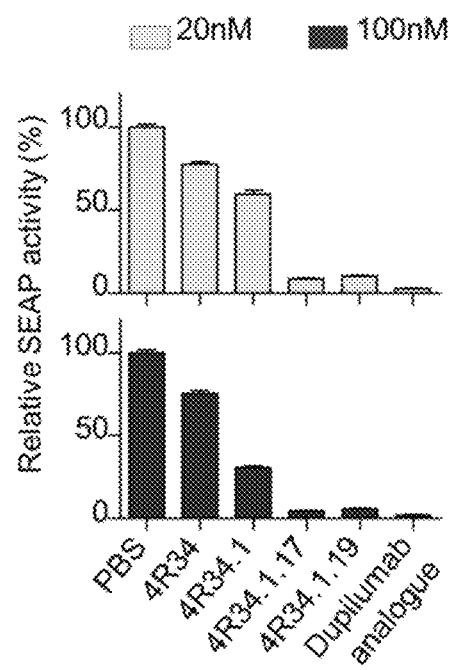
[Fig. 13]

[Fig. 14]
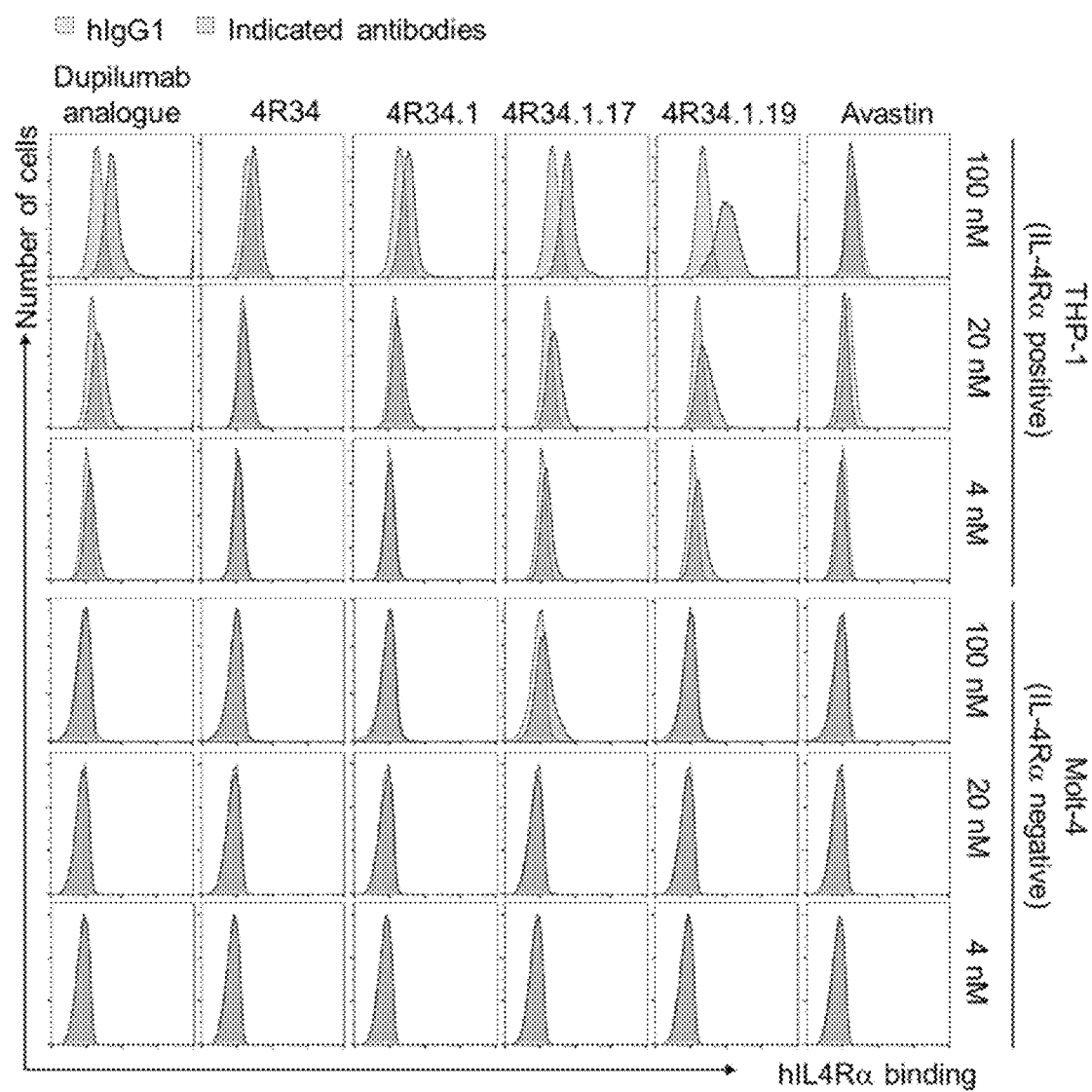

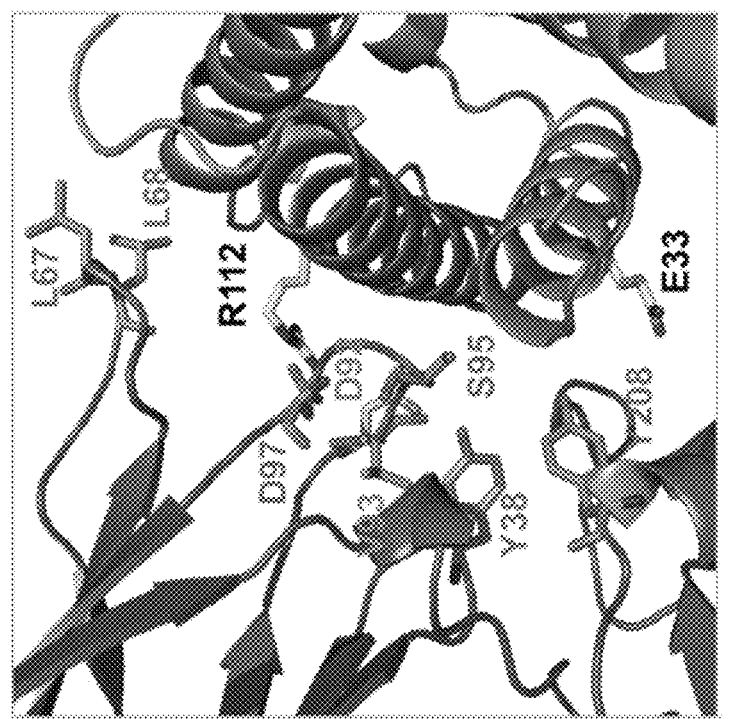
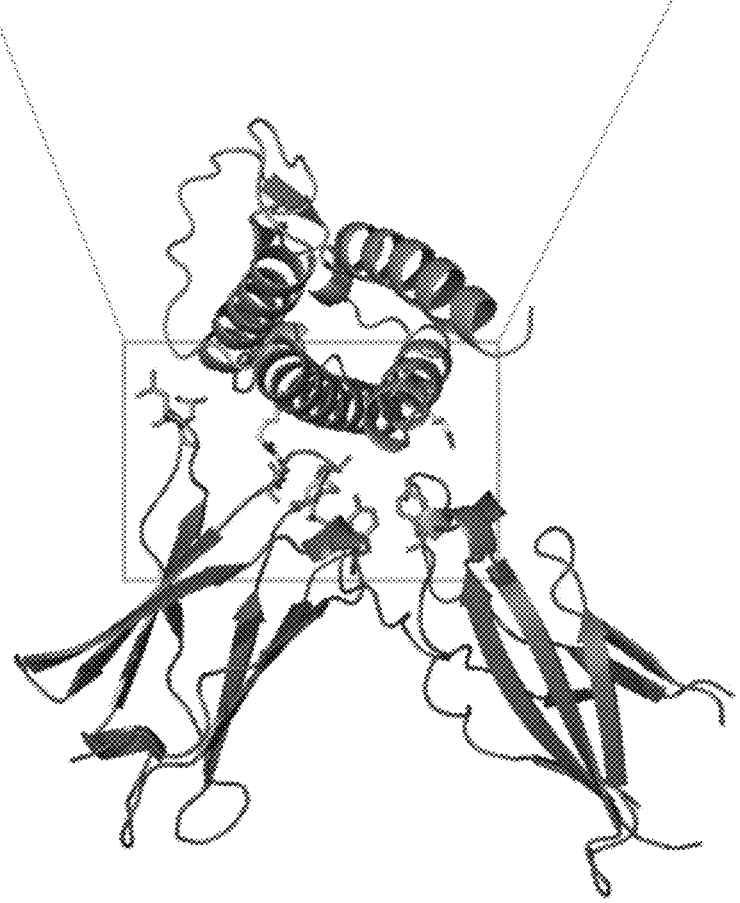
[Fig. 15A]

[Fig. 15B]
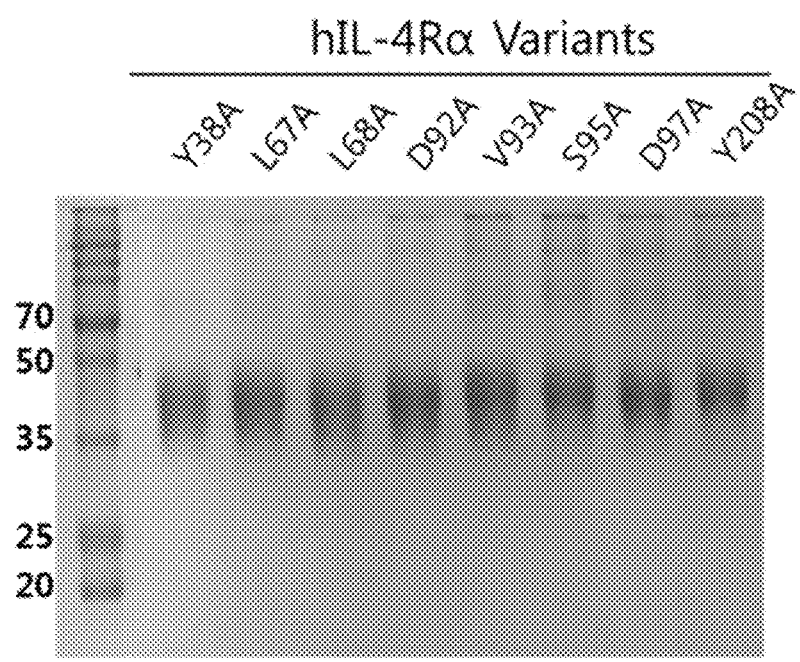

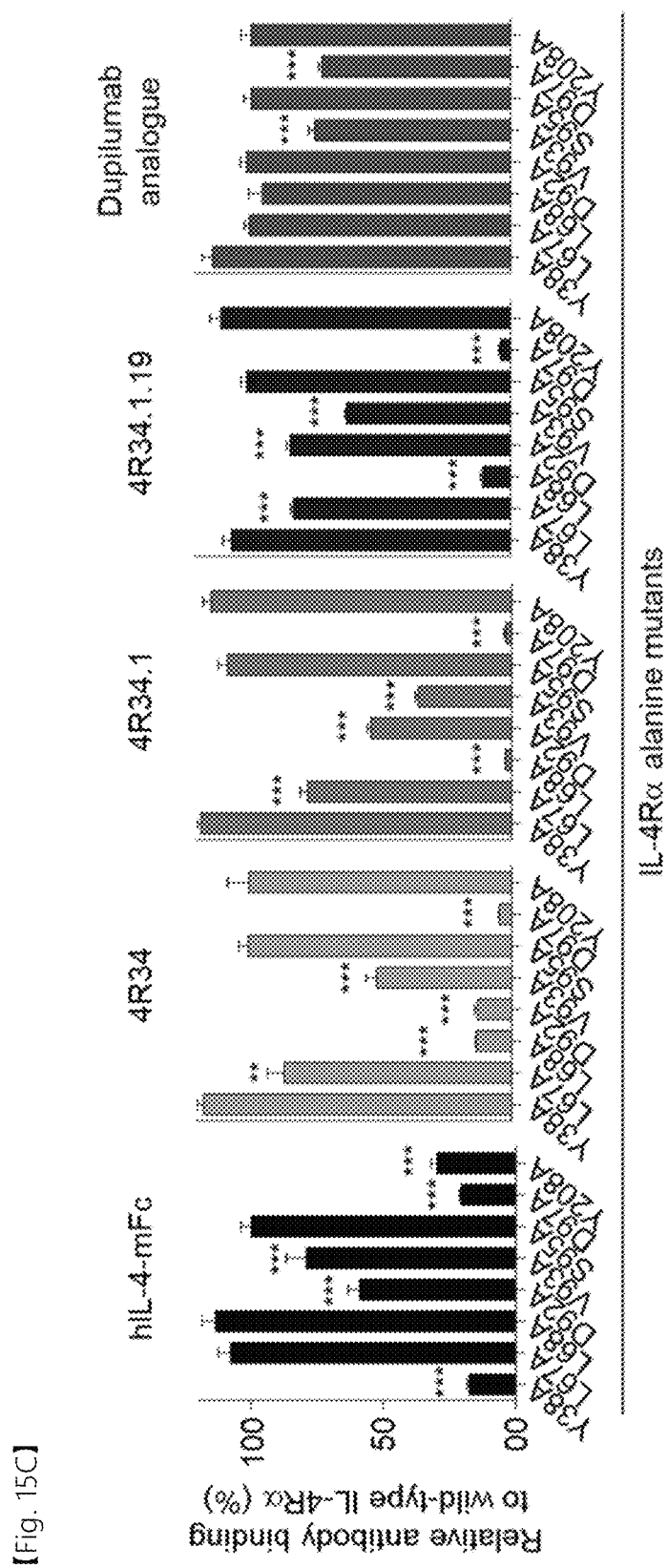
[Fig. 15C]

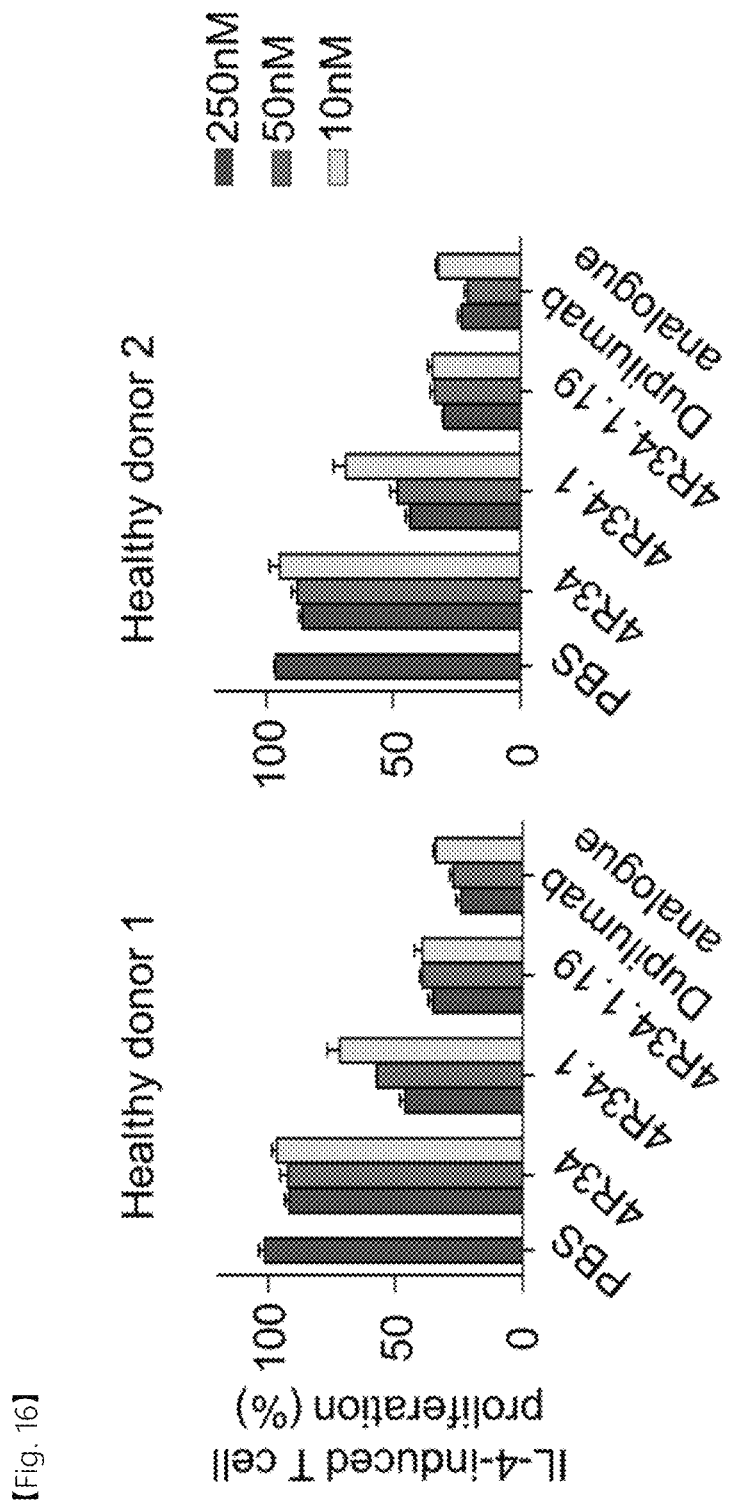
[Fig. 16]

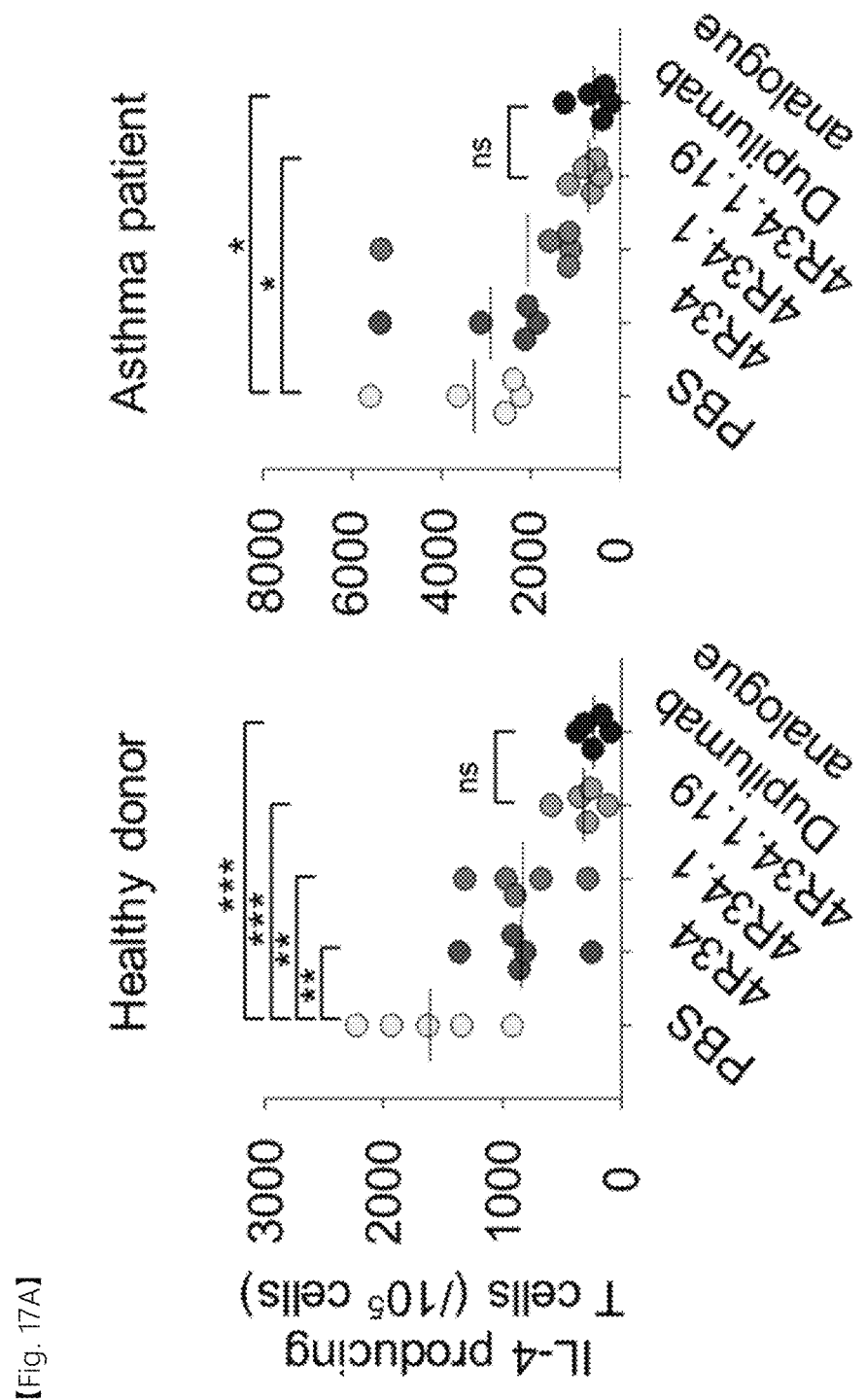
[Fig. 17A]

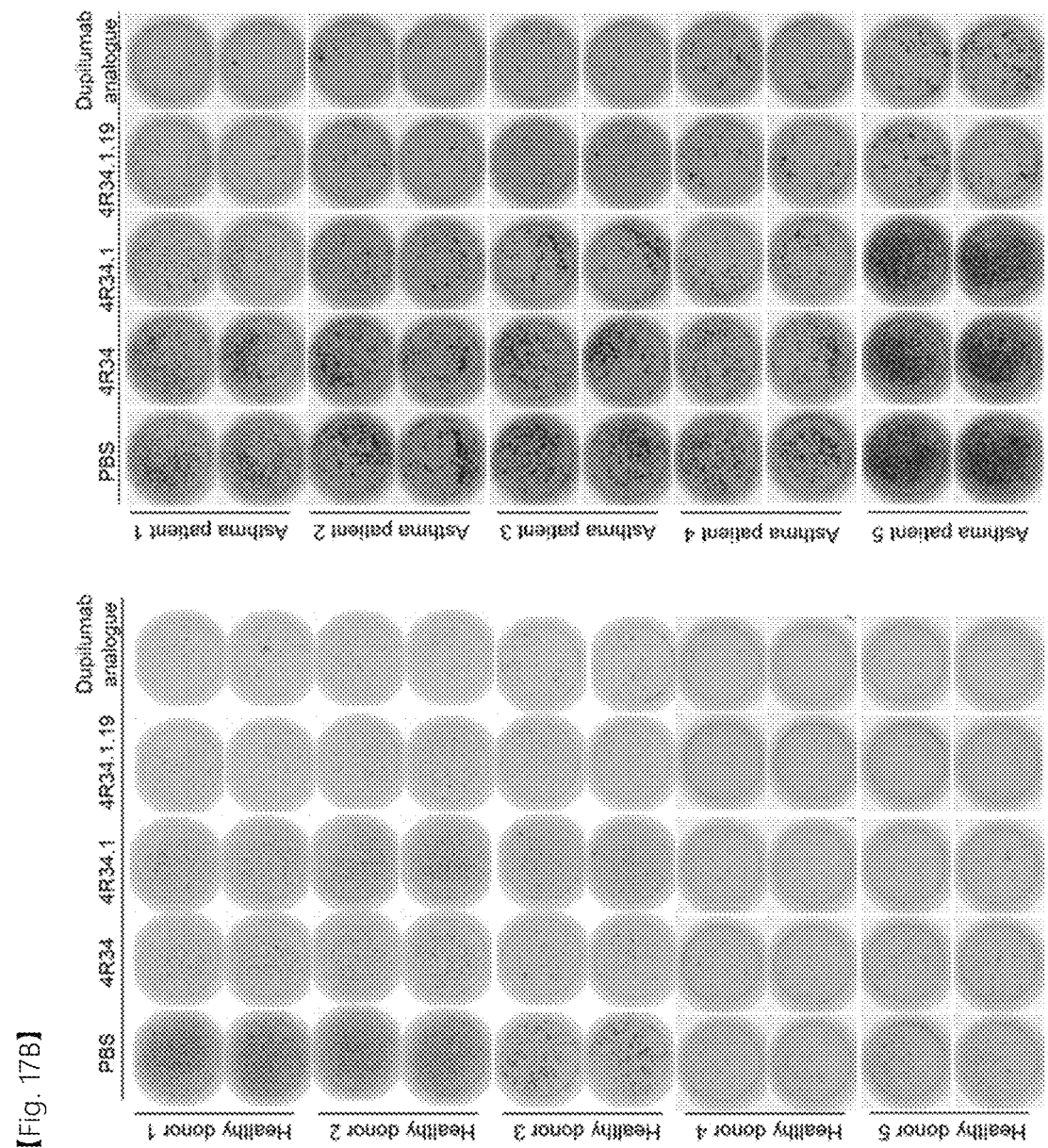
[Fig. 17B]

SEQUENCE LISTING

```
<160> NUMBER OF SEQ ID NOS: 98

<210> SEQ ID NO 1
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Ser Gly Gly Gly Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Leu Arg Arg Tyr Phe Asp Tyr Trp Gly Gln Gly Thr Leu Val
            100                 105                 110

Thr Val Ser Ser
        115

<210> SEQ ID NO 2
<211> LENGTH: 121
<212> TYPE: PRT
<213> ORGANISM: Artificial Sequence
<220> FEATURE:
<223> OTHER INFORMATION: Synthetic Sequence

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Ala Ile Ser Ser Gly Gly Ser Ile Tyr Tyr Ala Asp Ser Val
    50                  55                  60

Lys Gly Arg Phe Thr Ile Ser Arg Asp Asn Ser Lys Asn Thr Leu His
65                  70                  75                  80

Leu Gln Met Asn Ser Leu Arg Ala Glu Asp Thr Ala Val Tyr Tyr Cys
                85                  90                  95

Ala Arg Gly Pro Gln Arg Ser Ala Thr Ala Val Phe Asp Tyr Trp Gly
            100                 105                 110

Gln Gly Thr Leu Val Thr Val Ser Ser
        115                 120

<210> SEQ ID NO 3
<211> LENGTH: 127
<212> TYPE: PRT
<213> ORGANISM: Artificial Sequence
<220> FEATURE:
<223> OTHER INFORMATION: Synthetic Sequence

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Trp Ile Ser Pro Asn Ser Gly Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Pro Leu Ser Ala Ala Trp Ser His Ser Tyr Tyr Asn
            100                 105                 110

Ala Met Asp Val Trp Gly Gln Gly Thr Leu Val Thr Val Ser Ser
        115                 120                 125
```

```
<210> SEQ ID NO 4
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Met Ser Trp Val Arg Gln Ala Pro Gly Lys Gly Leu Glu Trp Val
        35                  40                  45

Ser Leu Ile Ser His Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro His Arg Ala Phe Asp Tyr Trp Gly Gln Gly Thr Leu Val
            100                 105                 110

Thr Val Ser Ser
        115

<210> SEQ ID NO 5
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Ser His Gly Ser Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro His Arg Ala Phe Asp Tyr Trp Gly Gln Gly Thr Leu Val
            100                 105                 110

Thr Val Ser Ser
        115

<210> SEQ ID NO 6
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 6

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Ser His Gly Asn Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Gly Arg His Phe Asp Tyr Trp Gly Gln Gly Thr Leu Val
            100                 105                 110

Thr Val Ser Ser
        115

<210> SEQ ID NO 7
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ser Ile Ser Pro Ser Gly Ser Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Tyr Arg Ala Phe Asp Tyr Trp Gly Gln Gly Thr Leu Val
            100                 105                 110

Thr Val Ser Ser
        115

<210> SEQ ID NO 8
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Pro Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr

Leu Gln Met Asn Ser Leu Arg Ala Glu Asp Thr Ala Val Tyr Tyr Cys
            85                  90                  95

Ala Arg Ala Lys Arg Ala Phe Asp Tyr Trp Gly Gln Gly Thr Leu Val
            100                 105                 110

Thr Val Ser Ser
            115

<210> SEQ ID NO 9
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
            35                  40                  45

Ser Ala Ile Ser Pro Gly Ser Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Phe Arg Arg His Phe Asp Tyr Trp Gly Gln Gly Thr Leu Val
            100                 105                 110

Thr Val Ser Ser
            115

<210> SEQ ID NO 10
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
            35                  40                  45

Ser Ala Ile Ser Ser Gly Gly Gly Asn Ile Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Val His Arg Ala Phe Asp Tyr Trp Gly Gln Gly Thr Leu Val
            100                 105                 110

Thr Val Ser Ser
            115

```
<210> SEQ ID NO 11
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 11

Asn Tyr Ala Met Ser
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 12

Asp Tyr Ala Met Ser
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 13

Gly Tyr Ala Met Ser
1               5

<210> SEQ ID NO 14
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 14

Ala Ile Ser Ser Gly Gly Gly Asn Ile Tyr Tyr Ala Asp Ser Val Lys
1               5                   10                  15

Gly

<210> SEQ ID NO 15
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 15

Ala Ile Ser Ser Gly Gly Ser Ser Ile Tyr Tyr Ala Asp Ser Val Lys
1               5                   10                  15

Gly

<210> SEQ ID NO 16
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 16
```

Trp Ile Ser Pro Asn Ser Gly Asn Ile Tyr Tyr Ala Asp Ser Val Lys
1               5                   10                  15

Gly

<210> SEQ ID NO 17
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 17

Leu Ile Ser His Ser Gly Ser Asn Thr Tyr Tyr Ala Asp Ser Val Lys
1               5                   10                  15

Gly

<210> SEQ ID NO 18
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 18

Gly Ile Ser His Gly Ser Gly Ser Ile Tyr Tyr Ala Asp Ser Val Lys
1               5                   10                  15

Gly

<210> SEQ ID NO 19
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 19

Gly Ile Ser His Gly Asn Gly Ser Ile Tyr Tyr Ala Asp Ser Val Lys
1               5                   10                  15

Gly

<210> SEQ ID NO 20
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 20

Ser Ile Ser Pro Ser Gly Ser Ser Ile Tyr Tyr Ala Asp Ser Val Lys
1               5                   10                  15

Gly

<210> SEQ ID NO 21
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 21

Ala Ile Ser Pro Ser Gly Gly Ser Ile Tyr Tyr Ala Asp Ser Val Lys
1               5                   10                  15

Gly

```
<210> SEQ ID NO 22
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 22

Ala Ile Ser Pro Gly Ser Gly Ser Thr Tyr Tyr Ala Asp Ser Val Lys
1               5                   10                  15

Gly

<210> SEQ ID NO 23
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 23

Leu Arg Arg Tyr Phe Asp Tyr
1               5

<210> SEQ ID NO 24
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 24

Gly Pro Gln Arg Ser Ala Thr Ala Val Phe Asp Tyr
1               5                   10

<210> SEQ ID NO 25
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 25

Arg Pro Leu Ser Ala Ala Trp Ser His Ser Ser Tyr Tyr Asn Ala Met
1               5                   10                  15

Asp Val

<210> SEQ ID NO 26
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 26

Pro His Arg Ala Phe Asp Tyr
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 27
```

```
Thr Gly Arg Asp Phe Asp Tyr
1               5
```

<210> SEQ ID NO 28
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 28

```
Thr Gly Arg His Phe Asp Tyr
1               5
```

<210> SEQ ID NO 29
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 29

```
Ser Tyr Arg Ala Phe Asp Tyr
1               5
```

<210> SEQ ID NO 30
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 30

```
Ala Lys Arg Ala Phe Asp Tyr
1               5
```

<210> SEQ ID NO 31
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 31

```
Phe Arg Arg His Phe Asp Tyr
1               5
```

<210> SEQ ID NO 32
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 32

```
Val His Arg Ala Phe Asp Tyr
1               5
```

<210> SEQ ID NO 33
<211> LENGTH: 110
<212> TYPE: PRT
<213> ORGANISM: Artificial Sequence
<220> FEATURE:
<223> OTHER INFORMATION: Synthetic Sequence

<400> SEQUENCE: 33

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
                20                  25                  30

Tyr Val Asn Trp Tyr Gln Gln Leu Pro Gly Thr Ala Pro Lys Leu Leu
            35                  40                  45

Ile Tyr Asp Asn Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Ala Ser Leu
                85                  90                  95

Ser Ala Tyr Val Phe Gly Gly Gly Thr Lys Leu Thr Val Leu
                100                 105                 110

<210> SEQ ID NO 34
<211> LENGTH: 110
<212> TYPE: PRT
<213> ORGANISM: Artificial Sequence
<220> FEATURE:
<223> OTHER INFORMATION: Synthetic Sequence

<400> SEQUENCE: 34

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
                20                  25                  30

Asn Val Ser Trp Tyr Gln Gln Leu Pro Gly Thr Ala Pro Lys Leu Leu
            35                  40                  45

Ile Tyr Ala Asn Ser Lys Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Asp Ser Leu
                85                  90                  95

Ser Ala Tyr Val Phe Gly Gly Gly Thr Lys Leu Thr Val Leu
                100                 105                 110

<210> SEQ ID NO 35
<211> LENGTH: 110
<212> TYPE: PRT
<213> ORGANISM: Artificial Sequence
<220> FEATURE:
<223> OTHER INFORMATION: Synthetic Sequence

<400> SEQUENCE: 35

Gln Ser Val Leu Thr Gln Pro Pro Ser Ala Pro Gly Thr Pro Gly Gln
1               5                   10                  15

Arg Val Thr Ile Ser Cys Thr Gly Ser Ser Asn Ile Gly Ser Asn
                20                  25                  30

Ser Val Asn Trp Tyr Gln Gln Leu Pro Gly Thr Ala Pro Lys Leu Leu
            35                  40                  45

Ile Tyr Asp Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Asp Ala Trp Asp Ser Ser Leu
                85                  90                  95
```

Ser Ala Tyr Val Phe Gly Gly Gly Thr Lys Leu Thr Val Leu
            100                 105                 110

<210> SEQ ID NO 36
<211> LENGTH: 110
<212> TYPE: PRT
<213> ORGANISM: Artificial Sequence
<220> FEATURE:
<223> OTHER INFORMATION: Synthetic Sequence

<400> SEQUENCE: 36

Gln Ser Val Leu Thr Gln Pro Pro Ser Ala Ser Gly Thr Pro Gly Gln
1               5                   10                  15

Arg Val Thr Leu Ser Cys Thr Gly Ser Ser Asn Ile Gly Ser Asn
            20                  25                  30

Tyr Val Ser Trp Tyr Gln Gln Leu Pro Gly Thr Ala Pro Lys Leu Leu
            35                  40                  45

Ile Tyr Ala Asp Ser Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Asp Ser Leu
                85                  90                  95

Ser Gly Tyr Val Phe Gly Gly Gly Thr Lys Leu Thr Val Leu
            100                 105                 110

<210> SEQ ID NO 37
<211> LENGTH: 110
<212> TYPE: PRT
<213> ORGANISM: Artificial Sequence
<220> FEATURE:
<223> OTHER INFORMATION: Synthetic Sequence

<400> SEQUENCE: 37

Gln Ser Val Leu Thr Gln Pro Pro Ser Ala Ser Gly Thr Pro Gly Gln
1               5                   10                  15

Arg Val Thr Ile Ser Cys Ser Ser Ser Ser Asn Ile Gly Ser Asn
            20                  25                  30

Tyr Val Ser Trp Tyr Gln Gln Leu Pro Gly Thr Ala Pro Lys Leu Leu
            35                  40                  45

Ile Tyr Ser Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Ala Tyr Val Phe Gly Gly Gly Thr Lys Leu Thr Val Leu
            100                 105                 110

<210> SEQ ID NO 38
<211> LENGTH: 110
<212> TYPE: PRT
<213> ORGANISM: Artificial Sequence
<220> FEATURE:
<223> OTHER INFORMATION: Synthetic Sequence

<400> SEQUENCE: 38

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Asn Asn
            20                  25                  30

Thr Val Ser Trp Tyr Gln Gln Leu Pro Gly Thr Ala Pro Lys Leu Leu
        35                  40                  45

Ile Tyr Asp Asn Ser His Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Gly Ser Trp Asp Tyr Ser Leu
                85                  90                  95

Ser Ala Tyr Val Phe Gly Gly Gly Thr Lys Leu Thr Val Leu
            100                 105                 110

<210> SEQ ID NO 39
<211> LENGTH: 110
<212> TYPE: PRT
<213> ORGANISM: Artificial Sequence
<220> FEATURE:
<223> OTHER INFORMATION: Synthetic Sequence

<400> SEQUENCE: 39

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Asp Val Asn Trp Tyr Gln Gln Leu Pro Gly Thr Ala Pro Lys Leu Leu
        35                  40                  45

Ile Tyr Tyr Asp Ser Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Ala Ser Leu
                85                  90                  95

Ser Ala Tyr Val Phe Gly Gly Gly Thr Lys Leu Thr Val Leu
            100                 105                 110

<210> SEQ ID NO 40
<211> LENGTH: 110
<212> TYPE: PRT
<213> ORGANISM: Artificial Sequence
<220> FEATURE:
<223> OTHER INFORMATION: Synthetic Sequence

<400> SEQUENCE: 40

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ala Val Asn Trp Tyr Gln Gln Leu Pro Gly Thr Ala Pro Lys Leu Leu
        35                  40                  45

Ile Tyr Tyr Asp Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Asp Ser Leu
                85                  90                  95

Asn Gly Tyr Val Phe Gly Gly Gly Thr Lys Leu Thr Val Leu
            100                 105                 110

<210> SEQ ID NO 41
<211> LENGTH: 110
<212> TYPE: PRT
<213> ORGANISM: Artificial Sequence
<220> FEATURE:
<223> OTHER INFORMATION: Synthetic Sequence

<400> SEQUENCE: 41

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Ala Val Thr Trp Tyr Gln Gln Leu Pro Gly Thr Ala Pro Lys Leu Leu
        35                  40                  45

Ile Tyr Asp Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Ala Tyr Val Phe Gly Gly Gly Thr Lys Leu Thr Val Leu
                100                 105                 110

<210> SEQ ID NO 42
<211> LENGTH: 110
<212> TYPE: PRT
<213> ORGANISM: Artificial Sequence
<220> FEATURE:
<223> OTHER INFORMATION: Synthetic Sequence

<400> SEQUENCE: 42

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Phe Asn Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
                100                 105                 110

<210> SEQ ID NO 43
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 43

Ser Gly Ser Ser Ser Asn Ile Gly Asn Asn Tyr Val Asn
1               5                   10

<210> SEQ ID NO 44
<211> LENGTH: 13

```
<212> TYPE: PRT
<213> ORGANISM: Artificial Sequence
<220> FEATURE:
<223> OTHER INFORMATION: Synthetic Sequence

<400> SEQUENCE: 44

Ser Gly Ser Ser Ser Asn Ile Gly Asn Asn Val Ser
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 45

Thr Gly Ser Ser Ser Asn Ile Gly Ser Asn Ser Val Asn
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 46

Thr Gly Ser Ser Ser Asn Ile Gly Ser Asn Ser Val Asn
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 47

Ser Ser Ser Ser Ser Asn Ile Gly Ser Asn Tyr Val Ser
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 48

Thr Gly Ser Ser Ser Asn Ile Gly Asn Asn Thr Val Ser
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 49

Thr Gly Ser Ser Ser Asn Ile Gly Asn Asn Asp Val Asn
1               5                   10

<210> SEQ ID NO 50
<211> LENGTH: 13
<212> TYPE: PRT
```

```
<213> ORGANISM: Artificial Sequence
<220> FEATURE:
<223> OTHER INFORMATION: Synthetic Sequence

<400> SEQUENCE: 50

Ser Gly Ser Ser Ser Asn Ile Gly Ser Asn Ala Val Asn
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 51

Ser Gly Ser Ser Ser Asn Ile Gly Asn Asn Ala Val Thr
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 52

Ser Gly Ser Ser Ser Asn Ile Gly Ser Asn Thr Phe Asn
1               5                   10

<210> SEQ ID NO 53
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 53

Asp Asn Ser His Arg Pro Ser
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 54

Ala Asn Ser Lys Arg Pro Ser
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 55

Asp Asp Ser His Arg Pro Ser
1               5

<210> SEQ ID NO 56
<211> LENGTH: 7
<212> TYPE: PRT
<213> ORGANISM: Artificial Sequence
```

```
<220> FEATURE:
<223> OTHER INFORMATION: Synthetic Sequence

<400> SEQUENCE: 56

Ala Asp Ser Gln Arg Pro Ser
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 57

Ser Asp Ser His Arg Pro Ser
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 58

Tyr Asp Ser Gln Arg Pro Ser
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 59

Tyr Asp Asn Gln Arg Pro Ser
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 60

Ala Asp Ser His Arg Pro Ser
1               5

<210> SEQ ID NO 61
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 61

Gly Thr Trp Asp Ala Ser Leu Ser Ala Tyr Val
1               5                   10

<210> SEQ ID NO 62
<211> LENGTH: 11
<212> TYPE: PRT
<213> ORGANISM: Artificial Sequence
<220> FEATURE:
```

```
<223> OTHER INFORMATION: Synthetic Sequence

<400> SEQUENCE: 62

Gly Ser Trp Asp Asp Ser Leu Ser Ala Tyr Val
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 63

Asp Ala Trp Asp Ser Ser Leu Ser Ala Tyr Val
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 64

Gly Thr Trp Asp Asp Ser Leu Ser Gly Tyr Val
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 65

Gly Ser Trp Asp Tyr Ser Leu Ser Ala Tyr Val
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 66

Ala Thr Trp Asp Ala Ser Leu Ser Ala Tyr Val
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 67

Gly Thr Trp Asp Asp Ser Leu Asn Gly Tyr Val
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Synthetic Sequence
```

<400> SEQUENCE: 68

Gly Thr Trp Asp Tyr Ser Leu Ser Gly Tyr Val
1               5                   10

<210> SEQ ID NO 69
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Thr Ser Ser Gly Arg Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val His Arg Ala Phe Asp Tyr Trp Gly Gln Gly Thr Leu Val
            100                 105                 110

Thr Val Ser Ser
        115

<210> SEQ ID NO 70
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Thr Ser Ser Gly Ala Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val His Arg Ala Phe Asp Tyr Trp Gly Gln Gly Thr Leu Val
            100                 105                 110

Thr Val Ser Ser
        115

<210> SEQ ID NO 71
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Thr Ser Ser Gly Gly Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val His Arg Ala Phe Asp Tyr Trp Gly Gln Gly Thr Leu Val
            100                 105                 110

Thr Val Ser Ser
        115

<210> SEQ ID NO 72
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Thr Ala Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val His Arg Ala Phe Asp Tyr Trp Gly Gln Gly Thr Leu Val
            100                 105                 110

Thr Val Ser Ser
        115

<210> SEQ ID NO 73
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 73

Ala Ile Thr Ser Ser Gly Arg Ser Ile Tyr Tyr Ala Asp Ser Val Lys
1               5                   10                  15

Gly

```
<210> SEQ ID NO 74
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 74

Ala Ile Thr Ser Ser Gly Ala Asn Ile Tyr Tyr Ala Asp Ser Val Lys
1               5                   10                  15
Gly

<210> SEQ ID NO 75
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 75

Ala Ile Thr Ser Ser Gly Gly Asn Ile Tyr Tyr Ala Asp Ser Val Lys
1               5                   10                  15
Gly

<210> SEQ ID NO 76
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 76

Ala Ile Thr Ala Gly Gly Gly Ser Ile Tyr Tyr Ala Asp Ser Val Lys
1               5                   10                  15
Gly

<210> SEQ ID NO 77
<211> LENGTH: 110
<212> TYPE: PRT
<213> ORGANISM: Artificial Sequence
<220> FEATURE:
<223> OTHER INFORMATION: Synthetic Sequence

<400> SEQUENCE: 77

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Phe Asn Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
                100                 105                 110

<210> SEQ ID NO 78
<211> LENGTH: 110
<212> TYPE: PRT
```

<213> ORGANISM: Artificial Sequence
<220> FEATURE:
<223> OTHER INFORMATION: Synthetic Sequence

<400> SEQUENCE: 78

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Phe Asn Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Arg Gly Tyr Val Leu Gly Gly Gly Thr Lys Leu Thr Val Leu
            100                 105                 110

<210> SEQ ID NO 79
<211> LENGTH: 110
<212> TYPE: PRT
<213> ORGANISM: Artificial Sequence
<220> FEATURE:
<223> OTHER INFORMATION: Synthetic Sequence

<400> SEQUENCE: 79

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Phe Asn Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Tyr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 80
<211> LENGTH: 110
<212> TYPE: PRT
<213> ORGANISM: Artificial Sequence
<220> FEATURE:
<223> OTHER INFORMATION: Synthetic Sequence

<400> SEQUENCE: 80

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Phe Asn Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

```
Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
                100                 105                 110
```

<210> SEQ ID NO 81
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 81

```
Gly Thr Trp Asp Tyr Ser Leu Arg Gly Tyr Val
1               5                   10
```

<210> SEQ ID NO 82
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 82

```
Gly Tyr Trp Asp Tyr Ser Leu Ser Gly Tyr Val
1               5                   10
```

<210> SEQ ID NO 83
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 83

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg His
                20                  25                  30

Ala Met Ala Trp Val Arg Gln Ala Pro Gly Lys Gly Leu Glu Trp Val
            35                  40                  45

Ser Ala Ile Thr Ser Ser Gly Arg Ser Ile Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val His Arg Ala Phe Asp Tyr Trp Gly Gln Gly Thr Leu Val
                100                 105                 110

Thr Val Ser Ser
        115
```

<210> SEQ ID NO 84
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 84

```
Arg His Ala Met Ala
1               5

<210> SEQ ID NO 85
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 85

Ala Ile Thr Ser Ser Gly Arg Ser Ile Tyr Tyr Ala Asp Ser Val Lys
1               5                   10                  15

Gly

<210> SEQ ID NO 86
<211> LENGTH: 111
<212> TYPE: PRT
<213> ORGANISM: Artificial Sequence
<220> FEATURE:
<223> OTHER INFORMATION: Synthetic Sequence

<400> SEQUENCE: 86

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ala Asn Ser Arg Thr Asp
            20                  25                  30

Gly Phe Asn Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu Gly
            100                 105                 110

<210> SEQ ID NO 87
<211> LENGTH: 111
<212> TYPE: PRT
<213> ORGANISM: Artificial Sequence
<220> FEATURE:
<223> OTHER INFORMATION: Synthetic Sequence

<400> SEQUENCE: 87

Gln Ser Val Leu Thr Gln Pro Pro Ser Ala Ser Gly Thr Pro Gly Gln
1               5                   10                  15

Arg Val Thr Ile Ser Cys Ser Gly Ser Ala Gln Phe Gly Ser Arg Asp
            20                  25                  30

Asn Phe Asn Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu Gly
```

<210> SEQ ID NO 88
<211> LENGTH: 111
<212> TYPE: PRT
<213> ORGANISM: Artificial Sequence
<220> FEATURE:
<223> OTHER INFORMATION: Synthetic Sequence

<400> SEQUENCE: 88

Gln Ser Val Leu Thr Gln Pro Pro Ser Ala Ser Gly Thr Pro Gly Gln
1               5                   10                  15

Arg Val Thr Ile Ser Cys Ser Gly Ser Thr Lys Gln Met His Asn Tyr
            20                  25                  30

Gln Phe Asn Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu Gly
            100                 105                 110

<210> SEQ ID NO 89
<211> LENGTH: 111
<212> TYPE: PRT
<213> ORGANISM: Artificial Sequence
<220> FEATURE:
<223> OTHER INFORMATION: Synthetic Sequence

<400> SEQUENCE: 89

Gln Ser Val Leu Thr Gln Pro Pro Ser Ala Ser Gly Thr Pro Gly Gln
1               5                   10                  15

Arg Val Thr Ile Ser Cys Ser Gly Ser Leu Leu Arg Gly Glu Asn Leu
            20                  25                  30

Gln Phe Asn Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu Gly
            100                 105                 110

<210> SEQ ID NO 90
<211> LENGTH: 111
<212> TYPE: PRT
<213> ORGANISM: Artificial Sequence
<220> FEATURE:
<223> OTHER INFORMATION: Synthetic Sequence

<400> SEQUENCE: 90

Gln Ser Val Leu Thr Gln Pro Pro Ser Ala Ser Gly Thr Pro Gly Gln
1               5                   10                  15

Arg Val Thr Ile Ser Cys Ser Gly Ser Pro Leu Phe Pro Asp Ser Gly
            20                  25                  30

```
Ser Phe Asn Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Thr Trp Asp Tyr Ser Leu
                 85                  90                  95

Ser Gly Tyr Val Leu Gly Gly Gly Thr Lys Leu Thr Val Leu Gly
                100                 105                 110

<210> SEQ ID NO 91
<211> LENGTH: 110
<212> TYPE: PRT
<213> ORGANISM: Artificial Sequence
<220> FEATURE:
<223> OTHER INFORMATION: Synthetic Sequence

<400> SEQUENCE: 91

Ser Val Leu Thr Gln Pro Pro Ser Ala Ser Gly Thr Pro Gly Gln Arg
 1               5                  10                  15

Val Thr Ile Ser Cys Ser Gly Ser Ala Ala Leu Asp Leu Ser Pro Ser
                20                  25                  30

Phe Asn Trp Tyr Gln Gln Leu Pro Gly Thr Ala Pro Lys Leu Leu Ile
            35                  40                  45

Tyr Ala Asp Ser His Arg Pro Ser Gly Val Pro Asp Arg Phe Ser Gly
 50                  55                  60

Ser Lys Ser Gly Thr Ser Ala Ser Leu Ala Ile Ser Gly Leu Arg Ser
 65                  70                  75                  80

Glu Asp Glu Ala Asp Tyr Tyr Cys Gly Thr Trp Asp Tyr Ser Leu Ser
                 85                  90                  95

Gly Tyr Val Leu Gly Gly Gly Thr Lys Leu Thr Val Leu Gly
                100                 105                 110

<210> SEQ ID NO 92
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 92

Ser Gly Ser Ser Ala Asn Ser Arg Thr Asp Gly Phe Asn
 1               5                  10

<210> SEQ ID NO 93
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 93

Ser Gly Ser Ala Gln Phe Gly Ser Arg Asp Asn Phe Asn
 1               5                  10

<210> SEQ ID NO 94
<211> LENGTH: 13
<212> TYPE: PRT
<213> ORGANISM: Artificial Sequence
<220> FEATURE:
```

<223> OTHER INFORMATION: Synthetic Sequence

<400> SEQUENCE: 94

Ser Gly Ser Thr Lys Gln Met His Asn Tyr Gln Phe Asn
1               5                   10

<210> SEQ ID NO 95
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 95

Ser Gly Ser Leu Leu Arg Gly Glu Asn Leu Gln Phe Asn
1               5                   10

<210> SEQ ID NO 96
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 96

Ser Gly Ser Pro Leu Phe Pro Asp Ser Gly Ser Phe Asn
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 97

Ser Gly Ser Ala Ala Leu Asp Leu Ser Pro Ser Phe Asn
1               5                   10

<210> SEQ ID NO 98
<211> LENGTH: 232
<212> TYPE: PRT
<213> ORGANISM: Artificial Sequence
<220> FEATURE:
<223> OTHER INFORMATION: Synthetic Sequence

<400> SEQUENCE: 98

Met Gly Trp Leu Cys Ser Gly Leu Leu Phe Pro Val Ser Cys Leu Val
1               5                   10                  15

Leu Leu Gln Val Ala Ser Ser Gly Asn Met Lys Val Leu Gln Glu Pro
                20                  25                  30

Thr Cys Val Ser Asp Tyr Met Ser Ile Ser Thr Cys Glu Trp Lys Met
            35                  40                  45

Asn Gly Pro Thr Asn Cys Ser Thr Glu Leu Arg Leu Leu Tyr Gln Leu
        50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
                100                 105                 110

Gly Ser Phe Lys Pro Ser Glu His Val Lys Pro Arg Ala Pro Gly Asn
            115                 120                 125

```
Leu Thr Val His Thr Asn Val Ser Asp Thr Leu Leu Leu Thr Trp Ser
    130             135             140

Asn Pro Tyr Pro Pro Asp Asn Tyr Leu Tyr Asn His Leu Thr Tyr Ala
145             150             155             160

Val Asn Ile Trp Ser Glu Asn Asp Pro Ala Asp Phe Arg Ile Tyr Asn
                165             170             175

Val Thr Tyr Leu Glu Pro Ser Leu Arg Ile Ala Ala Ser Thr Leu Lys
            180             185             190

Ser Gly Ile Ser Tyr Arg Ala Arg Val Arg Ala Trp Ala Gln Cys Tyr
        195             200             205

Asn Thr Thr Trp Ser Glu Trp Ser Pro Ser Thr Lys Trp His Asn Ser
    210             215             220

Tyr Arg Glu Pro Phe Glu Gln His
225             230
```

HUMAN ANTIBODY HAVING HIGH AFFINITY TO HUMAN IL-4 RECEPTOR ALPHA

CROSS-REFERENCE TO RELATED APPLICATIONS

This application is a national stage of international application no. PCT/KR2019/015083 filed Nov. 7, 2019, which claims priority from Korean patent application no. 10-2018-0137199 filed on Nov. 9, 2018.

SEQUENCE LISTING

The content of the electronically submitted sequence listing, file name: Sequence_Listing_As_Filed.txt; size: 53,551 bytes; and date of creation: Feb. 3, 2021, filed herewith, is incorporated herein by reference in its entirety.

TECHNICAL FIELD

The present invention relates to an isolated antibody or antigen-binding fragment thereof that binds with high affinity to human IL-4 receptor alpha (hIL-4Rα), which is a receptor for human IL-4 (hIL-4), a nucleic acid encoding the same, a vector including the nucleic acid, a cell transformed with the vector, a method for producing the antibody or antigen-binding fragment thereof, a conjugate containing the same, a composition for preventing or treating inflammatory diseases containing the same, and a composition for diagnosing inflammatory diseases containing the same.

BACKGROUND ART

Allergic diseases such as atopic dermatitis, allergic rhinitis, asthma and food allergies are involved in aggravated Th2 cell responses to innocuous environmental antigens (allergens).

Allergens are captured by antigen-presenting cells, migrate to lymph nodes, and act on naive T-helper cells (Th0) in the lymph nodes to induce differentiation of Th0 cells by IL4. Allergen-specific Th cells belong to the Th2 phenotype and are differentiated from precursor T cells by interleukin-4 (IL-4) to develop into Th2 cells. Once activated, Th2 cells secrete interleukin-4 (IL-4) and interleukin-13 (IL-13), which, together with a signal bound to the surface thereof, induce B cells to convert into IgE-producing plasma cells. The IgE molecule binds to high-affinity FcεR in mast cells and then encounters the allergen to thereby induce activation of mast cells and induce the release of mediators of allergic reactions. Th2 cytokines also promote the survival of eosinophils and promote the growth of mast cells, which release additional Th2 cytokines that can enhance IgE production, Th2 cell differentiation and eosinophil survival after degranulation.

Therefore, Th2 cells play a pivotal role in the induction and development of allergic reactions. Thus, neutralizing and inhibiting the action of Th2 cytokines (e.g., IL-4 and IL-13) to suppress the development thereof and/or the action of effectors thereof is expected to be an effective way to mediate allergic reactions.

IL-4-specific drugs, namely altrakincept (Immunex) and pascolizumab (GlaxoSmithKline), exhibited effects of partial relief of asthma symptoms, but were abandoned in early clinical stages. Although drugs for IL-13 were expected to have more potent therapeutic effects than drugs for IL-4, anrukinzumab (Pfizer; Wyeth) failed in clinical phase 2, Tralokinumab (AstraZeneca) failed in clinical phase 3, and Lebrikizumab (Roche, Dermira) is undergoing clinical trials in phase 2. Single drugs for inhibiting IL-4 or IL-13 that have been developed to date do not exhibit great effects in clinical practice due to the overlapping roles of the two cytokines.

Thus, it has been suggested that inhibiting the action of both cytokines, namely IL-4 and IL-13, may be more beneficial than targeting IL-4 or IL-13 alone. Specifically, cell surface receptors and receptor complexes bind to IL-4 and/or IL-13 with different affinities. IL-4 binds to IL-4Rα with high affinity (1 nM) to form a heterodimer with IL-13Rα1, whereas IL-13 binds to IL-13Rα1 with high affinity (30 nM) to form a heterodimer with IL-4Rα and thereby transmit cell signaling by Stat6. Thus, research has been conducted on strategies to target receptors thereof.

In the case of the IL-4 mutein (Pitrakinra; Aerovance, Berkeley, CA), a receptor complex cannot be formed even when binding to IL-4Rα by introducing a mutation at the binding site with IL-13Rα, so in clinical phase 2a, the effect of reducing allergen-induced late-stage asthma reactions and the effect of relieving inflammation of the lungs of asthma patients at a resting stage are shown due to signal inhibition ability by IL-4 and IL-13. This further supported the view on the targeting of IL-4Rα. However, the PK (Pharmacokinetics) characteristics did not meet expectations due to the short half-life thereof.

Another IL-4/IL-13 inhibitor, AMG317 (Amgen), binds to IL-4Rα and inhibits the activity of IL4 and IL13. However, when AMG317 was administered to placebo and severe atopic asthma patients for 12 weeks, it showed low effectiveness, and phase 2 clinical trials thereof failed.

Regarding anti-hIL-4Rα antibodies developed to date, dupilumab, which was developed by Regeneron Pharmaceuticals Inc. (U.S. Pat. No. 7,605,237, Korean Patent No. 10-1474227) and was approved by the FDA in 2017, is used for the treatment of allergic diseases (e.g., atopic eczema disease). Dupilumab is an anti-hIL-4Rα antibody with a very high affinity (equilibrium dissociation constant ($K_D$) at the pM level).

However, anti-hIL-4Rα therapeutic antibodies other than dupilumab have not yet been approved, and resistance to therapeutic drugs, such as anti-drug antibodies (ADA), may develop upon continuous and repeated administration of the same therapeutic drug (Vaisman-Mentesh, A. et al., 2019). Accordingly, there is still high demand for technology for anti-hIL-4Rα antibodies having potent therapeutic effects.

In addition, IL-4Rα can induce endocytosis (receptor-mediated endocytosis) of substances that bind to receptors due to the property of rapid cellular internalization thereof to degrade the substances. This property provides an opportunity for rapid antigen-mediated clearance of antibodies, which are administered to the body and bind to IL-4Rα (Fujimoto et al., 2015). This case can be facilitated when the affinity of the antibody is high, especially when detachment does not occur after binding to the receptor due to low dissociation rate constant (off-rate constant) with the antigen (M Ritchie et al., 2013).

Against this technical background, based on the necessity to develop a novel anti-hIL-4Rα antibody capable of inhibiting both IL-4 and IL-13 signals because the efficacy of antibodies against the same antigen may vary depending on the epitope and affinity, and because, upon continuous and repeated administration of the same therapeutic agent, resistance thereto may arise, the present inventors developed an anti-hIL-4Rα antibody having high affinity corresponding to a high equilibrium dissociation constant ($K_D$) at a pM level and an epitope different from that of a conventional antibody. Based on this finding, the present invention has been completed.

DISCLOSURE

Technical Problem

Therefore, the present invention has been made in view of the above problems, and it is one object of the present invention to provide a novel antibody or antigen-binding fragment thereof having a pM level of affinity ($K_D$) for hIL-4Rα.

It is another object of the present invention to provide a novel antibody or antigen-binding fragment thereof having an epitope different from a conventional antibody for hIL-4Rα.

It is another object of the present invention to provide a novel antibody or antigen-binding fragment thereof having an increased antigen dissociation rate (off-rate) for hIL-4Rα.

It is another object of the present invention to provide a nucleic acid encoding the antibody or antigen-binding fragment thereof.

It is another object of the present invention to provide a vector containing the nucleic acid, a cell transformed with the vector, and a method for producing the same.

It is another object of the present invention to provide a conjugate including the antibody or antigen-binding fragment thereof.

It is another object of the present invention to provide a pharmaceutical composition for preventing or treating inflammatory diseases containing the antibody or antigen-binding fragment thereof.

It is another object of the present invention to provide a composition for diagnosing inflammatory diseases containing the antibody or antigen-binding fragment thereof.

Technical Solution

In accordance with one aspect of the present invention, the above and other objects can be accomplished by the provision of an antibody or antigen-binding fragment thereof having an equilibrium dissociation constant ($K_D$) of less than 150 pM for human interleukin-4 receptor alpha (hIL-4Rα), as measured by surface plasmon resonance (SPR), and an antigen-binding site different from that of a conventional antibody.

In particular, the antibody according to the present invention binds to an epitope including amino acid residues of Leu67, Leu68, Asp92, Val93 and Asp97 of human interleukin-4 receptor alpha (hIL-4Rα), represented by SEQ ID NO: 98, and binds to hIL-4Rα competitively with human interleukin-4 (hIL-4) and human interleukin-13 (hIL-13).

The antibody according to the present invention is an isolated antibody or antigen-binding fragment thereof binding to human interleukin-4 receptor alpha (hIL-4Rα), and is expected to have an antigen dissociation rate (off-rate) that is faster than that of previously developed antibodies, to thereby decrease the antigen-mediated antibody clearance in vivo.

In accordance with another aspect of the present invention, provided is a nucleic acid encoding the antibody or antigen-binding fragment thereof.

In accordance with another aspect of the present invention, provided is a vector containing the nucleic acid.

In accordance with another aspect of the present invention, provided is a cell transformed with the vector.

In accordance with another aspect of the present invention, provided is a method for producing an antibody or antigen-binding fragment thereof, the method including (a) culturing the cell and (b) collecting an antibody or antigen-binding fragment thereof from the cell.

In accordance with another aspect of the present invention, provided is a conjugate in which the antibody or antigen-binding fragment thereof is fused with a bioactive molecule selected from the group consisting of peptides, proteins, small-molecule drugs, nucleic acids, nanoparticles, and liposomes.

In accordance with another aspect of the present invention, provided is a pharmaceutical composition for preventing or treating inflammatory diseases containing the antibody or antigen-binding fragment thereof.

In accordance with another aspect of the present invention, provided is a composition for diagnosing inflammatory diseases containing the antibody or antigen-binding fragment thereof.

DESCRIPTION OF DRAWINGS

FIG. 1A is a schematic diagram showing a recombinant expression vector for expressing a hIL-4Rα antigen protein, wherein Pcmv is a promoter and H is a Poly 6×Histidine Tag.

FIG. 1B shows the results of SDS-PAGE confirming the hIL-4Rα antigen protein expressed in HEK293F cells.

FIG. 2 shows the results of indirect ELISA confirming the binding affinity and specific binding of anti-hIL-4Rα antibodies to hIL-4Rα antigen protein.

FIG. 3A is a schematic diagram showing the enzyme-substrate response and secretion mechanism of secreted embryonic alkaline phosphatase (SEAP) by hIL-4-dependent STAT6 phosphorylation of HEK-blue cells.

FIG. 3B shows the degree of SEAP activity by hIL-4-dependent STAT6 phosphorylation using HEK-Blue-IL-4/IL-13 cells of anti-hIL-4Rα antibodies.

FIG. 4 is a schematic diagram showing the construction strategy of a library constructed based on 4R34 to improve the affinity of the anti-hIL-4Rα antibody, wherein the library is constructed in CDR2 and CDR3 of the heavy-chain variable region and CDR3 of the light-chain variable region.

FIG. 5 is a schematic diagram showing a strategy for selection of a library constructed based on 4R34 to improve the affinity of an anti-hIL-4Rα antibody.

FIG. 6 shows data analyzed by flow cytometry regarding a stepwise selection process for obtaining a clone with high affinity for hIL-4Rα in the library constructed based on 4R34.

FIG. 7A is a schematic diagram showing an animal cell expression vector for expressing the hIL-4-mFc ligand protein.

FIG. 7B shows the results of SDS-PAGE confirming the hIL-4-mFc ligand protein expressed in HEK293F cells.

FIG. 8 shows data analyzed by flow cytometry regarding the binding ability of yeast surface-expressing scFab clones to hIL-4Rα under competition conditions with hIL-4-mFc, which demonstrates that yeast surface-expressing scFab clones bind to a binding site similar to hIL-4.

FIG. 9 shows the degree of SEAP activity by hIL-4 dependent STAT6 phosphorylation using HEK-Blue-IL-4/IL-13 cells of anti-hIL-4Rα antibodies having improved affinity.

FIG. 10 is a schematic diagram showing a strategy for constructing a library constructed based on 4R34.1 to improve the affinity of an anti-hIL-4Rα antibody, wherein the library was constructed in the CDR1 of the heavy-chain variable region and the CDR1 of the light-chain variable region.

FIG. 11 shows the result of binding competition ELISA of selected anti-hIL-4Rα antibodies and hIL-4-mFc ligand to hIL-4Rα, wherein binding competition with hIL-4-mFc was confirmed depending on the concentration of the antibodies, which demonstrates that the anti-hIL-4Rα antibodies bind to the region overlapping the hIL-4-binding site.

FIG. 12 shows the degree of SEAP activity by hIL-4-dependent STAT6 phosphorylation using HEK-Blue-IL-4/IL-13 cells of anti-hIL-4Rα antibodies.

FIG. 13 shows the degree of SEAP activity by hIL-13-dependent STAT6 phosphorylation using HEK-Blue-IL-4/IL-13 cells of anti-hIL-4Rα antibodies.

FIG. 14 shows the hIL-4Rα-specific binding ability of anti-hIL-4Rα antibodies in the THP-1 cell line expressing hIL-4Rα and the Molt-4 cell line not expressing hIL-4Rα, analyzed at different antibody concentrations by flow cytometry.

FIG. 15A is a detailed view showing the binding structure of hIL-4 and hIL-4Rα (PDB ID: 1IAR) and residues that are important for the binding, wherein the residues Glu33 and Arg112 are the residues of hIL-4 that play an important role for binding to hIL-4Rα, the residues Tyr38, Ser95, Asp97 and Tyr208 are the residues of hIL-4Rα that play an important role for binding to hIL-4, and the residues Leu67, Leu68, Asp92, and Val93 are expected to be involved in binding to hIL-4, and are epitope regions of antibodies developed by Medimmune Limited.

FIG. 15B shows the result of 12% SDS-PAGE under non-reducing conditions regarding hIL-4Rα variants constructed, expressed, and purified by introducing an alanine mutation into each of the hIL-4Rα residues shown in FIG. 10A.

FIG. 15C shows the result of a test confirming the epitope region of each antibody through indirect ELISA of anti-hIL-4Rα antibodies and hIL-4Rα variants purified in FIG. 10A, wherein dupilumab analogues exhibited lower binding ability than hIL-4Rα variants having a single alanine mutation at the Val93 or Asp97 residue, and different anti-hIL-4Rα antibodies exhibited different binding ability to the hIL-4Rα variants, which indicates that the epitope regions of the antibodies changed through the affinity maturation process.

FIG. 16 shows the ability of anti-hIL-4Rα antibodies to inhibit cell growth in normal subject- and patient-derived PHA-activated PBMCs.

FIG. 17A shows the quantitative values of the ability of the anti-hIL-4Rα antibodies to inhibit differentiation of normal subject- and patient-derived naive T cells to Th2 cells.

FIG. 17B is a representative image showing the results of a test confirming the ability of the anti-hIL-4Rα antibodies to inhibit differentiation from normal subject- and patient-derived naive T cells to Th2 cells.

BEST MODE

Unless defined otherwise, all technical and scientific terms used herein have the same meanings as appreciated by those skilled in the field to which the present invention pertains. In general, the nomenclature used herein is well-known in the art and is ordinarily used.

In one aspect, the present invention is directed to an isolated antibody or antigen-binding fragment thereof binding to human interleukin-4 receptor alpha (hIL-4Rα), the isolated antibody or antigen-binding fragment thereof having an equilibrium dissociation constant ($K_D$) of less than 150 pM, as measured by surface plasmon resonance (SPR), but having a higher off-rate than a previously developed antibody, so that a phenomenon in which the antibody is removed by the antigen in vivo (called "antigen-mediated clearance") is expected to decrease, thereby improving in-vivo pharmacokinetics.

The antibody according to the present invention is an antibody that binds with high affinity to the antigen hIL-4Rα, and has the ability to neutralize IL-4 activity. The term "affinity" refers to the ability to specifically recognize a specific site of an antigen and to bind thereto, and specificity and high-affinity of an antibody for an antigen are important factors in the immune response.

The equilibrium dissociation constant ($K_D$) can be determined using surface plasmon resonance (SPR), for example, BIAcore instrument. An equilibrium dissociation constant ($K_D$) calculated from a 1:1 Langmuir binding model (simultaneously ka and kd) and the ratio of the rate constant kd1/ka1 was obtained based on surface plasmon resonance data, and may be less than 150 pM, less than 100 pM, less than 75 pM, or less than 50 pM.

In one embodiment, the antibody according to the present invention binds to an epitope including amino acid residues of Leu67, Leu68, Asp92, Val93 and Asp97 in hIL-4Rα of SEQ ID NO: 98, and can bind to hIL-4Rα competitively with human interleukin-13 (hIL-13) and human interleukin-4 (hIL-4).

As used herein, the term "antibody" refers to an anti-hIL-4Rα antibody that specifically binds to hIL-4Rα. The scope of the present invention includes not only a complete antibody specifically binding to hIL-4Rα but also an antigen-binding fragment of the antibody molecule.

The complete antibody has a structure having two full-length light chains and two full-length heavy chains, wherein each light chain is linked to a corresponding heavy chain by a disulfide bond. The heavy-chain constant region has gamma (γ), mu (μ), alpha (α), delta (δ) and epsilon (ε) types, and is subclassified into gamma 1 (γ1), gamma 2 (γ2), gamma 3 (γ3), gamma 4 (γ4), alpha 1 (α1), and alpha 2 (α2). The light-chain constant region has kappa (κ) and lambda (λ) types.

The antigen-binding fragment of an antibody or antibody fragment refers to a fragment that has antigen-binding function and includes Fab, F(ab'), F(ab')2, Fv and the like. Among the antibody fragments, Fab refers to a structure including a variable region of each of the heavy chain and the light chain, the constant region of the light chain, and the first constant domain (CH1) of the heavy chain, each having one antigen-binding site. "scFab" is a polypeptide consisting of the light-chain and heavy-chain variable regions, the light-chain constant region, the first heavy-chain constant region (CH1), and a linker. In some cases, it may be stabilized by insertion of cysteine residues. Fab' is different from Fab in that it further includes a hinge region including at least one cysteine residue at the C-terminus of the CH1 domain of the heavy chain. F(ab')2 is created by a disulfide bond between cysteine residues in the hinge region of Fab'.

Fv is the minimal antibody fragment having only a heavy-chain variable region and a light-chain variable region. Two-chain Fv is a fragment in which the variable region of the heavy chain and the variable region of the light chain are linked by a non-covalent bond, and single-chain Fv (scFv) is a fragment in which the variable region of the heavy chain and the variable region of the light chain are generally linked by a covalent bond via a peptide linker therebetween, or are directly linked at the C-terminal, forming a dimer-shaped structure, like the two-chain Fv. Such antibody fragments may be obtained using proteases (e.g., Fab can be obtained by restriction-cleaving the complete antibody with papain, and the F(ab')2 fragment can be obtained by restriction-cleaving the complete antibody with pepsin), and may be produced using genetic recombination techniques.

In one embodiment, the antibody of the present invention is in an Fv form (for example, scFv) or a complete antibody form. In addition, the heavy-chain constant region may be selected from gamma (γ), mu (μ), alpha (α), delta (δ) and epsilon (ε) isotypes. For example, the constant region may be gamma 1 (IgG1), gamma 3 (IgG3) or gamma 4 (IgG4). The light-chain constant region may be kappa or lambda.

As used herein, the term "heavy chain" encompasses both a full-length heavy chain, which includes a variable domain (VH) containing an amino acid sequence having a variable region sequence sufficient for imparting specificity to an antigen and three constant domains (CH1, CH2 and CH3), and a fragment thereof. As used herein, the term "light chain" encompasses both a full-length light chain, which includes a variable domain (VL) containing an amino acid sequence having a variable region sequence sufficient for imparting specificity to an antigen and a constant domain (CL), and a fragment thereof.

The antibody of the present invention includes, but is not limited to, monoclonal antibodies, multispecific antibodies, human antibodies, humanized antibodies, chimeric antibodies, scFvs, single-chain antibodies, Fab fragments, F(ab') fragments, disulfide-bond Fvs (sdFvs), anti-idiotypic (anti-Id) antibodies, epitope-binding fragments of such antibodies, and the like.

The term "monoclonal antibody" refers to a uniform antibody, which is obtained from a population of substantially homogeneous antibodies, that is, each antibody constituting the population, excluding possible naturally occurring mutations that may be present in trivial amounts. Monoclonal antibodies are highly specific and are thus induced against a single antigenic site. Unlike conventional (polyclonal) antibody preparations that typically include different antibodies directed against different determinants (epitopes), each monoclonal antibody is directed against a single determinant on the antigen.

For example, monoclonal antibodies useful in the present invention may be produced by hybridoma methods, or may be produced in bacterial, eukaryotic or plant cells using recombinant DNA methods. In addition, monoclonal antibodies may be isolated from phage antibody libraries.

In one embodiment of the present invention, a library may be constructed to improve the affinity of the CDR region of an antibody that specifically binds to hIL-4Rα, and may be realized by a method including (1) selecting an amino acid site having a high possibility of binding to hIL-4Rα, among six complementary binding sites (CDRs) involved in antigen-binding of 4R34 and 4R34.1 light-chain variable regions (VL) and heavy-chain variable regions (VH) as library templates, (2) designing a degenerated codon primer and a spiked oligonucleotide capable of encoding an amino acid to be included in the library at the selected amino acid site, and (3) expressing the designed heavy-chain variable region library in the form of scFab or Fab using a yeast surface expression system.

In one embodiment of the present invention, the antibody scFab that specifically binds to hIL-4Rα may be isolated and/or screened using a library to improve affinity.

The method for screening the antibody that specifically binds to hIL-4Rα according to the present invention may be carried out by a method including:
(1) expressing an antibody scFab library capable of binding to hIL-4Rα using a yeast surface expression system;
(2) constructing and expressing a IL-4Rα vector fused with a His Tag;
(3) binding hIL-4Rα to the library and selecting the yeast maintaining to bind to hIL-4Rα even after the conditions for dissociating the bound hIL-4Rα are satisfied (Kinetic screening); and
(4) measuring the affinity of the binding between the hIL-4Rα and the library.

As described above, the anti-hIL-4Rα antibody according to the present invention is an antibody binding with high affinity to hIL-4Rα, which is obtained by selecting antibodies to hIL-4Rα from the human antibody Fab library expressed on the yeast cell surface, additionally constructing an antibody Fab library on the yeast surface to improve affinity, and selecting an antibody binding with high affinity to hIL-4Rα through kinetic screening.

Techniques for identifying and separating high-affinity antibodies from libraries are important for the separation of new therapeutic antibodies. The separation of high-affinity antibodies from libraries may depend on the size of the libraries, the production efficiency in bacterial cells, and the variety of libraries. The size of the libraries is reduced by improper folding of the antibody- or antigen-binding protein and inefficient production due to the presence of the stop codon. Expression in bacterial cells can be inhibited when the antibody- or antigen-binding domain is not properly folded. Expression can be improved by alternately mutating residues on the surface of the variable/constant interfaces or the selected CDR residues.

It is important to generate various libraries of antibody- or antigen-binding proteins in the separation of high-affinity antibodies. CDR3 regions have often been found to participate in antigen binding. Since the CDR3 region on the heavy chain varies considerably in terms of size, sequence and structurally dimensional morphology, various libraries can be prepared using the same.

Also, diversity can be created by randomizing the CDR regions of variable heavy and light chains using all 20 amino acids at each position. The use of all 20 amino acids results in antibody sequences having increased diversity and an increased chance of identifying new antibodies.

The term "epitope" refers to a protein determinant to which an antibody is capable of specifically binding. Epitopes usually consist of a group of chemically active surface molecules, such as amino acids or sugar side chains, and generally have not only specific three-dimensional structural characteristics but also specific charge characteristics. Three-dimensional epitopes are distinguished from non-three-dimensional epitopes in that a bond to the former is broken in the presence of a denaturing solvent, while a bond to the latter is not broken.

In an embodiment according to the present invention, the antibody may bind to an epitope including an amino acid residue selected from the group consisting of Leu67, Leu68, Asp92, Val93 and Asp97 in hIL-4Rα of SEQ ID NO: 98.

4R34, 4R34.1 and 4R34.1.9 antibodies derived according to affinity maturation according to an embodiment of the present invention recognize Leu67, Leu68, Asp92, Val93 and Asp97 of hIL-4Rα as important epitopes, but the contribution of each epitope is varied. In particular, the binding ability to Asp92 and Val93 tends to be higher than that of 4R34 or 4R34.1, which indicates that the binding ability is still maintained by other adjacent residues. This suggests that the epitope of antibodies changes during the affinity maturation process. Dupilumab analogues have no significant difference in binding ability to the hIL-4Rα amino acid residue mutant from the wild-type, but Val93 and Asp97 are considered to be involved in weakly binding to antibodies. Consequently, it was confirmed that the antibodies according to the present invention have an epitope different from those of other antibodies including dupilumab analogues.

The non-human (e.g., murine) antibody of the "humanized" form is a chimeric antibody containing a minimal sequence derived from non-human immunoglobulin. In most cases, the humanized antibody is a human immunoglobulin (receptor antibody) in which a residue from the hypervariable region of a receptor is replaced with a residue from the hypervariable region of a non-human species (donor antibody) such as a mouse, rat, rabbit or non-human primate having the desired specificity, affinity and ability.

The term "human antibody" means a molecule derived from human immunoglobulin, wherein all of the amino acid sequences constituting the antibody including a complementarity-determining region and a structural region are composed of human immunoglobulin.

A part of the heavy chain and/or light chain is identical to or homologous with the corresponding sequence in an antibody derived from a particular species or belonging to a particular antibody class or subclass, while the other chain(s) include "chimeric" antibodies (immunoglobulins) which are identical to or homologous with corresponding sequences in an antibody derived from another species or belonging to another antibody class or subclass, as well as fragments of such antibody exhibiting the desired biological activity.

As used herein, the term "antibody variable domain" refers to the light- and heavy-chain regions of an antibody molecule including the amino acid sequences of a complementarity-determining region (CDR; i.e., CDR1, CDR2, and CDR3) and a framework region (FR). VH refers to a variable domain of the heavy chain. VL refers to a variable domain of the light chain.

The term "complementarity-determining region" (CDR; i.e., CDR1, CDR2, and CDR3) refers to an amino acid residue of the antibody variable domain that is necessary for antigen binding. Each variable domain typically has three CDR regions, identified as CDR1, CDR2, and CDR3.

In the present invention, the antibody or antigen-binding fragment thereof binding to hIL-4Rα may include a heavy-chain CDR1 of SEQ ID NOs: 11 to 13 or 84, a heavy-chain CDR2 selected from the group consisting of SEQ ID NOs: 14 to 22, 73 to 76, and 85, and a heavy-chain CDR3 selected from the group consisting of SEQ ID NOs: 23 to 32, and a light-chain CDR1 selected from the group consisting of SEQ ID NOs: 43 to 52 and 92 to 97, a light-chain CDR2 selected from the group consisting of SEQ ID NOs: 53 to 60, and a light-chain CDR3 selected from the group consisting of SEQ ID NOs: 61 to 68, 81, and 82.

Specifically, the antibody or antigen-binding fragment thereof may include the heavy-chain and light-chain CDR sequences shown in Tables 1 and 2 below.

TABLE 1

| Heavy-chain variable region name | CDR1 sequence | | | | | CDR2 sequence | | | | | | | | | | | | | | | | | CDR3 sequence | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|
| Kabat No. | 31 | 32 | 33 | 34 | 35 | 50 | 51 | 52 | 52a | 53 | 54 | 55 | 56 | 57 | 58 | 59 | 60 | 61 | 62 | 63 | 64 | 65 | 95 | 96 | 97 | 98 | 99 | 100 | 100a | 100b | 100c | 100d | 100e | 100f | 100g | 100h | 100i | 100j | 101 | 102 |
| 4R14 | N | Y | A | M | S | A | I | S | S | G | G | N | I | Y | Y | A | D | S | V | K | | | G | L | R | R | Y | F | . | . | . | . | . | . | . | . | . | . | D | Y |
| | SEQ ID NO: 11 | | | | | SEQ ID NO: 14 | | | | | | | | | | | | | | | | | SEQ ID NO: 23 | | | | | | | | | | | | | | | | |
| 4R23 | D | Y | A | M | S | A | I | S | S | G | G | S | S | I | Y | Y | A | D | S | V | K | | G | G | P | Q | R | S | A | T | A | V | F | . | . | . | . | . | D | Y |
| | SEQ ID NO: 12 | | | | | SEQ ID NO: 15 | | | | | | | | | | | | | | | | | SEQ ID NO: 24 | | | | | | | | | | | | | | | | |
| 4R25 | N | Y | A | M | S | W | I | S | P | N | S | G | N | I | Y | Y | A | D | S | V | K | | G | R | P | L | S | A | A | W | S | Y | Y | Y | N | A | M | . | D | Y |
| | SEQ ID NO: 11 | | | | | SEQ ID NO: 16 | | | | | | | | | | | | | | | | | SEQ ID NO: 25 | | | | | | | | | | | | | | | | |
| 4R66 | G | Y | A | M | S | L | I | I | S | H | S | G | S | N | T | Y | Y | A | D | S | V | K | G | P | H | R | A | F | . | . | . | . | . | . | . | . | . | . | D | Y |
| | SEQ ID NO: 13 | | | | | SEQ ID NO: 17 | | | | | | | | | | | | | | | | | SEQ ID NO: 26 | | | | | | | | | | | | | | | | |
| 4R67 | N | Y | A | M | S | G | I | S | H | G | S | G | S | I | Y | Y | A | D | S | V | K | | G | T | G | R | D | F | . | . | . | . | . | . | . | . | . | . | D | Y |
| | SEQ ID NO: 11 | | | | | SEQ ID NO: 18 | | | | | | | | | | | | | | | | | SEQ ID NO: 27 | | | | | | | | | | | | | | | | |
| 4R73 | N | Y | A | M | S | G | I | S | H | G | N | G | S | I | Y | Y | A | D | S | V | K | | G | T | G | R | H | F | . | . | . | . | . | . | . | . | . | . | D | Y |
| | SEQ ID NO: 11 | | | | | SEQ ID NO: 19 | | | | | | | | | | | | | | | | | SEQ ID NO: 28 | | | | | | | | | | | | | | | | |
| 4R83 | N | Y | A | M | S | S | I | S | P | S | G | G | S | I | Y | Y | A | D | S | V | K | | G | S | Y | R | A | F | . | . | . | . | . | . | . | . | . | . | D | Y |
| | SEQ ID NO: 11 | | | | | SEQ ID NO: 20 | | | | | | | | | | | | | | | | | SEQ ID NO: 29 | | | | | | | | | | | | | | | | |
| 4R91 | N | Y | A | M | S | A | I | S | P | G | G | G | S | I | Y | Y | A | D | S | V | K | | G | A | K | R | A | F | . | . | . | . | . | . | . | . | . | . | D | Y |
| | SEQ ID NO: 11 | | | | | SEQ ID NO: 21 | | | | | | | | | | | | | | | | | SEQ ID NO: 30 | | | | | | | | | | | | | | | | |
| 4R33 | N | Y | A | M | S | A | I | S | P | G | G | G | T | Y | Y | A | D | S | V | K | | | G | F | R | R | H | F | . | . | . | . | . | . | . | . | . | . | D | Y |
| | SEQ ID NO: 11 | | | | | SEQ ID NO: 22 | | | | | | | | | | | | | | | | | SEQ ID NO: 31 | | | | | | | | | | | | | | | | |
| 4R34 | N | Y | A | M | S | A | I | S | S | G | G | N | I | Y | Y | A | D | S | V | K | | | G | V | H | R | A | F | . | . | . | . | . | . | . | . | . | . | D | Y |
| | SEQ ID NO: 11 | | | | | SEQ ID NO: 14 | | | | | | | | | | | | | | | | | SEQ ID NO: 32 | | | | | | | | | | | | | | | | |

TABLE 1-continued

| Heavy-chain variable region name | CDR1 sequence | | | | | | CDR2 sequence | | | | | | | | | | | | | | | | | CDR3 sequence |
|---|---|---|---|---|---|---|---|---|---|---|---|---|---|---|---|---|---|---|---|---|---|---|---|---|---|
| Kabat No. | 31 | 32 | 33 | 34 | 35 | | 50 | 51 | 52 | 52a | 53 | 54 | 55 | 56 | 57 | 58 | 59 | 60 | 61 | 62 | 63 | 64 | 65 | 65 | 96 97 98 99 100 102 |
| 4R34.1 | N | Y | A | M | S | SEQ ID NO: 11 | A | I | T | | S | G | R | S | I | Y | Y | A | D | S | V | K | | GV H R A F D Y SEQ ID NO: 73 | SEQ ID NO: 32 |
| 4R34.2 | N | Y | A | M | S | SEQ ID NO: 11 | A | I | T | | S | G | A | N | I | Y | Y | A | D | S | V | K | | GV H R A F D Y SEQ ID NO: 74 | SEQ ID NO: 32 |
| 4R34.19 | N | Y | A | M | S | SEQ ID NO: 11 | A | I | T | | S | G | G | N | I | Y | Y | A | D | S | V | K | | GV H R A F D Y SEQ ID NO: 75 | SEQ ID NO: 32 |
| 4R34.29 | N | Y | A | M | S | SEQ ID NO: 11 | A | I | T | | A | G | G | S | I | Y | Y | A | D | S | V | K | | GV H R A F D Y SEQ ID NO: 76 | SEQ ID NO: 32 |
| 4R34.1.19 | R | H | A | M | A | SEQ ID NO: 84 | A | I | T | | S | G | R | S | I | Y | Y | A | D | S | V | K | | GV H R A F D Y SEQ ID NO: 85 | SEQ ID NO: 32 |

TABLE 2

| Light-chain variable region name | CDR1 sequence (24, 25, 26, 27, 27a, 27b, 28, 29, 30, 31, 32, 33) | CDR2 sequence (34, 50, 51, 52, 53, 54, 55) | CDR3 sequence (56, 89, 90, 91, 92, 93, 94, 95, 95a, 95b, 96, 97) |
|---|---|---|---|
| 4R14 | S G S S S N I G N N Y V (SEQ ID NO: 43) | N D N S H R P (SEQ ID NO: 53) | S G T W D A S L S A Y V (SEQ ID NO: 61) |
| 4R23 | S G S S S N I G N N N V (SEQ ID NO: 44) | S A N S K R P (SEQ ID NO: 54) | S G S W D D S L S A Y V (SEQ ID NO: 62) |
| 4R25 | T G S S S N I G S N S V (SEQ ID NO: 45) | N D D S H R P (SEQ ID NO: 55) | S D A W D S S L S A Y V (SEQ ID NO: 63) |
| 4R66 | T G S S S N I G S N Y V (SEQ ID NO: 46) | S A D S Q R P (SEQ ID NO: 56) | S G T W D D S L S G Y V (SEQ ID NO: 64) |
| 4R67 | S S S S S N I G S N Y V (SEQ ID NO: 47) | S S D S H R P (SEQ ID NO: 57) | S G S W D Y S L S A Y V (SEQ ID NO: 65) |
| 4R73 | T G S S S N I G N N I V (SEQ ID NO: 48) | S D N S H R P (SEQ ID NO: 53) | S G S W D Y S L S A Y V (SEQ ID NO: 65) |
| 4R83 | T G S S S N I G N N D V (SEQ ID NO: 49) | N Y D S Q R P (SEQ ID NO: 58) | S A T W D A S L S A Y V (SEQ ID NO: 66) |
| 4R91 | S G S S S N I G N N A V (SEQ ID NO: 50) | N Y D N Q R P (SEQ ID NO: 59) | S G T W D D S L N G Y V (SEQ ID NO: 67) |
| 4R33 | S G S S S N I G N N A V (SEQ ID NO: 51) | T D D S H R P (SEQ ID NO: 55) | S G S W D Y S L S A Y V (SEQ ID NO: 65) |
| 4R34 | S G S S S N I G S N T F (SEQ ID NO: 52) | N A D S H R P (SEQ ID NO: 60) | S G T W D Y S L S G Y V (SEQ ID NO: 68) |
| 4R34.1 | S G S S S N I G S N T F (SEQ ID NO: 52) | N A D S H R P (SEQ ID NO: 60) | S G T W D Y S L S G Y V (SEQ ID NO: 68) |
| 4R34.2 | S G S S S N I G S N T F (SEQ ID NO: 52) | N A D S H R P (SEQ ID NO: 60) | S G T W D Y S L R G Y V (SEQ ID NO: 81) |
| 4R34.19 | S G S S S N I G S N T F (SEQ ID NO: 52) | N A D S H R P (SEQ ID NO: 60) | S G Y W D Y S L S G Y V (SEQ ID NO: 82) |
| 4R34.29 | S G S S S N I G S N T F (SEQ ID NO: 52) | N A D S H R P (SEQ ID NO: 60) | S G T W D Y S L S G   Y V (SEQ ID NO: 68) |
| 4R34.1.11 | S G S S A N S R T D G F (SEQ ID NO: 92) | N A D S H R P (SEQ ID NO: 60) | S G T W D Y S L S G Y V (SEQ ID NO: 68) |
| 4R34.1.13 | S G S A Q F G S R D N F (SEQ ID NO: 93) | N A D S H R P (SEQ ID NO: 60) | S G T W D Y S L S G Y V (SEQ ID NO: 68) |
| 4R34.1.17 | S G S T K Q M H N Y Q F (SEQ ID NO: 94) | N A D S H R P (SEQ ID NO: 60) | S G T W D Y S L S G Y V (SEQ ID NO: 68) |
| 4R34.1.18 | S G S L L R G E N L Q F (SEQ ID NO: 95) | N A D S H R P (SEQ ID NO: 60) | S G T W D Y S L S G Y V (SEQ ID NO: 68) |
| 4R34.1.19 | S G S P L F P D S G S F (SEQ ID NO: 96) | N A D S H R P (SEQ ID NO: 60) | S G T W D Y S L S G Y V (SEQ ID NO: 68) |
| 4R34.1.21 | S G S A A L D L S P S F (SEQ ID NO: 97) | N A D S H R P (SEQ ID NO: 60) | S G T W D Y S L S G Y V (SEQ ID NO: 68) |

The term "framework region" (FR) refers to a variable domain residue other than a CDR residue. Each variable domain typically has four FRs, identified as FR1, FR2, FR3, and FR4.

The antibody or antigen-binding fragment thereof binding to hIL-4Rα may include a heavy-chain variable region including a sequence selected from the group consisting of SEQ ID NOs: 1 to 10, 69 to 72, and 83.

In addition, the antibody or antigen-binding fragment thereof binding to the extracellular domain of hIL-4Rα may include a light-chain variable region including a sequence selected from the group consisting of SEQ ID NOs: 33 to 42, 77 to 80, and 86 to 91.

Specifically, the antibody or antigen-binding fragment thereof may include the heavy-chain and light-chain variable region sequences shown in Tables 3 and 4 below.

TABLE 3

| Heavy-chain variable region name | sequence | SEQ ID NO: |
|---|---|---|
| 4R14 | EVQLLESGGGLVQPGGSLRLSCAVSGFTFSNYAMSWVRQAPGKGLEWVSAISSGGGNIYYA<br>DSVKGRFTISRDNSKNTLYLQMNSLRAEDTAVYYCAKLRRYFDYWGQGTLVTVSS | SEQ ID NO: 1 |
| 4R23 | EVQLLESGGGLVQPGGSLRLSCAASGFTFSDYAMSWVRQAPGKGLEWVSAISSGGSSIYYA<br>DSVKGRFTISRDNSKNTLHLQMNSLRAEDTAVYYCARGPQRSATAVFDYWGQGTLVTVSS | SEQ ID NO: 2 |
| 4R25 | EVQLLESGGGLVQPGGSLRLSCAASGFTFSNYAMSWVRQAPGKGLEWVSWISPNSGNIYYA<br>DSVKGRFTISRDNSKNTLYLQMNSLRAEDTAVYYCARRPLSAAWSHSSYYNAMDVWGQGTL<br>VTVSS | SEQ ID NO: 3 |
| 4R66 | EVQLLESGGGLVQPGGSLRLSCAASGFTFSGYAMSWVRQAPGKGLEWVSLISHSGSNTYYA<br>DSVKGRFTISRDNSKNTLYLQMNSLRAEDTAVYYCARPHRAFDYWGQGTLVTVSS | SEQ ID NO: 4 |
| 4R67 | EVQLLESGGGLVQPGGSLRLSCAASGFTFSNYAMSWVRQAPGKGLEWVSGISHGSGSIYYA<br>DSVKGRFTISRDNSKNTLYLQMNSLRAEDTAVYYCARPHRAFDYWGQGTLVTVSS | SEQ ID NO: 5 |
| 4R73 | EVQLLESGGGLVQPGGSLRLSCAASGFTFSNYAMSWVRQAPGKGLEWVSGISHGNGSIYYA<br>DSVKGRFTISRDNSKNTLYLQMNSLRAEDTAVYYCAKTGRHFDYWGQGTLVTVSS | SEQ ID NO: 6 |
| 4R83 | EVQLLESGGGLVQPGGSLRLSCAASGFTFSNYAMSWVRQAPGKGLEWVSSISPSGSSIYYA<br>DSVKGRFTISRDNSKNTLYLQMNSLRAEDTAVYYCARSYRAFDYWGQGTLVTVSS | SEQ ID NO: 7 |
| 4R91 | EVQLLESGGGLVQPGGSLRLSCAASGFTFSNYAMSWVRQAPGKGLEWVSAISPSGGSIYYA<br>DSVKGRFTISRDNSKNTLYLQMNSLRAEDTAVYYCARAKRAFDYWGQGTLVTVSS | SEQ ID NO: 8 |
| 4R33 | EVQLLESGGGLVQPGGSLRLSCAASGFTFSNYAMSWVRQAPGKGLEWVSAISPGSGSTYYA<br>DSVKGRFTISRDNSKNTLYLQMNSLRAEDTAVYYCAKFRRHFDYWGQGTLVTVSS | SEQ ID NO: 9 |
| 4R34 | EVQLLESGGGLVQPGGSLRLSCAASGFTFSNYAMSWVRQAPGKGLEWVSAISSGGGNIYYA<br>DSVKGRFTISRDNSKNTLYLQMNSLRAEDTAVYYCARVHRAFDYWGQGTLVTVSS | SEQ ID NO: 10 |
| 4R34.1 | EVQLLESGGGLVQPGGSLRLSCAASGFTFSNYAMSWVRQAPGKGLEWVSAITSSGRSIYYA<br>DSVKGRFTISRDNSKNTLYLQMNSLRAEDTAVYYCARVHRAFDYWGQGTLVTVSS | SEQ ID NO: 69 |
| 4R34.2 | EVQLLESGGGLVQPGGSLRLSCAASGFTFSNYAMSWVRQAPGKGLEWVSAITSSGANIYYA<br>DSVKGRFTISRDNSKNTLYLQMNSLRAEDTAVYYCARVHRAFDYWGQGTLVTVSS | SEQ ID NO: 70 |
| 4R34.19 | EVQLLESGGGLVQPGGSLRLSCAASGFTFSNYAMSWVRQAPGKGLEWVSAITSSGGNIYYA<br>DSVKGRFTISRDNSKNTLYLQMNSLRAEDTAVYYCARVHRAFDYWGQGTLVTVSS | SEQ ID NO: 71 |
| 4R34.29 | EVQLLESGGGLVQPGGSLRLSCAASGFTFSNYAMSWVRQAPGKGLEWVSAITAGGGSIYYA<br>DSVKGRFTISRDNSKNTLYLQMNSLRAEDTAVYYCARVHRAFDYWGQGTLVTVSS | SEQ ID NO: 72 |
| 4R34.1.19 | EVQLLESGGGLVQPGGSLRLSCAASGFTFSRHAMAWVRQAPGKGLEWVSAITSSGRSIYYA<br>DSVKGRFTISRDNSKNTLYLQMNSLRAEDTAVYYCARVHRAFDYWGQGTLVTVSS | SEQ ID NO: 83 |

TABLE 4

| Light-chain variable region name | sequence | SEQ ID NO: |
|---|---|---|
| 4R14 | QSVLTQPPSASGTPGQRVTISCSGSSSNIGNNYVNWYQQLPGTAPKLLIYDNSHRPSGVPDRFSGSK<br>SGTSASLAISGLRSEDEADYYCGTWDASLSAYVFGGGTKLTVL | SEQ ID NO: 33 |
| 4R23 | QSVLTQPPSASGTPGQRVTISCSGSSSNIGNNNVSWYQQLPGTAPKLLIYANSKRPSGVPDRFSGSK<br>SGTSASLAISGLRSEDEADYYCGSWDDSLSAYVFGGGTKLTVL | SEQ ID NO: 34 |
| 4R25 | QSVLTQPPSAPGTPGQRVTISCTGSSSNIGSNVNWYQQLPGTAPKLLIYDDSHRPSGVPDRFSGSK<br>SGTSASLAISGLRSEDEADYYCDAWDSSLSAYVFGGGTKLTVL | SEQ ID NO: 35 |
| 4R66 | QSVLTQPPSASGTPGQRVTLSCTGSSSNIGSNYVSWYQQLPGTAPKLLIYADSQRPSGVPDRFSGSK<br>SGTSASLAISGLRSEDEADYYCGTWDDSLSGYVFGGGTKLTVL | SEQ ID NO: 36 |
| 4R67 | QSVLTQPPSASGTPGQRVTISCSSSSSNIGSNYVSWYQQLPGTAPKLLIYSDSHRPSGVPDRFSGSK<br>SGTSASLAISGLRSEDEADYYCGSWDYSLSAYVFGGGTKLTVL | SEQ ID NO: 37 |
| 4R73 | QSVLTQPPSASGTPGQRVTISCTGSSSNIGNNTVSWYQQLPGTAPKLLIYDNSHRPSGVPDRFSGSK<br>SGTSASLAISGLQSEDEADYYCGSWDYSLSAYVFGGGTKLTVL | SEQ ID NO: 38 |
| 4R83 | QSVLTQPPSASGTPGQRVTISCTGSSSNIGNNDVNWYQQLPGTAPKLLIYYDSQRPSGVPDRFSGSK<br>SGTSASLAISGLRSEDEADYYCATWDASLSAYVFGGGTKLTVL | SEQ ID NO: 39 |

TABLE 4-continued

| Light-chain variable region name | sequence | SEQ ID NO: |
|---|---|---|
| 4R91 | QSVLTQPPSASGTPGQRVTISCSGSSSNIGSNAVNWYQQLPGTAPKLLIYYDNQRPSGVPDRFSGSK SGTSASLAISGLRSEDEADYYCGTWDDSLNGYVFGGGTKLTVL | SEQ ID NO: 40 |
| 4R33 | QSVLTQPPSASGTPGQRVTISCSGSSSNIGNNAVTWYQQLPGTAPKLLIYDDSHRPSGVPDRFSGSK SGTSASLAISGLRSEDEADYYCGSWDYSLSAYVFGGGTKLTVL | SEQ ID NO: 41 |
| 4R34 | QSVLTQPPSASGTPGQRVTISCSGSSSNIGSNTFNWYQQLPGTAPKLLIYADSHRPSGVPDRFSGSK SGTSASLAISGLRSEDEADYYCGTWDYSLSGYVLGGGTKLTVL | SEQ ID NO: 42 |
| 4R34.1 | QSVLTQPPSASGTPGQRVTISCSGSSSNIGSNTFNWYQQLPGTAPKLLIYADSHRPSGVPDRFSGSK SGTSASLAISGLRSEDEADYYCGTWDYSLSGYVLGGGTKLTVL | SEQ ID NO: 77 |
| 4R34.2 | QSVLTQPPSASGTPGQRVTISCSGSSSNIGSNTFNWYQQLPGTAPKLLIYADSHRPSGVPDRFSGSK SGTSASLAISGLRSEDEADYYCGTWDYSLRGYVLGGGTKLTVL | SEQ ID NO: 78 |
| 4R34.19 | QSVLTQPPSASGTPGQRVTISCSGSSSNIGSNTFNWYQQLPGTAPKLLIYADSHRPSGVPDRFSGSK SGTSASLAISGLRSEDEADYYCGYWDYSLSGYVLGGGTKLTVL | SEQ ID NO: 79 |
| 4R34.29 | QSVLTQPPSASGTPGQRVTISCSGSSSNIGSNTFNWYQQLPGTAPKLLIYADSHRPSGVPDRFSGSK SGTSASLAISGLRSEDEADYYCGTWDYSLSGYVLGGGTKLTVL | SEQ ID NO: 80 |
| 4R34.1.11 | QSVLTQPPSASGTPGQRVTISCSGSSANSRTDGFNWYQQLPGTAPKLLIYADSHRPSGVPDRFSGSK SGTSASLAISGLRSEDEADYYCGTWDYSLSGYVLGGGTKLTVLG | SEQ ID NO: 86 |
| 4R34.1.13 | QSVLTQPPSASGTPGQRVTISCSGSAQFGSRDNFNWYQQLPGTAPKLLIYADSHRPSGVPDRFSGSK SGTSASLAISGLRSEDEADYYCGTWDYSLSGYVLGGGTKLTVLG | SEQ ID NO: 87 |
| 4R34.1.17 | QSVLTQPPSASGTPGQRVTISCSGSTKQMHNYQFNWYQQLPGTAPKLLIYADSHRPSGVPDRFSGSK SGTSASLAISGLRSEDEADYYCGTWDYSLSGYVLGGGTKLTVLG | SEQ ID NO: 88 |
| 4R34.1.18 | QSVLTQPPSASGTPGQRVTISCSGSLLRGENLQFNWYQQLPGTAPKLLIYADSHRPSGVPDRFSGSK SGTSASLAISGLRSEDEADYYCGTWDYSLSGYVLGGGTKLTVLG | SEQ ID NO: 89 |
| 4R34.1.19 | QSVLTQPPSASGTPGQRVTISCSGSPLFPDSGSFNWYQQLPGTAPKLLIYADSHRPSGVPDRFSGSK SGTSASLAISGLRSEDEADYYCGTWDYSLSGYVLGGGTKLTVLG | SEQ ID NO: 90 |
| 4R34.1.21 | QSVLTQPPSASGTPGQRVTISCSGSAALDLSPSFNWYQQLPGTAPKLLIYADSHRPSGVPDRFSGSK SGTSASLAISGLRSEDEADYYCGTWDYSLSGYVLGGGTKLTVLG | SEQ ID NO: 91 |

The antibody or antibody fragment of the present invention may include the sequence of the anti-hIL-4Rα antibody mentioned herein as well as biological equivalents thereof, as long as it can specifically recognize hIL-4Rα. For example, additional changes can be made to the amino acid sequence of the antibody in order to further improve the binding affinity and/or other biological properties of the antibody. Such modifications include, for example, deletion, insertion and/or substitution of the amino acid sequence residues of the antibody.

When taking into consideration variations having biologically equivalent activity, the antibody or a nucleotide molecule encoding the same according to the present invention is interpreted to include a sequence having substantial identity with the sequence set forth in the sequence number. The term "substantial identity" means that a sequence has homology of at least 90%, more preferably homology of at least 95%, at least 96%, at least 97%, at least 98% or at least 99%, when aligning the sequence of the present invention with another sequence so as to correspond thereto as closely as possible and analyzing the aligned sequence using algorithms commonly used in the art. The alignment method for sequence comparison is well-known in the art. The NCBI Basic Local Alignment Search Tool (BLAST) is accessible through NCBI or the like, and can be used in conjunction with sequence analysis programs such as BLASTP, BLASM, BLASTX, TBLASTN and TBLASTX over the Internet. BLAST is available at www.ncbi.nlm.nih.gov/BLAST/. A method of comparing sequence homology using this program can be found at www.ncbi.nlm.nih.gov/BLAST/blast_help.html.

Based on this, the antibody or antigen-binding fragment thereof according to the present invention can have homology of 90%, 91%, 92%, 93%, 94%, 95%, 96%, 97%, 98%, or 99% or more. Such homology can be determined through sequence comparison and/or alignment by methods known in the art. For example, the percentage sequence identity of the nucleic acid or protein according to the present invention can be determined using a sequence comparison algorithm (i.e., BLAST or BLAST 2.0), manual alignment, or visual inspection.

In another aspect of the present invention, provided is a nucleic acid encoding the antibody or an antigen-binding fragment thereof.

By isolating the nucleic acid encoding the antibody or an antigen-binding fragment thereof according to the present invention, an antibody or antigen-binding fragment thereof can be produced via recombination. The nucleic acid is isolated and inserted into a replicable vector, followed by further cloning (amplification of DNA) or further expression. Based on this, in another aspect, the present invention is directed to a vector including the nucleic acid.

The term "nucleic acid" is intended to encompass both DNA (gDNA and cDNA) and RNA molecules, and a nucleotide, which is a basic constituent unit of a nucleic acid, includes naturally derived nucleotides as well as analogues, wherein sugar or base moieties are modified. The sequence of the nucleic acid encoding heavy- and light-chain variable regions of the present invention can vary. Such variation includes addition, deletion, or non-conservative or conservative substitution of nucleotides.

The DNA encoding the antibody can be easily separated or synthesized using conventional procedures (for example, using an oligonucleotide probe capable of specifically binding to DNA encoding heavy and light chains of the antibody). A variety of vectors are obtainable. Vector components generally include, but are not limited to, one or more of the following components: signal sequences, replication origins, one or more marker genes, enhancer elements, promoters, and transcription termination sequences.

As used herein, the term "vector" refers to a means for expressing target genes in host cells, and includes plasmid vectors, cosmid vectors, and viral vectors such as bacteriophage vectors, adenovirus vectors, retroviral vectors and adeno-associated viral vectors. The polynucleotide encoding the antibody in the vector is operably linked to a promoter.

The term "operably linked" means a functional linkage between a nucleic acid expression regulation sequence (e.g., an array of promoter, signal sequence or transcription regulator binding sites) and another nucleic acid sequence, and enables the regulation sequence to regulate the transcription and/or translation of the other nucleic acid sequence.

When a prokaryotic cell is used as a host, it generally includes a potent promoter capable of conducting transcription (such as a tac promoter, lac promoter, lacUV5 promoter, lpp promoter, pLλ promoter, pRλ promoter, racy promoter, amp promoter, recA promoter, SP6 promoter, trp promoter, or T7 promoter), a ribosome-binding site for initiation of translation, and a transcription/translation termination sequence. In addition, for example, when a eukaryotic cell is used as a host, it includes a promoter (e.g., a metallothionein promoter, a β-actin promoter, a human hemoglobin promoter and a human muscle creatine promoter) derived from the genome of mammalian cells, or a promoter derived from a mammalian virus such as an adenovirus late promoter, vaccinia virus 7.5K promoter, SV40 promoter, cytomegalovirus (CMV) promoter, HSV tk promoter, mouse mammary tumor virus (MMTV) promoter, HIV LTR promoter, Moloney virus promoter, Epstein-Barr virus (EBV) promoter, or Rous sarcoma virus (RSV) promoter, and generally has a polyadenylation sequence as a transcription termination sequence.

Optionally, the vector may be fused with another sequence in order to facilitate purification of the antibody expressed therefrom. The sequence to be fused therewith includes, for example, glutathione S-transferase (Pharmacia, USA), maltose-binding protein (NEB, USA), FLAG (IBI, USA), 6×His (hexahistidine; Qiagen, USA) and the like.

The vector includes antibiotic-resistant genes commonly used in the art as selectable markers, and examples thereof include genes conferring resistance to ampicillin, gentamycin, carbenicillin, chloramphenicol, streptomycin, kanamycin, geneticin, neomycin and tetracycline.

In another aspect, the present invention is directed to a cell transformed with the above-mentioned vector. The cell used to produce the antibody of the present invention may be a prokaryote, yeast or higher eukaryotic cell, but is not limited thereto.

Prokaryotic host cells such as *Escherichia coli*, the genus *Bacillus*, such as *Bacillus subtilis* and *Bacillus thuringiensis*, *Streptomyces* spp., *Pseudomonas* spp. (for example, *Pseudomonas putida*), *Proteus mirabilis* and *Staphylococcus* spp. (for example, *Staphylococcus carnosus*) can be used.

Interest in animal cells is the greatest, and examples of useful host cell lines include, but are not limited to, COS-7, BHK, CHO, CHOK1, DXB-11, DG-44, CHO/-DHFR, CV1, COS-7, HEK293, BHK, TM4, VERO, HELA, MDCK, BRL 3A, W138, Hep G2, SK-Hep, MMT, TRI, MRC 5, FS4, 3T3, RIN, A549, PC12, K562, PER.C6, SP2/0, NS-0, U20S, and HT1080.

In another aspect, the present invention is directed to a method of producing the antibody or antigen-binding fragment thereof including: (a) culturing the cells; and (b) recovering an antibody or antigen-binding fragment thereof from the cultured cells.

The cells can be cultured in various media. Any commercially available medium can be used as a culture medium without limitation. All other essential supplements well-known to those skilled in the art may be included in appropriate concentrations. Culture conditions such as temperature and pH are those that are conventionally used with the host cells selected for expression, which will be apparent to those skilled in the art.

The recovery of the antibody or antigen-binding fragment thereof can be carried out, for example, by centrifugation or ultrafiltration to remove impurities and further purification of the resulting product using, for example, affinity chromatography. Other additional purification techniques such as anion or cation exchange chromatography, hydrophobic interaction chromatography and hydroxyapatite (HA) chromatography may be used.

In another aspect, the present invention is directed to an antibody-drug conjugate (ADC) in which the antibody or antigen-binding fragment thereof is fused with a bioactive molecule selected from the group consisting of peptides, proteins, small-molecule drugs, nucleic acids, nanoparticles and liposomes.

The proteins include antibodies, fragments of antibodies, immunoglobulins, peptides, enzymes, growth factors, cytokines, transcription factors, toxins, antigenic peptides, hormones, transport proteins, motor function proteins, receptors, signaling proteins, storage proteins, membrane proteins, transmembrane proteins, internal proteins, external proteins, secreted proteins, viral proteins, sugar proteins, truncated proteins, protein complexes, chemically modified proteins and the like.

The term "small-molecule drugs" refers to an organic compound, an inorganic compound or an organometallic compound that has a molecular weight of less than about 1,000 daltons and has activity as a therapeutic agent for diseases, which is widely used herein. The small-molecule drug used herein includes oligopeptides and other biomolecules having a molecular weight of less than about 1,000 daltons.

As used herein, the term "nanoparticle" refers to a particle including a material having a diameter of 1 to 1,000 nm, and the nanoparticle may be a metal/metal core-shell complex including a metal nanoparticle, a metal nanoparticle core and a metal shell including the core, a metal/non-metal core-shell complex including a metal nanoparticle core and a non-metal shell surrounding the core, or a nonmetal/metal core-shell complex including a nonmetal nanoparticle core and a metal shell surrounding the core. According to one embodiment, the metal may be selected from gold, silver, copper, aluminum, nickel, palladium, platinum, magnetic iron, and oxides thereof, but is not limited thereto, and the nonmetal may be selected from silica, polystyrene, latex and acrylic substances, but is not limited thereto.

The liposome consists of one or more lipid bilayer membranes surrounding an aqueous internal compartment that can self-associate. Liposomes can be specified based on the type and size of the membrane thereof. Small unilamellar vesicles (SUVs) have a single membrane, and may have a diameter of 20 nm to 50 nm. Large unilamellar vesicles (LUV) may have a diameter of 50 nm or more. Oligolamellar large vesicles and multilamellar large vesicles have multiple, generally concentric, membrane layers, and may be 100 nm or more in diameter. Liposomes having a plurality of non-concentric membranes, that is, several small vesicles contained within larger vesicles, are called "multivesicular vesicles".

As used herein, the term "fusion" refers to the integration of two molecules having different or identical functions or structures, and includes fusion through any physical, chemical or biological method capable of binding the antibody or antigen-binding fragment thereof to the protein, small-molecule drug, nanoparticle, or liposome. The fusion may preferably be carried out using a linker peptide, and the linker peptide may mediate the fusion with the bioactive molecule at various positions of the antibody light-chain variable region, antibody, or fragment thereof according to the present invention.

In another aspect, the present invention is directed to a pharmaceutical composition for preventing or treating inflammatory diseases containing the antibody or antigen-binding fragment thereof or the conjugate as an active ingredient.

Examples of inflammatory diseases that can be treated using the antibody according to the present invention may include allergic diseases such as atopic dermatitis, asthma, allergic rhinitis and food allergic reactions, but are not limited thereto.

In addition to allergic diseases such as atopic dermatitis, asthma, allergic rhinitis or food allergic reactions, the diseases that can be treated using the antibody according to the present invention include arthritis (including septic arthritis), herpes, chronic idiopathic urticaria, scleroderma, hypertrophic scarring, Whipple's disease, benign prostatic hyperplasia, lung disorders such as mild, moderate or severe asthma, inflammatory disorders such as inflammatory bowel disease, Kawasaki disease, sickle cell disease, Churg-Strauss syndrome, Grave's disease, pre-eclampsia, Sjogren's syndrome, autoimmune lymphocyte proliferation syndrome, autoimmune hemolysis anemia, Barrett's esophagus, autoimmune uveitis, tuberculosis, or nephropathy, but are not limited thereto.

In another aspect, the present invention is directed to a pharmaceutical composition for preventing or treating inflammatory diseases including: (a) a pharmaceutically effective amount of the antibody or antigen-binding fragment thereof according to the present invention; and (b) a pharmaceutically acceptable carrier.

In another aspect, the present invention is directed to a method for preventing or treating inflammatory diseases including administering the antibody or antigen-binding fragment thereof according to the present invention to a patient.

The antibody according to the present invention is useful for the prevention or treatment of hIL-4-mediated diseases by eliminating, inhibiting or reducing hIL-4 activity. The antibody according to the present invention can inhibit the growth of T cells and differentiation of Th2 cells by suppressing the signals of hIL-4 and hIL-13, which bind to hIL-4Rα and induce a Th2 immune response.

As used herein, the term "prevention" refers to any action causing the suppression of growth of inflammatory diseases or the delay of progression of inflammatory diseases by administration of the composition according to the present invention. The term "treatment" means suppression of the progression of inflammatory diseases or alleviation or elimination of inflammatory diseases. The antibodies of the present invention can be useful both in vitro and in vivo for applications involving hIL-4Rα-expressing cells.

The pharmaceutical composition of the present invention contains the antibody or antigen-binding fragment thereof or the conjugate according to the present invention, and the pharmaceutical composition may further contain a pharmaceutically acceptable carrier, in addition to the component for administration of the pharmaceutical composition of the present invention. The term "pharmaceutically acceptable carrier" as used herein refers to a carrier or diluent that does not impair the biological activities or properties of the administered compound and does not stimulate an organism. Pharmaceutically acceptable carriers for compositions that are formulated into liquid solutions are sterilized and biocompatible, and examples thereof include saline, sterile water, buffered saline, albumin injection solutions, dextrose solutions, maltodextrin solutions, glycerol, and mixtures of one or more thereof. If necessary, other conventional additives such as antioxidants, buffers and bacteriostatic agents may be added. In addition, diluents, dispersants, surfactants, binders and lubricants can be additionally added to formulate injectable solutions such as aqueous solutions, suspensions and emulsions, pills, capsules, granules, or tablets.

The pharmaceutical composition according to the present invention may be any one of various oral or parenteral formulations. In this regard, the pharmaceutical composition may be formulated using an ordinary diluent or excipient such as a filler, a thickener, a binder, a wetting agent, a disintegrant, a surfactant, or the like. Solid formulations for oral administration may include tablets, pills, powders, granules, capsules and the like. Such a solid formulation is prepared by mixing at least one compound with at least one excipient such as starch, calcium carbonate, sucrose, lactose or gelatin. In addition to a simple excipient, a lubricant such as magnesium stearate or talc may be further used. Liquid formulations for oral administration may include suspensions, solutions for internal use, emulsions, syrups, and the like. In addition to a simple diluent such as water or liquid paraffin, various excipients such as wetting agents, sweeteners, aromatics and preservatives may be incorporated in the liquid formulations. In addition, formulations for parenteral administration include sterile aqueous solutions, non-aqueous solvents, suspensions, emulsions, lyophilizates, suppositories and the like. Useful non-aqueous solvents and suspensions include propylene glycol, polyethylene glycol, vegetable oils such as olive oil and injectable esters such as ethyl oleate. The base ingredients of suppositories include Witepsol, macrogol, Tween 61, cacao butter, laurin butter and glycerogelatin.

The method for treating inflammatory diseases using the antibody or antigen-binding fragment thereof or the conjugate according to the present invention includes administering, to a subject, a pharmaceutically effective amount of the antibody or antigen-binding fragment thereof, or the conjugate. It will be apparent to those skilled in the art that an appropriate total daily dose can be determined based on the judgment of a medical specialist. In addition, the antibody, antigen-binding fragment thereof, or the conjugate may be administered in a single dose, or may be divided into multiple doses. However, in consideration of the objects of the present invention, the specific therapeutically effective amount for a certain patient is preferably determined depending upon a variety of factors, including the type and extent of the response to be achieved, as well as the presence of other agents used, the specific composition, the age, body weight, general state of health, gender, and diet of the patient, the administration time, the administration route, the treatment period, and drugs used in conjunction with or concurrently with the specific composition, and other similar factors well-known in the pharmaceutical field.

The subject to which the composition of the present invention is administered includes mammals including humans, without limitation thereto.

As used herein, the term "administration" refers to an action of supplying the pharmaceutical composition according to the present invention to a patient by any appropriate method, and the composition according to the present invention may be orally or parenterally administered through any one of various routes enabling the composition to be delivered to a target tissue.

The antibody or antigen-binding fragment thereof according to the present invention may be used as a single agent or in combination with a conventional therapeutic agent.

In another aspect, the present invention is directed to a composition for diagnosing inflammatory diseases including the antibody or an antigen-binding fragment thereof. Also, in another aspect, the present invention is directed to a kit for diagnosing inflammatory diseases containing the diagnostic composition.

As used herein, the term "diagnosis" means determining the presence or features of pathophysiology. In the present invention, diagnosis serves to determine the onset or progress of an inflammatory disease.

For diagnostic methods using the antibody or antigen-binding fragment thereof according to the present invention, the drug may include a detectable label used to detect the presence of hIL-4Rα antigen-expressing cells in vitro or in vivo. Radioisotopes that are detectable in vivo such as labels that can be detected using scintillation, magnetic resonance imaging or ultrasound can be used for clinical diagnostic applications. Useful scintillation labels include positron emitters and γ-emitters. Representative contrast agents as magnetic source for imaging include paramagnetic or superparamagnetic ions (e.g., iron, copper, manganese, chromium, erbium, europium, dysprosium, holmium and gadolinium), iron oxide particles, and water-soluble contrast agents. For ultrasonic detection, a gas or liquid can be trapped in the porous inorganic particles released as a microbubble contrast agent. Detectable labels useful for in-vitro detection include fluorophores, detectable epitopes or binders and radiolabels.

The kit for diagnosing inflammatory diseases may further include a composition, solution or device having one or more other components suitable for the analysis method.

In one embodiment, the kit may include a bottle, vial, bag, needle, or syringe. The container may be made from various materials, such as glass, plastic, or metal. The label on the container may provide instructions for use. The kit may further include other materials desirable from commercial and usage perspectives, such as other buffers, diluents, filters, needles and syringes.

EXAMPLES

Hereinafter, the present invention will be described in more detail with reference to examples. However, it will be obvious to those skilled in the art that these examples are provided only for illustration of the present invention and should not be construed as limiting the scope of the present invention.

Example 1: Expression of Recombinant Human Interleukin-4 Receptor α (hIL-4Rα)

An antigenic protein for deriving an antibody specific for human interleukin-4 receptor α (hIL-4Rα) was prepared. Since hIL-4Rα is a glycoprotein, an animal cell expression system was used. The full-length cDNA (Met26-Ser232) was cloned into an animal expression vector (pSecTag2A) using the restriction enzyme NheI/BamHI, and pSecTag2A-hIL-4Rα was constructed such that the 6× histidine-labeled protein was fused with the C-terminus (FIG. 1A). The antigenic protein was transiently transfected into HEK293F (Invitrogen) cells for expression and purification. Upon transfection of 100 mL thereof in a shake flask (corning), HEK293F cells were seeded in 90 ml of medium at a density of $1.0 \times 10^6$ cells/ml and incubated at 120 rpm, 8% $CO_2$, and 37° C. 125 μg of the constructed plasmid was diluted and filtered in 5 ml of a serum-free Freestyle 293 expression medium (Invitrogen), and was mixed with 5 ml of a medium diluted in 375 μg (7.5 μg/ml) of polyethyleneimine and reacted at room temperature for 10 minutes. Then, the reacted mixed medium was added to 90 ml of the cells previously seeded at 90 ml, followed by incubation at 120 rpm, 8% $CO_2$, and then subjecting to further incubation for 6 days. Proteins were purified from the cell incubation supernatant collected with reference to standard protocols. The supernatant was applied to a nickel Sepharosem 6 Fast Flow (GE Healthcare) and washed with a washing buffer (50 mM phosphate, 300 mM NaCl, 50 mM imidazole pH 8.0), and then the protein was eluted with an elution buffer (50 mM phosphate, 300 mM NaCl, 250 mM imidazole, pH 8.0).

The eluted protein was exchanged with a storage buffer (PBS pH 7.4) using a PD-10 desalting column (GE Healthcare), and was then concentrated using a Vivaspin 30,000 MWCO (Sartorius) centrifugal concentrator. The absorbance at a wavelength of 562 nm of the purified protein was measured and the amount thereof was quantified using a solution in the BCA protein assay kit (Thermo) according to the drawn standard curve.

In order to confirm the deglycosylated state of hIL-4Rα, the purified hIL-4Rα protein and PNGaseF (NEB) enzyme were reacted with reference to a standard protocol.

Specifically, 2 μl of GlycoBuffer 2 (10×) was added to 10 pg of hIL-4Rα protein, and the final volume was adjusted to 20 μl with deionized water. 5 μl of PNGaseF enzyme was added to this mixture, followed by incubation at 37° C. for 24 hours. The purity of 12.5 μl of the mixture and 5 μg of the purified hIL-4Rα protein was detected through SDS-PAGE analysis (FIG. 1B). In the purified protein, slightly shifted bands were observed at a molecular weight greater than the expected molecular weight (26 kDa). Upon treatment along with PNGaseF, the band was observed at 26 kDa, along with the band corresponding to PNGaseF at 36 kDa. This indicates that the shifted bands are due to different glycosylation patterns.

Example 2: Selection of Monoclonal Antibodies in Yeast Surface Expression Library A yeast Fab library expressing the human antibody Fab (Baek, D S and Y S Kim (2014). J. Microbiol. Biotechnol. 24(3): 408-420) was screened to screen yeast clones expressing Fab specifically binding to the hIL-4Rα antigen protein prepared in <Example 1>.

The method of selecting a clone that specifically binds to the hIL-4Rα antigen protein from the yeast Fab library is as follows. First, the hIL-4Rα antigen protein was conjugated with biotin using a kit (EZ-LINK™ Sulfo-NHS-LC-Biotinylation kit, Pierce Inc.). The expression level of the yeast library expressing Fab can be detected through an Alexa 488-conjugated anti-IgG antibody (goat Alexa 488-conjugated anti-Fc antibody, Thermo), and the antigen-binding ability thereof can be detected using PE-conjugated streptavidin (Streptavidin-R-phycoerythrin conjugate (SA-PE), Thermo). Clones expressing a high amount of Fab and having high ability to bind to biotinylated hIL-4Rα were selected using the FACS process while reducing the concentration of the library to biotinylated hIL-4Rα, and the process of analyzing the derived pool was repeated. This process was repeated 4 times.

Finally, DNA was obtained from yeast cells expressing each individual clone that specifically binds to hIL-4Rα, and sequence analysis was performed to select 10 types of antibodies in which certain nucleotide sequences and amino acid sequences were identified.

Tables 5 and 7 show the heavy-chain CDR sequences and heavy-chain variable region sequences of 10 individual clones having binding ability to the selected hIL-4Rα, respectively, and Tables 6 and 8 show the light-chain CDR sequences and the light-chain variable region sequences, respectively.

TABLE 5

| Heavy-chain variable region name | CDR1 sequence | | | | | | CDR2 sequence | | | | | | | | | | | | | | | |
|---|---|---|---|---|---|---|---|---|---|---|---|---|---|---|---|---|---|---|---|---|---|---|
| Kabat No. | 31 | 32 | 33 | 34 | 35 | 50 | 51 | 52 | 52a | 53 | 54 | 55 | 56 | 57 | 58 | 59 | 60 | 61 | 62 | 63 | 64 | 65 |
| 4R14 | N | Y | A | M | S | A | I | S | S | G | G | G | N | I | Y SEQ ID No: 14 | Y | A | D | S | V | K | G |
| 4R23 | D | Y | A | M | S | A | I | S | S | G | G | S | S | I | Y SEQ ID No: 15 | Y | A | D | S | V | K | G |
| 4R25 | N | Y | A | M | S | W | I | S | P | N | S | G | N | I | Y SEQ ID No: 16 | Y | A | D | S | V | K | G |
| 4R66 | G | Y | A | M | S | L | I | S | H | S | G | S | N | T | Y SEQ ID No: 17 | Y | A | D | S | V | K | G |
| 4R67 | N | Y | A | M | S | G | I | S | H | G | G | G | S | I | Y SEQ ID No: 18 | Y | A | D | S | V | K | G |
| 4R73 | N | Y | A | M | S | G | I | S | H | G | N | G | S | I | Y SEQ ID No: 19 | Y | A | D | S | V | K | G |
| 4R83 | N | Y | A | M | S | S | I | S | P | S | G | S | S | I | Y SEQ ID No: 20 | Y | A | D | S | V | K | G |
| 4R91 | N | Y | A | M | S | A | I | S | P | S | G | G | S | I | Y SEQ ID No: 21 | Y | A | D | S | V | K | G |
| 4R33 | N | Y | A | M | S | A | I | S | P | G | G | G | S | T | Y SEQ ID No: 22 | Y | A | D | S | V | K | G |
| 4R34 | N | Y | A | M | S | A | I | S | S | G | G | G | N | I | Y SEQ ID No: 14 | Y | A | D | S | V | K | G |

TABLE 5-continued

| Heavy-chain variable region name | CDR3 sequence | | | | | | | | | | | | | | | | | |
|---|---|---|---|---|---|---|---|---|---|---|---|---|---|---|---|---|---|---|
| Kabat No. | 95 | 96 | 97 | 98 | 99 | 100 | 100a | 100b | 100c | 100d | 100e | 100f | 100g | 100h | 100i | 100j | 101 | 102 |
| 4R14 | L | R | R | Y | F | . | . | . | . | . | . | . | . | . | . | . | D | Y |
| | | | | | | | | | | | SEQ ID No: 23 | | | | | | | |
| 4R23 | G | P | Q | R | S | A | T | A | V | F | . | . | . | . | . | . | D | Y |
| | | | | | | | | | | | SEQ ID No: 24 | | | | | | | |
| 4R25 | R | P | L | S | A | A | W | S | H | S | S | Y | Y | N | A | M | D | V |
| | | | | | | | | | | | SEQ ID No: 25 | | | | | | | |
| 4R66 | P | H | R | A | F | . | . | . | . | . | . | . | . | . | . | . | D | Y |
| | | | | | | | | | | | SEQ ID No: 26 | | | | | | | |
| 4R67 | T | G | R | D | F | . | . | . | . | . | . | . | . | . | . | . | D | Y |
| | | | | | | | | | | | SEQ ID No: 27 | | | | | | | |
| 4R73 | T | G | R | H | F | . | . | . | . | . | . | . | . | . | . | . | D | Y |
| | | | | | | | | | | | SEQ ID No: 28 | | | | | | | |
| 4R83 | S | Y | R | A | F | . | . | . | . | . | . | . | . | . | . | . | D | Y |
| | | | | | | | | | | | SEQ ID No: 29 | | | | | | | |
| 4R91 | A | K | R | A | F | . | . | . | . | . | . | . | . | . | . | . | D | Y |
| | | | | | | | | | | | SEQ ID No: 30 | | | | | | | |
| 4R33 | F | R | R | H | F | . | . | . | . | . | . | . | . | . | . | . | D | Y |
| | | | | | | | | | | | SEQ ID No: 31 | | | | | | | |
| 4R34 | V | H | R | A | F | . | . | . | . | . | . | . | . | . | . | . | D | Y |
| | | | | | | | | | | | SEQ ID No: 32 | | | | | | | |

TABLE 6

| Light-chain variable region name | CDR1 sequence | | | | | | | | | | | | CDR2 sequence | | | | | | |
|---|---|---|---|---|---|---|---|---|---|---|---|---|---|---|---|---|---|---|---|
| Kabat No. | 24 | 25 | 26 | 27 | 27a | 27b | 28 | 29 | 30 | 31 | 32 | 33 | 34 | 50 | 51 | 52 | 53 | 54 | 55 | 56 |
| 4R14 | S | G | S | S | S | N | I | G | N | N | Y | V | N | D | N | S | H | R | P | S |
| | | | | | | SEQ ID NO: 43 | | | | | | | | SEQ ID NO: 53 | | | | | | |
| 4R23 | S | G | S | S | S | N | I | G | N | N | N | V | S | A | N | S | K | R | P | S |
| | | | | | | SEQ ID NO: 44 | | | | | | | | SEQ ID NO: 54 | | | | | | |
| 4R25 | T | G | S | S | S | N | I | G | S | N | S | V | N | D | D | S | H | R | P | S |
| | | | | | | SEQ ID NO: 45 | | | | | | | | SEQ ID NO: 55 | | | | | | |
| 4R66 | T | G | S | S | S | N | I | G | S | N | Y | V | S | A | D | S | Q | R | P | S |
| | | | | | | SEQ ID NO: 46 | | | | | | | | SEQ ID NO: 56 | | | | | | |
| 4R67 | S | S | S | S | S | N | I | G | S | N | Y | V | S | S | D | S | H | R | P | S |
| | | | | | | SEQ ID NO: 47 | | | | | | | | SEQ ID NO: 57 | | | | | | |
| 4R73 | T | G | S | S | S | N | I | G | N | N | T | V | S | D | N | S | H | R | P | S |
| | | | | | | SEQ ID NO: 48 | | | | | | | | SEQ ID NO: 53 | | | | | | |
| 4R83 | T | G | S | S | S | N | I | G | N | N | D | V | N | Y | D | S | Q | R | P | S |
| | | | | | | SEQ ID NO: 49 | | | | | | | | SEQ ID NO: 58 | | | | | | |
| 4R91 | S | G | S | S | S | N | I | G | S | N | A | V | N | Y | D | N | Q | R | P | S |
| | | | | | | SEQ ID NO: 50 | | | | | | | | SEQ ID NO: 59 | | | | | | |
| 4R33 | S | G | S | S | S | N | I | G | N | N | A | V | T | D | D | S | H | R | P | S |
| | | | | | | SEQ ID NO: 51 | | | | | | | | SEQ ID NO: 55 | | | | | | |
| 4R34 | S | G | S | S | S | N | I | G | S | N | T | F | N | A | D | S | H | R | P | S |
| | | | | | | SEQ ID NO: 52 | | | | | | | | SEQ ID NO: 60 | | | | | | |

| Light-chain variable region name | CDR3 sequence | | | | | | | | | | |
|---|---|---|---|---|---|---|---|---|---|---|---|
| Kabat No. | 89 | 90 | 91 | 92 | 93 | 94 | 95 | 95A | 95B | 96 | 97 |
| | G | T | W | D | A | S | L | S | A | Y | V |
| | | | | | | SEQ ID NO: 61 | | | | | |
| | G | S | W | D | D | S | L | S | A | Y | V |
| | | | | | | SEQ ID NO: 62 | | | | | |
| | D | A | W | D | S | S | L | S | A | Y | V |
| | | | | | | SEQ ID NO: 63 | | | | | |
| | G | T | W | D | D | S | L | S | G | Y | V |
| | | | | | | SEQ ID NO: 64 | | | | | |
| | G | S | W | D | Y | S | L | S | A | Y | V |
| | | | | | | SEQ ID NO: 65 | | | | | |
| | G | S | W | D | Y | S | L | S | A | Y | V |
| | | | | | | SEQ ID NO: 65 | | | | | |
| | A | T | W | D | A | S | L | S | A | Y | V |
| | | | | | | SEQ ID NO: 66 | | | | | |
| | G | T | W | D | D | S | L | N | G | Y | V |
| | | | | | | SEQ ID NO: 67 | | | | | |
| | G | S | W | D | Y | S | L | S | A | Y | V |
| | | | | | | SEQ ID NO: 65 | | | | | |
| | G | T | W | D | Y | S | L | S | G | Y | V |
| | | | | | | SEQ ID NO: 68 | | | | | |

TABLE 7

| Heavy-chain variable region name | sequence | SEQ ID NO: |
|---|---|---|
| 4R14 | EVQLLESGGGLVQPGGSLRLSCAVSGFTFSNYAMSWVRQAPGKGLEWVSAISSGGGNIYYADSVKGRFTISRDNSKNTLYLQMNSLRAEDTAVYYCAKLRRYFDYWGQGTLVTVSS | SEQ ID NO: 1 |
| 4R23 | EVQLLESGGGLVQPGGSLRLSCAASGFTFSDYAMSWVRQAPGKGLEWVSAISSGGSSIYYADSVKGRFTISRDNSKNTLHLQMNSLRAEDTAVYYCARGPQRSATAVFDYWGQGTLVTVSS | SEQ ID NO: 2 |
| 4R25 | EVQLLESGGGLVQPGGSLRLSCAASGFTFSNYAMSWVRQAPGKGLEWVSWISPNSGNIYYADSVKGRFTISRDNSKNTLYLQMNSLRAEDTAVYYCARRPLSAAWSHSSYYNAMDVWGQGTLVTVSS | SEQ ID NO: 3 |
| 4R66 | EVQLLESGGGLVQPGGSLRLSCAASGFTFSGYAMSWVRQAPGKGLEWVSLISHSGSNTYYADSVKGRFTISRDNSKNTLYLQMNSLRAEDTAVYYCARPHRAFDYWGQGTLVTVSS | SEQ ID NO: 4 |
| 4R67 | EVQLLESGGGLVQPGGSLRLSCAASGFTFSNYAMSWVRQAPGKGLEWVSGISHGSGSIYYADSVKGRFTISRDNSKNTLYLQMNSLRAEDTAVYYCARPHRAFDYWGQGTLVTVSS | SEQ ID NO: 5 |
| 4R73 | EVQLLESGGGLVQPGGSLRLSCAASGFTFSNYAMSWVRQAPGKGLEWVSGISHGNGSIYYADSVKGRFTISRDNSKNTLYLQMNSLRAEDTAVYYCAKTGRHFDYWGQGTLVTVSS | SEQ ID NO:6 |
| 4R83 | EVQLLESGGGLVQPGGSLRLSCAASGFTFSNYAMSWVRQAPGKGLEWVSSISPSGSSIYYADSVKGRFTISRDNSKNTLYLQMNSLRAEDTAVYYCARSYRAFDYWGQGTLVTVSS | SEQ ID NO: 7 |
| 4R91 | EVQLLESGGGLVQPGGSLRLSCAASGFTFSNYAMSWVRQAPGKGLEWVSAISPSGGSIYYADSVKGRFTISRDNSKNTLYLQMNSLRAEDTAVYYCARAKRAFDYWGQGTLVTVSS | SEQ ID NO:8 |
| 4R33 | EVQLLESGGGLVQPGGSLRLSCAASGFTFSNYAMSWVRQAPGKGLEWVSAISPGSGSTYYADSVKGRFTISRDNSKNTLYLQMNSLRAEDTAVYYCAKFRRHFDYWGQGTLVTVSS | SEQ ID NO: 9 |
| 4R34 | EVQLLESGGGLVQPFFSLRLSCAASGFTFSNYAMSWVRQAPGKGLEWVSAISSGGGNIYYADSVKGRFTISRDNSKNTLYLQMNSLRAEDTAVYYCARVHRAFDYWGQGTLVTVSS | SEQ ID NO: 10 |

TABLE 8

| Light-chain variable region name | sequence | SEQ ID NO: |
|---|---|---|
| 4R14 | QSVLTQPPSASGTPGQRVTISCSGSSSNIGNNYVNWYQQLPGTAPKLLIYDNSHRPSGVPDRFSGSKSGTSASLAISGLRSEDEADYYCGTWDASLSAYVFGGGTKLTVL | SEQ ID NO: 33 |
| 4R23 | QSVLTQPPSASGTPGQRVTISCSGSSSNIGNNNVSWYQQLPGTAPKLLIYANSKRPSGVPDRFSGSKSGTSASLAISGLRSEDEADYYCGSWDDSLSAYVFGGGTKLTVL | SEQ ID NO: 34 |
| 4R25 | QSVLTQPPSAPGTPGQRVTISCTGSSSNIGSNVNWYQQLPGTAPKLLIYDDSHRPSGVPDRFSGSKSGTSASLAISGLRSEDEADYYCDAWDSSLSAYVFGGGTKLTVL | SEQ ID NO: 35 |
| 4R66 | QSVLTQPPSASGTPGQRVTLSCTGSSSNIGSNYVSWYQQLPGTAPKLLIYADSQRPSGVPDRFSGSKSGTSASLAISGLRSEDEADYYCGTWDDSLSGYVFGGGTKLTVL | SEQ ID NO: 36 |
| 4R67 | QSVLTQPPSASFTPGQRVTISCSSSSSNIGSNYVSWYQQLPGTAPKLLIYSDSHRPSGVPDRFSGSKSGTSASLAISGLRSEDEADYYCGSWDYSLSAYVFGGGTKLTVL | SEQ ID NO: 37 |
| 4R73 | QSVLTQPPSASGTPGQRVTISCTGSSSNIGNNTVSWYQQLPGTAPKLLIYDNSHRPSGVPDRFSGSKSGTSASLAISGLQSEDEADYYCGSWKYSLSAYVFGGGTKLTVL | SEQ ID NO: 38 |
| 4R83 | QSVLTQPPSASGTPGQRVTISCTGSSSNIGNNDVNWYQQLPGTAPKLLIYYDSQRPSGVPDRFSGSKSGTSASLAISGLRSEDEADYYCATWDASLSAYVFGGGTKLTVL | SEQ ID NO: 39 |
| 4R91 | QSVLTQPPSASGTPGQRVTISCSGSSSNIGSNAVNWYQQLPGTAPKLLIYYDNQRPSGVPDRFSGSKSGTSASLAISGLRSEDEADYYCGTWDDSLNGYVFGGGTKLTVL | SEQ ID NO: 40 |
| 4R33 | QSVLTQPPSASGTPGQRVTISCSGSSSNIGNNAVTWYQQLPGTAPKLLIYDDSHRPSGVPDRFSGSKSGTSASLAISGLRSEDEADYYCGSWDYSLSAYVFGGGTKLTVL | SEQ ID NO: 41 |
| 4R34 | QSVLTQPPSASGTPGQRVTISCSGSSSNIGSNTFNWYQQLPGTAPKLLIYADSHRPSGVPDRFSGSKGTSASLAISGLRSEDEADYYCGTWDYSLSGYVLGGGTKLTVL | SEQ ID NO: 42 |

Example 3: IgG Conversion and Identification of Selected Anti-hIL-4Rα Antibodies The 10 antibodies selected in the form of Fab and dupilumab were converted into the form of IgG1, which is a commonly used antibody. The variable regions (VH, VL) of the selected antibody Fab and dupilumab were introduced into a pcDNA3.4 vector encoding the light-chains (CH1, CH2, CH3) and heavy-chain (CL) of IgG1. Dupilumab having an IgG1 constant region was called a "dupilumab analogue". The light and heavy chains of respective antibodies were co-transformed at a ratio of 1:1 into HEK293F cells such that the light- and heavy-chains were expressed together in the cell. The cell incubation supernatant collected according to the transient transfection method was applied to a Protein A Sepharose column and washed with PBS (12 mM phosphate, 137 mM NaCl, 2.7 mM KCl, pH 7.4). The antibody was eluted at pH 3.0 using an 0.1 M glycine and 0.5 M NaCl buffer, and the sample was immediately neutralized using a 1 M Tris buffer.

The buffer was exchanged with a storage buffer (PBS pH 7.4) using a PD-10 desalting column (GE Healthcare) and then the eluted protein was concentrated using a Vivaspin 30,000 MWCO (Sartorius) as a centrifugal concentrator. The absorbance at a wavelength of 562 nm of the purified protein was measured and the amount thereof was quantified using a solution in the BCA protein assay kit (Thermo) according to the drawn standard curve.

Example 4: Verification of Binding Ability of Selected Anti-hIL-4Rα Antibodies The antigen-binding ability (affinity) and specificity of the antibody for the antigen were determined using indirect ELISA. To detect the specificity for the hIL-4Rα antigen protein prepared in <Example 1> above, GST (glutathione S-transferase) protein was immobilized at 50 ng/well in a 96-well plate at room temperature for 1 hour and blocked at room temperature with 0.1% PBST (0.1% Tween20, pH 7.4, 137 mM NaCl, 10 mM Phosphate, 2.7 mM KCl) containing 4% skimmed milk for 1 hour. The solution was discarded and the residue was washed three times with 0.1% PBST and then serially diluted in the range of 50 to 500 nM, each antibody was added at 25 μl to each well in the blocked plate, and the reaction was allowed to progress at room temperature for 1 hour. The solution was discarded and the residue was washed 3 times with 0.1% PBST, and then 25 μl of anti-human IgG-HRP antibody (1:8000) as a secondary antibody was added to each well, followed by reaction at room temperature for 1 hour. The solution was discarded, the residue was washed 3 times with PBST, and 25 μl of TMB solution was added to each well, followed by color development at room temperature for 1 minute. The reaction was stopped with $H_2SO_4$ (1M) and absorbance was measured at 450 nm with an ELISA reader.

As can be seen from the results of FIG. 2, 10 kinds of antibodies have binding specificity for hIL-4Rα and have a wide range of affinity therefor.

Example 5: Evaluation of SEAP Activity Inhibition by IL-Dependent STAT6 Phosphorylation of Selected Anti-hIL-4Rα Antibodies The biological activity of HEK-Blue-IL-4/IL-13 cells (Invivogen) can be compared by monitoring activation of cell signaling by IL-4 or IL-13 through colorimetric analysis. These cells were derived from stable cell lines obtained by transfecting the human STAT6 gene in order to provide a fully activated STAT6 pathway to HEK293 cells that sufficiently express the hIL-4 and hIL-13 receptors. In addition, these cells are transfected with the STAT6-inducible secreted embryonic alkaline phosphatase (SEAP) reporter genes. When hIL-4 or hIL-13 binds to the hIL-4 receptor or hIL-13 receptor expressed on the surface of HEK-Blue-IL-4/IL-13 cells, they activate Tyk2 and JAK1 and recruit and phosphorylate STAT6. Active phosphorylated STAT6 forms a dimer, moves to the nucleus, binds to the promoter of responsive genes, and induces the secretion of SEAP. The secreted SEAP causes a pink substrate, QUANTI-Blue to turn purple (FIG. 3A). The degree of color development has a positive correlation with the amount of hIL-4 and hIL-13 that is present, and the content of hIL-4 and IL-13 can be quantified with reference to a standard. Therefore, these cells enable easy screening as to whether or not anti-IL-4/hIL-4Rα antibodies or anti-IL-13/IL-13Rα1 antibodies block the hIL-4 or hIL-13 signaling pathways.

FIG. 3B shows the result of SEAP secretion of HEK-Blue IL-4/13 cells confirming the hIL-4-signal-blocking effect of constructed anti-hIL-4Rα antibodies compared to that of dupilumab analogues.

Specifically, cells were seeded in an amount of 100 μl at a density of $2.5 \times 10^5$ cells/mL in a 96-well plate in a culture medium (DMEM supplemented with 4.5 g/L glucose (Gibco/Invitrogen), 10% heat-inactivated FBS (Gibco/Invitrogen)), pg/mL blasticidin activated peptidyl nucleoside antibiotics (Invitrogen), 100 μg/mL Zeocin (trade name) and *streptomyces*). On the same day, 50 μl of 200 pM human hIL-4 (Sino Biological) and 50 μl of an anti-hIL-4Rα antibody solution previously diluted to 80 to 400 nM were added and then the 96-well plate was incubated at 37° C. and 5% $CO_2$ for 24 hours. To measure the secreted SEAP, 20 μl of each cell supernatant was added to a transparent 96-well plate and mixed with 180 μl of a QUANTI-Blue solution, and then the 96-well plate was allowed to react at 37° C. for 1 hour and the absorbance at 620 nm was analyzed with a Cytation™ 3 cell Imaging multi-mode reader (FIG. 3B).

The result of analysis showed that all antibodies exhibited a lower hIL-4-signal-blocking effect than the dupilumab analogue, and among them, 4R25 and 4R34 exhibited a high hIL-4-signal-blocking effect (FIG. 3B).

Example 6: Analysis of Binding Ability of Selected Anti-hIL-4Rα Antibodies

In order to more quantitatively analyze the binding ability of 4R25 and 4R34 to hIL-4Rα, SPR (surface plasmon resonance) was performed using a Biacore2000 instrument.

Specifically, hIL-4Rα (Sino Biological) was diluted to a concentration of 50 μl/ml in a 10 mM NaAc buffer (pH 4.0) and immobilized to about 500 response units (RU) on a CM5 sensor chip (GE Healthcare). Then, HBS-EP buffer (10 mM Hepes, 3 mM ethylenediaminetetraacetic acid, and 0.005% surfactant P20 (pH 7.4), GE Healthcare) was analyzed at a flow rate of 30 μl/min, and 4R25 and 4R34 antibodies were analyzed at a concentration of nM to 80 nM. After binding and dissociation analysis, regeneration of the CM5 chip was carried out by flushing the CM5 chip with a buffer solution (10 mM Glycine, pH 2.0) at a flow rate of 30 μl/min for 90 seconds. The sensorgram, obtained by binding for 90 seconds and dissociation for 900 seconds, was normalized and the value of a blank cell was subtracted therefrom to calculate the affinity.

Table 9 shows the results of analysis of affinity of anti-hIL-4Rα antibodies to hIL-4Rα using SPR (BIACORE 2000). 4R25 and 4R34 exhibited high affinity of 1.21 nM and 141 pM, respectively, but this increase in affinity is considered to be due to the improved avidity effect due to antigen immobilization. In this manner, affinity may vary depending on the level of antigen immobilization.

TABLE 9

|  | $K_{on}$ (1/Ms) | $K_{off}$(1/s) | $K_D$(M) |
|---|---|---|---|
| 4R25 | $1.47 \times 10^5$ | $1.77 \times 10^{-4}$ | $1.21 \times 10^{-9}$ |
| 4R34 | $3.51 \times 10^6$ | $4.95 \times 10^{-4}$ | $1.41 \times 10^{-10}$ |

Example 7: Construction of Yeast Cell Surface Expression Library for Increasing 4R34-Based Affinity The 4R34 antibody was superior to 4R25 in the affinity and the ability to inhibit SEAP activity by hIL-4 dependent STAT6 phosphorylation in <Example 5> described above. Therefore, the present inventors aimed to increase the affinity of the anti-hIL-4Rα antibody for hIL-4Rα in order to increase the biological efficacy of the anti-hIL-4Rα antibody.

First, in order to express a single-chain Fab (scFab) on the yeast surface, a 4R34 antibody was constructed in the form of a scFab in a pYDS-H vector (Baek and Kim 2014) treated with a NheI/ApaI restriction enzyme to clone the pYDS 4R34 scFab vector and a pYDS-dummy vector in which a stop codon is generated due to an open reading frame (ORF) shifted due to one additionally introduced nucleotide. By using the pYDS-dummy vector, even if a vector that has not been treated with a restriction enzyme is mixed, only the vector containing the desired library gene can express scFab on the yeast surface.

Regarding the library, random mutations were introduced into the VH-CDR2, VH-CDR3, and VL-CDR3 regions, which are predicted to play an important role in antigen binding, among the six CDRs based on the pYDS 4R34 scFab vector (FIG. 4).

Specifically, mutations were introduced into VH-CDR2 (50, 52-57), VH-CDR3 (95-98), and VL-CDR3 (89, 90, 93, 95A) with low conservation rates, upon comparison between 10 antibody sequences. Spiked oligomers were used to prevent the loss of binding ability to hIL-4Rα because mutations were introduced simultaneously in many regions. This is a mutation method to which all amino acids can be applied while preserving the conventional wild-type 4R34 sequence with 50% probability. It is a technology that ensures 50% of wild-type amino acids during the PCR process by designing primers while maintaining 79% of wild-type nucleotides and 7% of the remaining nucleotides in the three nucleotides encoding amino acids.

Overlapping PCR was performed to prepare 12 µg of the library gene and 4 µg of the pYDS dummy vector treated with NheI/ApaI restriction enzymes. Although the pYDS dummy vector that has not been treated with the restriction enzyme remains and thus is transformed into a yeast strain, it is not expressed on the yeast surface by the stop codon. The two genes were mixed and transformed into a yeast EBY100 (MATa, Trp-) strain for yeast surface expression by electroporation, and constructed through homologous recombination. This process was repeated 10 times, serial dilution was then performed, and then the library size was detected by measuring the number of colonies grown in a SD-CAA+Trp selection medium (20 g/L glucose, 6.7 g/L yeast nitrogen base without amino acids, 5.4 g/L Na$_2$HPO$_4$, 8.6 g/L NaH$_2$PO$_4$, 5 g/L casamino acids, 0.4 mg/L tryptophan). The library that was produced had a size of about $3 \times 10^7$.

Example 8: Kinetic Screening Regarding hIL-4Rα Antigen Protein of Yeast scFab Library In order to select individual clones that bind to hIL-4Rα, clones with higher affinity were selected by competition between biotinylated hIL-4Rα (biotinylated hIL-4Rα) and non-biotin-conjugated hIL-4Rα as a competing protein at a 20 times-higher concentration. FIG. 5 is a schematic diagram showing a strategy for selecting clones with high affinity for hIL-4Rα in the 4R34-based yeast scFab library constructed in <Example 7>.

Specifically, 1 ml of 100 nM biotinylated hIL-4Rα was bound to scFab ($1 \times 10^8$ scFab yeast) expressed in yeast cells at room temperature for 30 minutes, and then PE-conjugated streptavidin (Streptavidin-R-phycoerythrin, (SA-PE), Thermo) and Alexa 488 conjugated anti-IgG antibody (goat Alexa 488-conjugated anti-Fc antibody, Thermo) were bound at 4° C. for 15 minutes, and then clones expressing a high amount of scFab and having high binding ability to biotinylated hIL-4Rα were selected using FACS (fluorescence-activated cell sorting).

In the secondary FACS, 1 ml of 10 nM biotinylated hIL-4Rα was bound to $2 \times 10^7$ scFab yeast at room temperature for 30 minutes, and then the result was washed with 1 ml autoMACS® Running Buffer (phosphate-buffered saline (PBS), bovine serum albumin (BSA), EDTA, and 0.09% azide, pH7.2, Miltenyi Biotec), and made to compete with 1 ml of 200 nM hIL-4Rα unconjugated with biotin at room temperature for 4 hours, to select the top 0.1% clones with the highest binding ability. Subsequently, in the tertiary FACS, 1 ml of 1 nM biotinylated hIL-4Rα was bound to $1 \times 10^7$ scFab yeast at room temperature for 30 minutes, and then the top 0.2% pool was selected. Subsequently, in the quaternary FACS, 1 ml of 1 nM hIL-4Rα was bound to $1 \times 10^7$ scFab yeast at 25° C. for 30 minutes, and the result was washed with 1 ml autoMACS® Running Buffer, and made to compete with 1 ml of 20 nM hIL-4Rα unconjugated with biotin at room temperature for 4 hours, and the top 0.1% clones having the highest binding ability were selected (FIG. 6).

Four individual clones (4R34.1, 4R34.2, 4R34.19, 4R34.29) having high binding ability to hIL-4Rα were isolated from the yeast cell surface through the above selection method.

Additionally, whether or not anti-hIL-4Rα scFab binds to hIL-4 competitively against biotinylated hIL-4Rα on the yeast surface was determined. For this purpose, a full-length hIL-4 cDNA (His25-Ser153) in which DNA encoding an hIL-4 secretion signal peptide is fused with the 5' end of pcDNA3.4, which is an animal expression vector containing a murine heavy-chain constant region (Hinge-CH2-CH3, mFc), was cloned into NotI/ApaI, to construct a vector for expressing the hIL-4-mFc protein (FIG. 7A).

Proteins were expressed and purified using transient transfection. In a shake flask, HEK293F cells suspension-grown in serum-free FreeStyle 293 expression medium were transfected with a mixture of plasmid and polyethyleneimine (PEI). Upon 100 mL transfection into the shake flask, HEK293F cells were seeded in 90 ml of medium at a density of $1.0 \times 10^6$ cells/ml and incubated at 120 rpm, 8% CO$_2$, and 37° C. The plasmid was diluted to 125 µg in 5 ml FreeStyle 293 expression medium and filtered, and PEI 375 µg (7.5

µg/ml) was mixed with 5 ml of diluted medium and allowed to react at room temperature for 10 minutes. Then, the reacted mixed medium was added to the cells seeded in 90 ml and incubated at 120 rpm and 8% $CO_2$ for 6 days. Proteins were purified from the cell incubation supernatant, which was collected with reference to standard protocols. The antibody was applied to a Protein A Sepharose column and washed with PBS (pH 7.4). The antibody was eluted at pH 3.0 using 0.1 M glycine and 0.5 M NaCl buffer, and the sample was immediately neutralized using a 1 M Tris buffer. The eluted antibody fraction was concentrated by exchanging the buffer with PBS (pH 6.5) through a dialysis method. The absorbance of the purified protein at a wavelength of 562 nm was measured, and the amount thereof was quantified using a solution in the BCA protein assay kit (Thermo) according to the drawn standard curve. The purity was detected through SDS-PAGE analysis (FIG. 7B).

Specifically, 1 nM biotinylated hIL-4Rα or 20 nM hIL-4-mFc protein fused with biotinylated hIL-4Rα was bound to scFab yeast at room temperature for 30 minutes. Then, SA-PE was bound thereto at 4° C. for 15 minutes, and the extent of binding to biotinylated hIL-4Rα was analyzed through flow cytometry (FIG. 8).

Tables 10 and 11 show the heavy-chain variable-region sequences and CDR sequences of four individual clones having high binding ability to the selected hIL-4Rα, and Tables 12 and show the light-chain variable-region sequences and CDR sequences.

TABLE 10

| Heavy-chain variable region name | sequence | SEQ ID NO: |
|---|---|---|
| 4R34.1 | EVQLLESGGGLVQPGGSLRLSCAASGFTFSNYAMSWVRQAPGKGLEWVSAITSSGRSIYYADSVKGRFTISRDNSKNTLYLQMNSLRAEDTAVYYCARVHRAFDYWGQGTLVTVSS | SEQ ID NO: 69 |
| 4R34.2 | EVQLLESGGGLVQPGGSLRLSCAASGFTFSNYAMSWVRQAPGKGLEWVSAITSSGANIYYADSVKGRFTISRDNSKNTLYLQMNSLRAEDTAVYYCARVHRAFDYWGQGTLVTVSS | SEQ ID NO: 70 |
| 4R34.19 | EVQLLESGGGLVQPGGSLRLSCAASGFTFSNYAMSWVRQAPGKGLEWVSAITSSGGNIYYADSVKGRFTISRDNSKNTLYLQMNSLRAEDTAVYYCARVHRAFDYWGQGTLVTVSS | SEQ ID NO: 71 |
| 4R34.29 | EVQLLESGGGLVQPGGSLRLSCAASGFTFSNYAMSWVRQAPGKGLEWVSAITAGGGSIYYADSVKGRFTISRDNSKNTLYLQMNSLRAEDTAVYYCARVHRAFDYWGQGTLVTVSS | SEQ ID NO: 72 |

TABLE 11

| Heavy-chain variable region name | CDR1 sequence | | | | | CDR2 sequence | | | | | | | | | | | | | | CDR3 sequence | | | | | | | |
|---|---|---|---|---|---|---|---|---|---|---|---|---|---|---|---|---|---|---|---|---|---|---|---|---|---|---|---|
| Kabat No. | 31 | 32 | 33 | 34 | 35 | 50 | 51 | 52 | 52a | 53 | 54 | 55 | 56 | 57 | 58 | 59 | 60 | 61 | 62 | 63 | 64 | 65 | 95 | 96 | 97 | 98 | 99 | 101 | 102 |
| 4R34.1 | N | Y | A | M | S | A | I | T | S | S | G | R | S | I | Y | Y | A | D | S | V | K | G | V | H | R | A | F | D | Y |
|  | SEQ ID NO: 11 | | | | | SEQ ID NO: 73 | | | | | | | | | | | | | | | | | SEQ ID NO: 32 | | | | | | |
| 4R34.2 | N | Y | A | M | S | A | I | T | S | S | G | A | N | I | Y | Y | A | D | S | V | K | G | V | H | R | A | F | D | Y |
|  | SEQ ID NO: 11 | | | | | SEQ ID NO: 74 | | | | | | | | | | | | | | | | | SEQ ID NO: 32 | | | | | | |
| 4R34.19 | N | Y | A | M | S | A | I | T | S | S | G | G | N | I | Y | Y | A | D | S | V | K | G | V | H | R | A | F | D | Y |
|  | SEQ ID NO: 11 | | | | | SEQ ID NO: 75 | | | | | | | | | | | | | | | | | SEQ ID NO: 32 | | | | | | |
| 4R34.29 | N | Y | A | M | S | A | I | T | A | G | G | G | S | I | Y | Y | A | D | S | V | K | G | V | H | R | A | F | D | Y |
|  | SEQ ID NO: 11 | | | | | SEQ ID NO: 76 | | | | | | | | | | | | | | | | | SEQ ID NO: 32 | | | | | | |

TABLE 12

| Light-chain variable region name | sequence | SEQ ID NO: |
|---|---|---|
| 4R34.1 | QSVLTQPPSASGTPGQRVTISCSGSSSNIGSNTFNWYQQLPGTAPKLLIYADSHRPSGVPDRFSGSKSGTSASLAISGLRSEDEADYYCGTWDYSLSGYVLGGGTKLTVL | SEQ ID NO: 77 |
| 4R34.2 | QSVLTQPPSASGTPGQRVTISCSGSSSNIGSNTFNWYQQLPGTAPKLLIYADSHRPSGVPDRFSGSKSGTSASLAISGLRSEDEADYYCGTWDYSLRGYVLGGGTKLTVL | SEQ ID NO: 78 |

TABLE 12-continued

| Light-chain variable region name | sequence | SEQ ID NO: |
|---|---|---|
| 4R34.19 | QSVLTQPPSASGTPGQRVTISCSGSSSNIGSNTFNWYQQLPGTAPKLLIYADSHRPSG VPDRFSGSKSGTSASLAISGLRSEDEADYYCGYWDYSLSGYVLGGGTKLTVL | SEQ ID NO: 79 |
| 4R34.29 | QSVLTQPPSASGTPGQRVTISCSGSSSNIGSNTFNWYQQLPGTAPKLLIYADSHRPSG VPDRFSGSKSGTSASLAISGLRSEDEADYYCGTWDYSLSGYVLGGGTKLTVL | SEQ ID NO: 80 |

TABLE 13

| Light-chain variable region name | CDR1 sequence | | | | | | | | | | | CDR2 sequence | | | | | | |
|---|---|---|---|---|---|---|---|---|---|---|---|---|---|---|---|---|---|---|
| Kabat No. | 24 | 25 | 26 | 27 | 27a | 27b | 28 | 29 | 30 | 31 | 32 | 33 | 34 | 50 | 51 | 52 | 53 | 54 | 55 | 56 |
| 4R34.1 | S | G | S | S | S | | N | I | G | S | N | T | F | N | A | D | S | H | R | P | S |
| | | | | | | | SEQ ID NO: 52 | | | | | | | | | | SEQ ID NO: 60 | | | |
| 4R34.2 | S | G | S | S | S | | N | I | G | S | N | T | F | N | A | D | S | H | R | P | S |
| | | | | | | | SEQ ID NO: 52 | | | | | | | | | | SEQ ID NO: 60 | | | |
| 4R34.19 | S | G | S | S | S | | N | I | G | S | N | T | F | N | A | D | S | H | R | P | S |
| | | | | | | | SEQ ID NO: 52 | | | | | | | | | | SEQ ID NO: 60 | | | |
| 4R34.29 | S | G | S | S | S | | N | I | G | S | N | T | F | N | A | D | S | H | R | P | S |
| | | | | | | | SEQ ID NO: 52 | | | | | | | | | | SEQ ID NO: 60 | | | |

| Light-chain variable region name | CDR3 sequence | | | | | | | | | | |
|---|---|---|---|---|---|---|---|---|---|---|---|
| Kabat No. | 89 | 90 | 91 | 92 | 93 | 94 | 95 | 95a | 95b | 96 | 97 |
| 4R34.1 | G | T | W | D | Y | S | L | S | G | Y | V |
| | | | | | SEQ ID NO: 68 | | | | | | |
| 4R34.2 | G | T | W | D | Y | S | L | R | G | Y | V |
| | | | | | SEQ ID NO: 81 | | | | | | |
| 4R34.19 | G | T | W | D | Y | S | L | S | G | Y | V |
| | | | | | SEQ ID NO: 82 | | | | | | |
| 4R34.29 | G | T | W | D | Y | S | L | S | G | Y | V |
| | | | | | SEQ ID NO: 68 | | | | | | |

Example 9: Analysis of Binding Ability of Antibodies having improved affinity based on 4R34 and evaluation of SEAP activity inhibition thereof by IL-4-dependent STAT6 phosphorylation Selected clones (4R34.1, 4R34.2, 4R34.19, 4R34.29) were each inserted into a pcDNA3.4 vector having light and heavy chains. The two vectors were simultaneously transiently transfected at a ratio of 1:1 into HEK293F protein-expressing cells such that the light and heavy chains were expressed together in the cells.

In order to quantitatively analyze the binding ability thereof to hIL-4Rα, SPR (surface plasmon resonance) was performed using a Biacore2000 instrument.

Specifically, hIL-4Rα (Sino Biological) was diluted to a concentration of 50 µl/ml in 10 mM NaAc buffer (pH 4.0) and immobilized to about 80 response units (RU) on a CM5 sensor chip (GE Healthcare). Then, HBS-EP buffer (10 mM Hepes, 3 mM ethylenediaminetetraacetic acid, and 0.005% surfactant P20 (pH 7.4), GE Healthcare) was analyzed at a flow rate of 30 µl/min, and 4R25 and 4R34 antibodies were analyzed at a concentration of nM to 80 nM. After binding and dissociation analysis, regeneration of the CM5 chip was carried out by flushing the CM5 chip with a buffer solution (10 mM Glycine, pH 2.0) at a flow rate of 30 µl/min for 90 seconds. The sensorgram obtained by binding for 90 seconds and dissociation for 900 seconds was normalized, and the value of a blank cell was subtracted therefrom to calculate the affinity.

Table 14 shows the results of analysis of affinity of anti-hIL-4Rα antibodies (4R34.1, 4R34.2, 4R34.19, 4R34.29) to hIL-4Rα using SPR (BIACORE 2000). 4R34 exhibited affinity of 3.8 nM lower than before, but this is considered to be due to the difference from other hIL-4a immobilization. Among the selected clones, 4R34.1 exhibited the highest affinity of 18.2 pM, and 4R34.2, 4R34.19, and 4R34.29 also exhibited high affinity of 131 pM to 313 pM.

TABLE 14

|  | $K_a$ (M$^{-1}$S$^{-1}$) | $K_b$(S$^{-1}$) | $K_D$(M) |
|---|---|---|---|
| 4R34 | $3.64 \times 10^5$ | $1.38 \times 10^{-3}$ | $3.8 \times 10^{-9}$ |
| 4R34.1 | $6.91 \times 10^7$ | $1.26 \times 10^{-3}$ | $1.82 \times 10^{-11}$ |
| 4R34.2 | $8.82 \times 10^6$ | $2.62 \times 10^{-3}$ | $2.97 \times 10^{-10}$ |
| 4R34.19 | $4.18 \times 10^6$ | $1.31 \times 10^{-3}$ | $3.13 \times 10^{-10}$ |
| 4R34.29 | $6.32 \times 10^6$ | $8.29 \times 10^{-4}$ | $1.31 \times 10^{-10}$ |

SEAP activity inhibition by HIL-4-dependent STAT6 phosphorylation was evaluated in the same manner as in <Example 5> using clones with increased affinity (4R34.1, 4R34.2, 4R34.19, 4R34.29) and using 4R34, which was used as a library template, as a control group.

Specifically, cells were seeded in an amount of 100 μl at a density of $2.5 \times 10^5$ cells/mL in each well of a 96-well plate in a culture medium (DMEM supplemented with 4.5 g/L glucose (Gibco/Invitrogen), 10% heat-inactivated FBS (Gibco/Invitrogen)), pg/mL blasticidin activated peptidyl nucleoside antibiotics (Invitrogen), 100 μg/mL Zeocin (trade name) and *streptomyces*). On the same day, 50 μl of 200 pM human hIL-4 (Sino Biological) and 50 μl of an anti-hIL-4Rα antibody solution previously diluted to 40 to 200 nM were added, and then the 96-well plate was incubated at 37° C. and 5% CO$_2$ for 24 hours. To measure the secreted SEAP, 20 μl of each cell supernatant was added to a transparent 96-well plate and mixed with 180 μl of a QUANTI-Blue solution, after which the 96-well plate was allowed to react at 37° C. for 1 hour and the absorbance at 620 nm was analyzed with a Cytation™ 3 cell Imaging multi-mode reader (FIG. 3B).

The result of analysis showed that all anti-hIL-4Rα antibodies with improved affinity exhibited a higher hIL-4-signal-blocking effect than the 4R34 used as a template, and among them, the 4R34.1 antibody exhibited the highest hIL-4-signal-blocking effect (FIG. 9).

Example 10: Construction and Selection of High-Diversity Antibody Library for Additional Affinity Improvement Based on 4R34.1 Antibody Because it was determined that the ability to inhibit SEAP activity by hIL-4-dependent STAT6 phosphorylation can be increased by improving affinity, affinity and SEAP activity inhibition by hIL-4-dependent STAT6 phosphorylation were increased by modifying (improving) VH-CDR1 and VH-CDR1 not used in Example 7.

Specifically, similar to Example 7, mutations were introduced into VH-CDR1 (31-35) and VH-CDR1 (27-32) using a degeneration codon (NNK) in which all 20 amino acids can be arranged and using the pYDS 4R34.1 vector as a template (FIG. 10).

Overlapping PCR was performed to prepare 12 μg of the library gene and 4 μg of the pYDS dummy vector treated with NheI/ApaI restriction enzymes. The two genes were mixed and transformed into an EBY100 (MATa, Trp-) yeast strain for yeast surface expression by electroporation, and constructed through homologous recombination. This process was repeated 10 times, serial dilution was performed, and then the library size was detected by measuring the number of colonies grown in a SD-CAA+Trp selection medium (20 g/L glucose, 6.7 g/L yeast nitrogen base without amino acids, 5.4 g/L Na$_2$HPO$_{24}$, 8.6 g/L NaH$_2$PO$_2$, 5 g/L casamino acids, 0.4 mg/L tryptophan).

In the primary FACS, 1 ml of 1 pM biotinylated hIL-4Rα was allowed to react with $1 \times 10^8$ scFab yeast at room temperature for 30 minutes. In the secondary FACS, 1 ml of 2 nM biotinylated hIL-4Rα was allowed to react with $1 \times 10^8$ scFab yeast at room temperature for 30 minutes, and then the result was washed with 1 ml autoMACS® Running Buffer and made to compete with 10 ml of 200 nM hIL-4Rα unconjugated with biotin at room temperature for hours. In the tertiary and quaternary FACS, 1 ml of 1 nM biotinylated hIL-4Rα was bound to $1 \times 10^8$ scFab yeast at room temperature for 30 minutes, washed with 1 ml autoMACS® Running Buffer, and made to compete with 1 ml of 100 nM hIL-4Rα unconjugated with biotin at room temperature for 2 hours to select clones having high binding ability.

After the final quaternary FACS, individual clones having high binding ability to hIL-4Rα were classified according to the PE signal, and clones called "4R34.1.11", "4R34.1.13", "4R34.1.17", "4R34.1.18", "4R34.1.19", and "4R34.1.21" were selected.

The six clones were converted to IgG in Example 3 above and identified. Tables 15 and 16 show the heavy-chain variable-region sequences and CDR sequences of selected six individual clones having high binding ability to hIL-4Rα, and Tables 17 and show the light-chain variable-region sequences and CDR sequences.

TABLE 15

| Heavy-chain variable region name | sequence | SEQ ID NO: |
|---|---|---|
| 4R34.1.19 | EVQLLESGGGLVQPGGSLRLSCAASGFTFSRHAMAWVRQAPGK GLEWVSAITSSGRSIYYADSVKGRFTISRDNSKNTLYLQMNSL RAEDTAVYYCARVHRAFDYWGQGTLVTVSS | SEQ ID NO: 83 |

TABLE 16

| Heavy-chain variable region name | CDR1 sequence | | | | | CDR2 sequence | | | | | | | | | | | | CDR3 sequence | | | | | | | |
|---|---|---|---|---|---|---|---|---|---|---|---|---|---|---|---|---|---|---|---|---|---|---|---|---|---|
| Kabat No. | 31 | 32 | 33 | 34 | 35 | 50 | 51 | 52 | 52a | 53 | 54 | 55 | 56 | 57 | 58 | 59 | 60 | 61 | 62 | 63 | 64 | 65 | 95 | 96 | 97 | 98 | 99 | 101 | 102 |
| 4R34.1.19 | R SEQ ID No: 84 | H | A | M | A | A SEQ ID No: 85 | I | T | S | S | G | R | S | I | Y | Y | A | D | S | V | K | G | V SEQ ID No: 32 | H | R | A | F | D | Y |

TABLE 17

| Light-chain variable region name | sequence | SEQ ID NO: |
|---|---|---|
| 4R34.1.11 | QSVLTQPPSASGTPGQRVTISCSGSSANSRTDGFNWYQQLPGTAPKLLIYADSHRPSGVPDRFSGSKSGTSASLAISGLRSEDEADYYCGTWDYSLSGYVLGGGTKLTVLG | SEQ ID NO: 86 |
| 4R34.1.13 | QSVLTQPPSASGTPGQRVTISCSGSAQFGSRDNFNWYQQLPGTAPKLLIYADSHRPSGVPDRFSGSKSGTSASLAISGLRSEDEADYYCGTWDYSLSGYVLGGGTKLTVLG | SEQ ID NO: 87 |
| 4R34.1.17 | QSVLTQPPSASGTPGQRVTISCSGSTKQMHNYQFNWYQQLPGTAPKLLIYADSHRPSGVPDRFSGSKSGTSASLAISGLRSEDEADYYCGTWDYSLSGYVLGGGTKLTVLG | SEQ ID NO: 88 |
| 4R34.1.18 | QSVLTQPPSASGTPGQRVTISCSGSLLRGENLQFNWYQQLPGTAPKLLIYADSHRPSGVPDRFSGSKSGTSASLAISGLRSEDEADYYCGTWDYSLSGYVLGGGTKLTVLG | SEQ ID NO: 89 |
| 4R34.1.19 | QSVLTQPPSASGTPGQRVTISCSGSPLFPDSGSFNWYQQLPGTAPKLLIYADSHRPSGVPDRFSGSKSGTSASLAISGLRSEDEADYYCGTWDYSLSGYVLGGGTKLTVLG | SEQ ID NO: 90 |
| 4R34.1.21 | QSVLTQPPSASGTPGQRVTISCSGSAALDLSPSFNWYQQLPGTAPKLLIYADSHRPSGVPDRFSGSKSGTSASLAISGLRSEDEADYYCGTWDYSLSGYVLGGGTKLTVLG | SEQ ID NO: 91 |

TABLE 18

| Light-chain variable region name | CDR1 sequence | | | | | | | | | | | | CDR2 sequence | | | | | |
|---|---|---|---|---|---|---|---|---|---|---|---|---|---|---|---|---|---|---|
| Kabat No. | 24 | 25 | 26 | 27 | 27a | 27b | 28 | 29 | 30 | 31 | 32 | 33 | 34 | 50 | 51 | 52 | 53 | 54 | 55 | 56 |
| 4R34.1.11 | S | G | S | S | A | N SEQ ID No: 92 | S | R | T | D | G | F | N | A | D SEQ ID No: 60 | S | H | R | P | S |
| 4R34.1.13 | S | G | S | A | Q | F SEQ ID No: 93 | G | S | R | D | N | F | N | A | D SEQ ID No: 60 | S | H | R | P | S |
| 4R34.1.17 | S | G | S | T | K | Q SEQ ID No: 94 | M | H | N | Y | Q | F | N | A | D SEQ ID No: 60 | S | H | R | P | S |
| 4R34.1.18 | S | G | S | L | L | R SEQ ID No: 95 | G | E | N | L | Q | F | N | A | D SEQ ID No: 60 | S | H | R | P | S |
| 4R34.1.19 | S | G | S | P | L | F SEQ ID No: 96 | P | D | S | G | S | F | N | A | D SEQ ID No: 60 | S | H | R | P | S |
| 4R34.1.21 | S | G | S | A | L | D SEQ ID No: 97 | L | S | P | S | F | N | A | D SEQ ID No: 60 | S | H | R | P | S |

TABLE 18-continued

| Light-chain variable region name | CDR3 sequence | | | | | | | | | | |
|---|---|---|---|---|---|---|---|---|---|---|---|
| Kabat No. | 89 | 90 | 91 | 92 | 93 | 94 | 95 | 95a | 95b | 96 | 97 |
| 4R34.1.11 | G | T | W | D | Y | S | L | S | G | Y | V |
| SEQ ID No: 68 | | | | | | | | | | | |
| 4R34.1.13 | G | T | W | D | Y | S | L | S | G | Y | V |
| SEQ ID No: 68 | | | | | | | | | | | |
| 4R34.1.17 | G | T | W | D | Y | S | L | S | G | Y | V |
| SEQ ID No: 68 | | | | | | | | | | | |
| 4R34.1.18 | G | T | W | D | Y | S | L | S | G | Y | V |
| SEQ ID No: 68 | | | | | | | | | | | |
| 4R34.1.19 | G | T | W | D | Y | S | L | S | G | Y | V |
| SEQ ID No: 68 | | | | | | | | | | | |
| 4R34.1.21 | G | T | W | D | Y | S | L | S | G | Y | V |
| SEQ ID No: 68 | | | | | | | | | | | |

Example 11: Biochemical/Biological Evaluation for Antibody Selection

<Evaluation of Competitive Binding of Antibodies and human hIL-4 to hIL-4Rα>

Binding competition ELISA was performed to determine whether or not anti-hIL-4Rα antibodies compete with hIL-4 for hIL-4Rα binding sites as a criterion for selecting anti-hIL-4Rα antibodies with high biological efficacy.

Specifically, the hIL-4Rα protein purified in Example 1 was immobilized in a 96-well plate at a concentration of 50 ng/well at room temperature for 1 hour and blocked with 0.1% PBST containing 4% BSA (Bovine Serum Albumin) at room temperature for 1 hour. The solution was discarded, the residue was washed 3 times with 0.1% PBST, and a mixture of hIL-4-mFc [27 nM] and anti-hIL-4Rα antibody at different concentrations [20 nM, 100 nM, 500 nM] was prepared, added in an amount of 25 μl to each well of a blocked plate and allowed to react at room temperature for 1 hour. The solution was discarded, the residue was washed times with 0.1% PBST, and an anti-mouse IgG-HRP antibody (1:4000) as a secondary antibody was added in an amount of 25 μl to each well and allowed to react at room temperature for 1 hour. The solution was discarded, the residue was washed 3 times with PBST, and a TMB solution was added in an amount of 25 μl to each well, followed by color development at room temperature for 1 minute 30 seconds. The reaction was stopped with $H_2SO_4$ (1M), and the absorbance at 450 nm was measured with an ELISA reader. The results of ELISA showed that all anti-hIL-4Rα antibodies and hIL-4-mFc competed to bind to hIL-4R, and there was no notable difference in the competitive ability between anti-hIL-4Rα antibodies (FIG. 11).

<Affinity Evaluation>

Table 19 shows the results of analysis of affinity of antibodies to hIL-4Rα using SPR.

TABLE 19

| | $K_a$ (M$^{-1}$S$^{-1}$) | $K_b$(S$^{-1}$) | $K_D$(M) |
|---|---|---|---|
| 4R34.1 | 3.64 × 10$^6$ | 6.02 × 10$^{-4}$ | 1.66 × 10$^{-10}$ |
| 4R34.1.11 | 3.76 × 10$^6$ | 3.07 × 10$^{-4}$ | 8.15 × 10$^{-11}$ |
| 4R34.1.13 | 4.1 × 10$^6$ | 3.1 × 10$^{-4}$ | 7.56 × 10$^{-11}$ |

TABLE 19-continued

| | $K_a$ (M$^{-1}$S$^{-1}$) | $K_b$(S$^{-1}$) | $K_D$(M) |
|---|---|---|---|
| 4R34.1.17 | 4.02 × 10$^6$ | 4.13 × 10$^{-4}$ | 1.03 × 10$^{-10}$ |
| 4R34.1.18 | 4.57 × 10$^6$ | 4.84 × 10$^{-4}$ | 1.06 × 10$^{-10}$ |
| 4R34.1.19 | 3.93 × 10$^6$ | 5.2 × 10$^{-4}$ | 1.32 × 10$^{-10}$ |
| 4R34.1.21 | 3.03 × 10$^6$ | 3.6 × 10$^{-4}$ | 1.19 × 10$^{-10}$ |

Specifically, hIL-4Rα (Sino Biological) was diluted to a concentration of 50 μl/ml in a 10 mM NaAc buffer (pH 4.0) and immobilized to about 200 response units (RU) on a CM5 sensor chip (GE Healthcare). Then, analysis was performed in HBS-EP buffer (10 mM Hepes, 3 mM ethylenediaminetetraacetic acid, and 0.005% surfactant P20 (pH 7.4), GE Healthcare) at a flow rate of μl/min, and 4R34.1, 4R34.1.11, 4R34.1.13, 4R34.1.17, 4R34.1.18, 4R34.1.19, 4R34.1.21 and dupilumab analogue antibodies were analyzed at a concentration of 1 nM to 80 nM. After binding and dissociation analysis, regeneration of the CM5 chip was carried out by flushing the CM5 chip with a buffer solution (10 mM Glycine, pH 2.0) at a flow rate of 30 μl/min for 90 seconds. The sensorgram obtained by binding for 90 seconds and dissociation for 360 seconds was normalized, and the value of a blank cell was subtracted therefrom to calculate the affinity.

The affinity of the newly derived antibodies for hIL-4Rα was found not to be greatly different from that of 4R34.1.

<Evaluation of SEAP Activity Inhibition by hIL-4-Dependent STAT6 Phosphorylation>

The hIL-4-signal-blocking effect of anti-hIL-4Rα antibodies was detected by measuring SEAP secretion of HEK-Blue IL-4/13 cells in the same manner as in Example 5 using, as a control group, 4R34.1 used as a library template with respect to 4R34.1.11, 4R34.1.13, 4R34.1.17, 4R34.1.18, 4R34.1.19 and 4R34.1.21 antibodies.

Specifically, cells were seeded in an amount of 100 μl at a density of 2.5×10$^5$ cells/mL in each well of a 96-well plate in a culture medium (DMEM supplemented with 4.5 g/L glucose (Gibco/Invitrogen), 10% heat-inactivated FBS (Gibco/Invitrogen)), pg/mL blasticidin activated peptidyl nucleoside antibiotics (Invitrogen), 100 μg/mL Zeocin (trade name) and *streptomyces*). On the same day, 50 μl of 200 pM human hIL-4 (Sino Biological) and 50 μl of an anti-hIL-4Rα antibody solution previously diluted to 40 to 200 nM were added, and then the 96-well plate was incubated at 37° C. and 5% $CO_2$ for 24 hours. To measure the secreted SEAP, 20 μl of each cell supernatant was added to a transparent 96-well plate and mixed with 180 μl of a QUANTI-Blue solution, and then the 96-well plate was allowed to react at 37° C. for 1 hour and the absorbance at 620 nm was analyzed with a Cytation™ 3 cell Imaging multi-mode reader.

The result of the analysis showed that all anti-hIL-4Rα antibodies with increased affinity had higher hIL-4-signal-blocking effects than a 4R34.1 antibody used as a template at concentrations of 20 to 100 nM, and among them, the 4R34.1.17 and 4R34.1.19 antibodies exhibited the highest hIL-4-signal-blocking effect (FIG. 12).

<Evaluation of SEAP Activity Inhibition by hIL-13-Dependent STAT6 Phosphorylation>

The hIL-13-signal-blocking effect of anti-hIL-4Rα antibodies was detected by measuring SEAP secretion of HEK-Blue IL-4/13 cells using, as a control group, 4R34.1 used as a library template with respect to 4R34.1.17 and 4R34.1.19 antibodies, which had high ability to neutralize hIL-4.

Specifically, cells were seeded in an amount of 100 μl at a density of $2.5 \times 10^5$ cells/mL in each well of a 96-well plate in a culture medium (DMEM supplemented with 4.5 g/L glucose (Gibco/Invitrogen), 10% heat-inactivated FBS (Gibco/Invitrogen)), 10 μg/mL blasticidin activated peptidyl nucleoside antibiotics (Invitrogen), 100 μg/mL Zeocin (trade name) and *streptomyces*). On the same day, 50 μl of 2 nM human hIL-13 (Peprotech) and 50 μl of an anti-hIL-4Rα antibody solution previously diluted to 40 to 200 nM were added, and then the 96-well plate was incubated at 37° C. and 5% $CO_2$ for 24 hours. To measure the secreted SEAP, 20 μl of each cell supernatant was added to a transparent 96-well plate and mixed with 180 μl of a QUANTI-Blue solution, and then the 96-well plate was allowed to react at 37° C. for 1 hour and the absorbance at 620 nm was analyzed with a Cytation™ 3 cell Imaging multi-mode reader.

The result of the analysis showed that anti-hIL-4Rα antibodies with increased affinity had higher effect of blocking the signal of 1 nM hIL-13 than dupilumab analogues (FIG. 13).

Since hIL-13 is present in a very low amount of 78.5+/−64.5 μg/ml in the serum of asthma patients, it can be expected that administration thereof to asthma patients will have similar effects to dupilumab.

Example 12: Verification of hIL-4Rα-Specific Binding Ability for Final Antibody Selection In order to detect the specificity for hIL-4Rα, the hIL-4Rα-specific binding of the hIL-4Rα antibody was detected by FACS using the THP-1 cell line expressing hIL-4Rα (hIL-4Rα positive) and the Molt-4 cell line not expressing hIL-4Rα (hIL-4Rα negative).

Specifically, $2 \times 10^5$ cells/90 μl of THP-1 and Molt-4 cells and 1 μg of hIgG (10 mg/ml) with respect to each sample were mixed and allowed to react at 4° C. for 20 minutes to block Fcγ receptors. Non-specific binding of the anti-hIL-4Rα antibody to the heavy-chain region can be excluded through this process. Then, 10 μl of 40 to 1,000 nM anti-hIL-4Rα antibodies were added to adjust the final concentration to 4 to 100 nM, followed by reaction at 4° C. for 30 minutes and washing with cold PBS (pH 7.4). Anti-human IgG Fcγ-specific F(ab')2 secondary antibody conjugated with Alexa fluor 488 recognizing human IgG (Jackson ImmunoResearch) was allowed to react at 4° C. for 30 minutes (pH 7.4), washed, and analyzed with a FACS Calibur (BD Bioscience) flow cytometer. After analysis, a histogram graph for each sample was obtained.

The result of analysis showed that the 4R34.1.17 and 4R34.1.19 antibodies exhibited improved binding ability to hIL-4Rα in THP-1 than the control 4R34.1 antibody (FIG. 14). However, the 4R34.1.17 antibody was also bound to the Molt-4 cell line in which hIL-4Rα was not expressed and thus had no specificity for hIL-4Rα (FIG. 14). Thus, it was confirmed that the 4R34.1.19 antibody has improved hIL-4Rα-specific binding ability than that of 4R34.1, thereby blocking IL-4 signaling.

Example 13: Epitope Mapping of 4R34.1.19 Antibody

TABLE 20

SEQ ID NO: 98

| | | | | | | | | | | | | | | | | | | | |
|---|---|---|---|---|---|---|---|---|---|---|---|---|---|---|---|---|---|---|---|
| Met | Gly | Trp | Leu | Cys | Ser | Gly | Leu | Leu | Phe | Pro | Val | Ser | Cys | Leu | Val | Leu | Leu | Gln | Val |
| 1 | | | | 5 | | | | | 10 | | | | | 15 | | | | | 20 |
| Ala | Ser | Ser | Gly | Asn | Met | Lys | Val | Leu | Gln | Glu | Pro | Thr | Cys | Val | Ser | Asp | Tyr | Met | Ser |
| 21 | | | | 25 | | | | | 30 | | | | | 35 | | | | | 40 |
| Ile | Ser | Thr | Cys | Glu | Trp | Lys | Met | Asn | Gly | Pro | Thr | Asn | Cys | Ser | Thr | Glu | Leu | Arg | Leu |
| 41 | | | | 45 | | | | | 50 | | | | | 55 | | | | | 60 |
| Leu | Tyr | Gln | Leu | Val | Phe | Leu | Leu | Ser | Glu | Ala | His | Thr | Cys | Ile | Pro | Glu | Asn | Asn | Gly |
| 61 | | | | 65 | | | | | 70 | | | | | 75 | | | | | 80 |
| Gly | Ala | Gly | Cys | Val | Cys | His | Leu | Leu | Met | Asp | Asp | Val | Val | Ser | Ala | Asp | Asn | Tyr | Thr |
| 81 | | | | 85 | | | | | 90 | | | | | 95 | | | | | 100 |
| Leu | Asp | Leu | Trp | Ala | Gly | Gln | Gln | Leu | Leu | Trp | Lys | Gly | Ser | Phe | Lys | Pro | Ser | Glu | His |
| 101 | | | | 105 | | | | | 110 | | | | | 115 | | | | | 120 |
| Val | Lys | Pro | Arg | Ala | Pro | Gly | Asn | Leu | Thr | Val | His | Thr | Asn | Val | Ser | Asp | Thr | Leu | Leu |
| 121 | | | | 125 | | | | | 130 | | | | | 135 | | | | | 140 |
| Leu | Thr | Trp | Ser | Asn | Pro | Tyr | Pro | Pro | Asp | Asn | Tyr | Leu | Tyr | Asn | His | Leu | Thr | Tyr | Ala |
| 141 | | | | 145 | | | | | 150 | | | | | 155 | | | | | 160 |

TABLE 20-continued

SEQ ID NO: 98

```
Val Asn Ile Trp Ser Glu Asn Asp Pro Ala Asp Phe Arg Ile Tyr Asn Val Thr Tyr Leu
161             165                 170                 175                 180

Glu Pro Ser Leu Arg Ile Ala Ala Ser Thr Leu Lys Ser Gly Ile Ser Tyr Arg Ala Arg
181             185                 190                 195                 200

Val Arg Ala Trp Ala Gln Cys Tyr Asn Thr Thr Trp Ser Glu Trp Ser Pro Ser Thr Lys
201             205                 210                 215                 220

Trp His Asn Ser Tyr Arg Glu Pro Phe Glu Gln His
221             225                 230     232
```

The binding structure of hIL-4 and hIL-4Rα is shown in PDB (Protein Database) ID: 1IAR, the residues important for binding of the two proteins are Glu33 and Arg112 of hIL-4, and Tyr38, Ser95, Asp97 and Tyr208 of hIL-4Rα, have electrostatic interactions (LaPorte et al., 2008).

In addition, Leu67, Leu68, Asp92 and Val93 are also expected to be involved in binding to hIL-4, and these residues are recognized as epitopes of Leu67, Leu68, Asp92, and Val93 by other anti-hIL-4Rα antibodies (Medimmune Limited) (Korean Patent No. 1620539). FIG. 15A is a detailed view showing residues that plays an important role in binding in the binding structure of hIL-4 and hIL-4Rα, and an epitope region of the antibody.

For epitope mapping, a single mutation was introduced to convert each of the eight residues mentioned above (Tyr38, Ser95, Asp97, Tyr208, Leu67, Leu68, Asp92, Val93) to Ala, the eight hIL-4Rα proteins were purified in the same manner as in <Example 1>, and the purity was detected using 12% SDS-PAGE (FIG. 15B).

The protein was immobilized at 50 ng/well in a 96-well plate at room temperature for 1 hour and blocked at room temperature with 0.1% PBST containing 4% BSA (bovine serum albumin) for 1 hour. The solution was discarded, the residue was washed three times with 0.1% PBST, 5 nM hIL-4-mFc and 100 pM or 2.5 nM anti-HIL-4Rα antibodies (4R34 4R34.1, 4R34.1.9, Dupilumab analogue) were added at 25 μl/well to the blocked plate, and the reaction was allowed to proceed at room temperature for 1 hour. The solution was discarded, the residue was washed 3 times with 0.1% PBST, and then 25 μl of an anti-human IgG-HRP antibody (1:8000) as a secondary antibody was added to each well and allowed to react at room temperature for 1 hour. The solution was discarded, the residue was washed 3 times with PBST, and 25 μl of a TMB solution was added to each well, followed by color development at room temperature for 1 minute. The reaction was stopped with $H_2SO_4$ (1M), and absorbance was measured at 450 nm using an ELISA reader.

As a result, as can be seen from FIG. 15C, the dupilumab analogue exhibited low binding ability to the protein introduced with a single mutation having Ala instead of Val93 or Asp97. The 4R34, 4R34.1 and 4R34.1.19 antibodies recognized Leu67, Leu68, Asp92, Val93 and Asp97 of hIL-4Rα as epitopes. 4R34.1.19 recognizes Asp92 and Val93 residues of hIL-4Rα as epitopes, but does not recognize the same as epitopes more important than antibodies derived before affinity maturation. The reason for this is considered to be that other adjacent residues also contribute to binding to the antibody and still maintain binding ability. Dupilumab analogues are considered to have these residues as epitopes because the binding ability to hIL-4Rα decreased compared to wild-type IL-4Rα when Val93 and Asp97 were mutated to Ala. In conclusion, it was confirmed that the selected antibodies had epitopes different from those of other antibodies including dupilumab analogues.

In addition, Tyr38, Ser95, Asp97, and Tyr208 of hIL-4Rα have electrostatic interactions with Glu45 and Arg98 of hIL-13 (LaPorte et al., 2008). Thus, 4R34, 4R34.1, and 4R34.1.9 are considered to compete with hIL-13 for binding sites and inhibit the signaling of hIL-13.

Example 14: Evaluation of Ability of 4R34.1.19 Antibody to Inhibit Cell Proliferation of PHA-Activated PBMC Human PBMCs do not express much hIL-4Rα, but has been reported to express IL-4Rα in B cells and T cells as immune cells are divided when activated using a mitogen called "PHA (phytohaemagglutinin P, Sigma-Aldrich)". Thus, whether or not the 4R34.1.19 candidate antibody actually inhibits the proliferation of cells expressing hIL-4Rα in humans was determined using PBMC activated with PHA.

Specifically, in order to isolate immune cells (PBMC) from human peripheral blood, 5 ml of Ficoll (GE Healthcare) was charged in a 15 ml test tube. The collected blood was mixed at 1:1 with PBS (pH 7.4) and shaken, and then 10 ml of the mixture was added to a test tube containing Ficoll while preventing mixing with Ficoll, and centrifuged at 750 g in an unbroken state for 20 minutes. Then, the buffy coat formed on Ficoll was recovered and washed twice with PBS (pH 7.4) to obtain PBMCs containing T cells, B cells, NK cells and monocytes. The isolated normal PBMCs do not express a sufficiently large amount of IL-4Rα to observe the binding of IL-4Rα. Therefore, PBMCs were treated with mitogen called "PHA" (Sigma-Aldrich) for 72 hours to stimulate T cells and B cells to be activated. It has been reported that treatment with PHA causes immune cells to be divided and IL-4Rα receptors to be expressed in T cells and B cells. $1 \times 10^6$ cells/ml of PBMC was added to RPMI1640 medium containing 10% FBS, and 10 μg/ml of PHA was added thereto as a mitogen, followed by incubation in an incubator at 37° C. under 5% $CO_2$ for 72 hours. PBMCs activated with PHA were washed with cold PBS (pH 7.4), and $2 \times 10^4$ cells were prepared for each sample. PHA-activated PBMC ($2 \times 10^4$, 100 μL) was added to a 96-well plate (SPL, Korea), 50 μl of 2 pM IL-4 diluted with RPMI1640 medium containing 10% FBS was added, and 50 μl of 4R34.1.19, 4R34, 4R34.1 and dupilumab analogue antibodies diluted to 80 to 2,000 nM were added, followed by incubation at 37° C. in 5% $CO_2$ for 48 hours. Then, for the cell proliferation test, 70 μl of a CTG (CellTiter-Glo, Promega) reagent was added to each well and then allowed to react at room temperature for 20 hours, and luminescence was measured using a Cytation™ 3 Cell Imaging Multi-Mode Reader.

The result of analysis showed that the 4R34.1.19 antibody exhibited a notably improved effect of suppressing the proliferation of PHA-activated PBMCs than the 4R34.1 antibody as a template, and suppressed the proliferation of PHA-activated PBMCs to a degree similar to that of the control dupilumab analogue (FIG. 16).

Example 15: Evaluation of Ability of 4R34.1.9 Antibody to Inhibit Th2 Cell Differentiation Whether or not the 4R34.1.9 antibody inhibits the differentiation of Th2 cells by IL-4 was determined using the IL-4 ELISpot assay.

Specifically, an antibody conjugated with PE-cy5 recognizing CD4 in human PBMC, isolated in the same manner as in <Example 14> (Thermo Fisher Scientific), and an antibody conjugated with FITC, which recognizes CD45RO, a cell surface marker of memory cells (Thermo Fisher Scientific), were added and allowed to react at 4° C. for 30 minutes. The result was washed with PBS, and naive CD4⁺ T cells (CD4⁺ CD45⁻) were separated by FACS Aria III (BD biosciences, Korea). The isolated naive CD4⁺ T cells ($5\times10^4$ cells/well) were added to a 96-well flat-bottom plate, and sulfate latex beads ($5\times10^4$ cells/well) coated with anti-CD3 Ab/anti-CD28 Ab, 50 µl of Th2 differentiation medium (5 pg/ml anti-IFN-γ Ab, 5 ng/ml IL-2 and 10 ng/ml IL-4) and 50 µl of 4R34.1.9, 4R34, 4R34.1 and dupilumab analog antibodies diluted to 20-500 nM were added, followed by incubation in a 37° C., 5% $CO_2$ incubator for 7 days. The cultured cells were washed with cold PBS (pH 7.4), $2\times10^4$ cells for each sample were added to an ELISpot plate coated with anti-IL-4 capture antibody (Mabtech), and sulfate latex beads ($2\times10^4$ cells/well) coated with anti-CD3 Ab/anti-CD28 Ab were added thereto, followed by incubation in an incubator at 37° C. and 5% $CO_2$ for 24 hours. The ELISpot plate was washed with cold PBS (pH 7.4), and a biotin-conjugated IL-4 detection antibody (Mabtech) was bound thereto at room temperature for 2 hours. The result was washed with PBS (pH 7.4), bound with avidin-conjugated alkaline phosphatase (AP) (Mabtech) at room temperature for 1 hour, and washed with PBS (pH 7.4), and then a BCIP/NBT-plus substrate was added thereto to develop the color of IL-4 spots. The number of IL-4 spot-forming cells was measured using an ELISpot plate reader.

The result of analysis showed that the 4R34.1.19 antibody exhibited a remarkably improved effect of inhibiting the differentiation of naive T cells from normal and asthmatic patients into Th2 cells, compared to the template 4R34.1 antibody, and an effect of inhibiting differentiation similar to that of the control dupilumab analogue. This can be seen from the quantified values and representative images (FIGS. 17A and 17B).

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

INDUSTRIAL APPLICABILITY

The anti-hIL-4Rα antibody or antigen-binding fragment thereof of the present invention neutralizes hIL-4 activity and thereby has effects of suppressing the growth of patient-derived T cells and inhibiting the differentiation thereof into Th2 cells, thus being used for the treatment or prevention of inflammatory diseases, more particularly, allergic diseases such as dermatitis, asthma, allergic rhinitis or food allergic reactions, as well as diseases including, but not limited to, arthritis (including septic arthritis), herpes, chronic idiopathic urticaria, scleroderma, hypertrophic scarring, Whipple's disease, benign prostatic hyperplasia, lung disorders such as mild, moderate or severe asthma, inflammatory disorders such as inflammatory bowel diseases, Kawasaki disease, sickle cell disease, Churg-Strauss syndrome, Grave's disease, pre-eclampsia, Sjogren's syndrome, autoimmune lymphocytic proliferation syndrome, autoimmune hemolytic anemia, Barrett's esophagus, autoimmune uveitis, tuberculosis, and nephropathy.

The invention claimed is:

1. An isolated antibody or antigen-binding fragment thereof binding to human interleukin-4 receptor alpha (hIL-4Rα) comprising:

a heavy-chain complementarity-determining region (CDR) 1 of SEQ ID NO:11, a heavy-chain CDR2 of SEQ ID NO: 14, a heavy-chain CDR3 of SEQ ID NO: 23, a light-chain CDR1 of SEQ ID NO: 43, a light-chain CDR2 SEQ ID NO: 53; and a light-chain CDR3 of SEQ ID NO: 61;

a heavy-chain CDR1 of SEQ ID NO: 12, a heavy-chain CDR2 of SEQ ID NO: 15, a heavy-chain CDR3 of SEQ ID NO: 24, a light-chain CDR1 of SEQ ID NO: 44, a light-chain CDR2 SEQ ID NO: 54; and a light-chain CDR3 of SEQ ID NO: 62;

a heavy-chain CDR1 of SEQ ID NO:11, a heavy-chain CDR2 of SEQ ID NO: 16, a heavy-chain CDR3 of SEQ ID NO: 25, a light-chain CDR1 of SEQ ID NO: 45, a light-chain CDR2 SEQ ID NO: 55; and a light-chain CDR3 of SEQ ID NO: 63;

a heavy-chain CDR1 of SEQ ID NO: 13, a heavy-chain CDR2 of SEQ ID NO: 17, a heavy-chain CDR3 of SEQ ID NO: 26, a light-chain CDR1 of SEQ ID NO: 46, a light-chain CDR2 SEQ ID NO: 56; and a light-chain CDR3 of SEQ ID NO: 64;

a heavy-chain CDR1 of SEQ ID NO: 11, a heavy-chain CDR2 of SEQ ID NO: 18, a heavy-chain CDR3 of SEQ ID NO: 27, a light-chain CDR1 of SEQ ID NO: 47, a light-chain CDR2 SEQ ID NO: 57; and a light-chain CDR3 of SEQ ID NO: 65;

a heavy-chain CDR1 of SEQ ID NO: 11, a heavy-chain CDR2 of SEQ ID NO: 19, a heavy-chain CDR3 of SEQ ID NO: 28, a light-chain CDR1 of SEQ ID NO: 48, a light-chain CDR2 SEQ ID NO: 53; and a light-chain CDR3 of SEQ ID NO: 65;

a heavy-chain CDR1 of SEQ ID NO:11, a heavy-chain CDR2 of SEQ ID NO: 20, a heavy-chain CDR3 of SEQ ID NO: 29, a light-chain CDR1 of SEQ ID NO: 49, a light-chain CDR2 SEQ ID NO: 58; and a light-chain CDR3 of SEQ ID NO: 66;

a heavy-chain CDR1 of SEQ ID NO:11, a heavy-chain CDR2 of SEQ ID NO: 21, a heavy-chain CDR3 of SEQ ID NO: 30, a light-chain CDR1 of SEQ ID NO: 50, a light-chain CDR2 SEQ ID NO: 59; and a light-chain CDR3 of SEQ ID NO: 67;

a heavy-chain CDR1 of SEQ ID NO:11, a heavy-chain CDR2 of SEQ ID NO: 22, a heavy-chain CDR3 of SEQ ID NO: 31, a light-chain CDR1 of SEQ ID NO: 51, a light-chain CDR2 SEQ ID NO: 55; and a light-chain CDR3 of SEQ ID NO: 65;

a heavy-chain CDR1 of SEQ ID NO: 11, a heavy-chain CDR2 of SEQ ID NO: 14, a heavy-chain CDR3 of SEQ ID NO: 32, a light-chain CDR1 of SEQ ID NO: 52, a light-chain CDR2 SEQ ID NO: 60; and a light-chain CDR3 of SEQ ID NO: 68;

a heavy-chain CDR1 of SEQ ID NO: 11, a heavy-chain CDR2 of SEQ ID NO: 73, a heavy-chain CDR3 of SEQ ID NO: 32, a light-chain CDR1 of SEQ ID NO: 52, a light-chain CDR2 SEQ ID NO: 60; and a light-chain CDR3 of SEQ ID NO: 68;

a heavy-chain CDR1 of SEQ ID NO:11, a heavy-chain CDR2 of SEQ ID NO: 74, a heavy-chain CDR3 of SEQ ID NO: 32, a light-chain CDR1 of SEQ ID NO: 52, a light-chain CDR2 SEQ ID NO: 60; and a light-chain CDR3 of SEQ ID NO: 81;

a heavy-chain CDR1 of SEQ ID NO:11, a heavy-chain CDR2 of SEQ ID NO: 75, a heavy-chain CDR3 of SEQ ID NO: 32, a light-chain CDR1 of SEQ ID NO: 52, a light-chain CDR2 SEQ ID NO: 60; and a light-chain CDR3 of SEQ ID NO: 82;

a heavy-chain CDR1 of SEQ ID NO:11, a heavy-chain CDR2 of SEQ ID NO: 76, a heavy-chain CDR3 of SEQ ID NO: 32, a light-chain CDR1 of SEQ ID NO: 52, a light-chain CDR2 SEQ ID NO: 60; and a light-chain CDR3 of SEQ ID NO: 68;

a heavy-chain CDR1 of SEQ ID NO:84, a heavy-chain CDR2 of SEQ ID NO: 85, a heavy-chain CDR3 of SEQ ID NO: 32, a light-chain CDR1 of SEQ ID NO: 92, a light-chain CDR2 SEQ ID NO: 60; and a light-chain CDR3 of SEQ ID NO: 68;

a heavy-chain CDR1 of SEQ ID NO:84, a heavy-chain CDR2 of SEQ ID NO: 85, a heavy-chain CDR3 of SEQ ID NO: 32, a light-chain CDR1 of SEQ ID NO: 93, a light-chain CDR2 SEQ ID NO: 60; and a light-chain CDR3 of SEQ ID NO: 68;

a heavy-chain CDR1 of SEQ ID NO:84, a heavy-chain CDR2 of SEQ ID NO: 85, a heavy-chain CDR3 of SEQ ID NO: 32, a light-chain CDR1 of SEQ ID NO: 94, a light-chain CDR2 SEQ ID NO: 60; and a light-chain CDR3 of SEQ ID NO: 68;

a heavy-chain CDR1 of SEQ ID NO:84, a heavy-chain CDR2 of SEQ ID NO: 85, a heavy-chain CDR3 of SEQ ID NO: 32, a light-chain CDR1 of SEQ ID NO: 95, a light-chain CDR2 SEQ ID NO: 60; and a light-chain CDR3 of SEQ ID NO: 68;

a heavy-chain CDR1 of SEQ ID NO:84, a heavy-chain CDR2 of SEQ ID NO: 85, a heavy-chain CDR3 of SEQ ID NO: 32, a light-chain CDR1 of SEQ ID NO: 96, a light-chain CDR2 SEQ ID NO: 60; and a light-chain CDR3 of SEQ ID NO: 68; or a heavy-chain CDR1 of SEQ ID NO:84, a heavy-chain CDR2 of SEQ ID NO: 85, a heavy-chain CDR3 of SEQ ID NO: 32, a light-chain CDR1 of SEQ ID NO: 97, a light-chain CDR2 SEQ ID NO: 60; and a light-chain CDR3 of SEQ ID NO: 68.

2. The antibody or antigen-binding fragment thereof according to claim 1, wherein the antibody recognizes an epitope including an amino acid residue selected from the group consisting of Leu67, Leu68, Asp92, Val93 and Asp97 in hIL-4Rα of SEQ ID NO: 98.

3. The antibody or antigen-binding fragment thereof according to claim 1, wherein the antibody binds to an epitope including amino acid residues of Leu67, Leu68, Asp92, Val93 and Asp97 in hIL-4Rα of SEQ ID NO: 98, and binds to hIL-4Rα competitively with human interleukin-4 (hIL-4) and human interleukin-13 (hIL-13).

4. The antibody or antigen-binding fragment thereof according to claim 1, wherein the antibody has a higher antigen dissociation rate (off-rate) than other antibodies such that it has lower antigen-mediated antibody clearance in vivo to increase the serum half-life in vivo.

5. The antibody or antigen-binding fragment thereof according to claim 1, wherein the antibody or antigen-binding fragment thereof comprises a heavy-chain variable region comprising a sequence selected from the group consisting of SEQ ID NOs: 1 to 10, 69 to 72, and 83.

6. The antibody or antigen-binding fragment thereof according to claim 1, wherein the antibody or antigen-binding fragment thereof comprises a light-chain variable region comprising a sequence selected from the group consisting of SEQ ID NOs: 33 to 42, 77 to 80, and 86 to 91.

7. A method of producing an isolated antibody or antigen-binding fragment thereof binding to human interleukin-4 receptor alpha (hIL-4Rα) with an equilibrium dissociation constant ($K_D$) of less than 150 pM, as measured by surface plasmon resonance (SPR), the method comprising:

a) culturing a cell transformed with a vector comprising a nucleic acid, said nucleic acid coding for the antibody or antigen-binding fragment thereof according to claim 1; and (b) recovering an antibody or antigen-binding fragment thereof from the cultured cell.

8. A conjugate of the antibody or antigen-binding fragment thereof according to claim 1, and a bioactive molecule selected from the group consisting of a peptide, a protein, a small-molecule drug, a nucleic acid, a nanoparticle, a liposome, and a combination thereof, wherein the antibody or antigen-binding fragment is genetically fused or chemically conjugated with the bioactive molecule.

* * * * *